(12) United States Patent
Vågesjö

(10) Patent No.: US 10,696,974 B2
(45) Date of Patent: Jun. 30, 2020

(54) METHODS FOR WOUND HEALING

(71) Applicant: Ilya Pharma AB, Uppsala (SE)

(72) Inventor: Evelina Vågesjö, Uppsala (SE)

(73) Assignee: ILYA PHARMA AB, Uppsala (SE)

( * ) Notice: Subject to any disclaimer, the term of this patent is extended or adjusted under 35 U.S.C. 154(b) by 0 days.

(21) Appl. No.: 15/538,384

(22) PCT Filed: Dec. 23, 2015

(86) PCT No.: PCT/EP2015/081146
§ 371 (c)(1),
(2) Date: Jun. 21, 2017

(87) PCT Pub. No.: WO2016/102660
PCT Pub. Date: Jun. 30, 2016

(65) Prior Publication Data
US 2018/0187202 A1    Jul. 5, 2018

(30) Foreign Application Priority Data

Dec. 23, 2014 (SE) ...................... 1451658

(51) Int. Cl.
| C12N 15/74 | (2006.01) |
| A61K 35/744 | (2015.01) |
| A61K 38/19 | (2006.01) |
| A61K 45/06 | (2006.01) |
| A61L 26/00 | (2006.01) |
| C07K 14/52 | (2006.01) |
| C12R 1/225 | (2006.01) |

(52) U.S. Cl.
CPC .......... *C12N 15/746* (2013.01); *A61K 35/744* (2013.01); *A61K 38/19* (2013.01); *A61K 45/06* (2013.01); *A61L 26/0057* (2013.01); *C07K 14/521* (2013.01); *C12R 1/225* (2013.01); *A61L 2300/252* (2013.01)

(58) Field of Classification Search
None
See application file for complete search history.

(56) References Cited

U.S. PATENT DOCUMENTS

| 7,074,616 B1 * | 7/2006 | Kishimoto ......... C07K 14/7158 435/320.1 |
| 7,776,564 B2 * | 8/2010 | Chu ..................... C07K 14/522 435/252.3 |
| 8,367,109 B2 | 2/2013 | Chidambaram et al. |
| 8,679,477 B2 | 3/2014 | Penn et al. |
| 2001/0006642 A1 | 7/2001 | Steidler et al. |
| 2005/0101005 A1 | 5/2005 | Steidler |
| 2007/0110723 A1 | 5/2007 | Hans et al. |
| 2007/0258965 A1 | 11/2007 | Remaut et al. |
| 2008/0254014 A1 | 10/2008 | Rottiers et al. |
| 2008/0274084 A1 | 11/2008 | Rottiers et al. |
| 2009/0074734 A1 | 3/2009 | Rottiers |
| 2009/0148389 A1 | 6/2009 | Rottiers et al. |
| 2010/0080774 A1 | 4/2010 | Steidler et al. |
| 2010/0104601 A1 | 4/2010 | Rottiers |
| 2010/0143305 A1 * | 6/2010 | Lemke ................. A61K 35/747 424/93.2 |
| 2010/0143447 A1 | 6/2010 | Hansen |
| 2010/0178273 A1 | 7/2010 | Rottiers |
| 2010/0267612 A1 | 10/2010 | Tabata |
| 2010/0272679 A1 | 10/2010 | Penn et al. |
| 2010/0303777 A1 | 12/2010 | De Creus et al. |
| 2011/0150850 A1 | 6/2011 | Steidler |
| 2011/0182859 A1 | 7/2011 | Hyde |
| 2012/0039853 A1 | 2/2012 | Corveleyn et al. |
| 2012/0058086 A1 | 3/2012 | Velazquez et al. |
| 2012/0183503 A1 | 7/2012 | Steidler et al. |
| 2013/0303597 A1 | 11/2013 | Penn et al. |
| 2013/0323819 A1 * | 12/2013 | Hammarstrom ..... A61K 35/747 435/252.3 |
| 2014/0065209 A1 | 3/2014 | Putaala et al. |
| 2014/0105863 A1 | 4/2014 | Vanden-Broucke et al. |

FOREIGN PATENT DOCUMENTS

| CN | 101985052 A | 3/2011 |
| EP | 1104808 A1 | 6/2001 |
| EP | 2243487 A1 | 10/2010 |
| EP | 2450062 A4 | 11/2012 |
| WO | WO9714806 A2 | 4/1997 |
| WO | WO2008074331 A1 | 6/2008 |
| WO | WO2009079451 A2 | 6/2009 |
| WO | WO2011026041 A2 | 3/2011 |

(Continued)

OTHER PUBLICATIONS

Kit. Definition of Kit in English by Oxford Dictionaries. https://en.oxforddictionaries.com/definition/kit retrieved Oct. 23, 2018.*

Mathiesen et al. Journal of Applied Microbiology 105 (2008) 215-226.*

O'Toole, Paul W. et al., "Next-generation probiotics: the spectrum from probiotics to live biotherapeutics", Nature Microbiology 2:1-6 (2017).

Babincova, Melania et al., "Bacteria as a Shuttle Vector Producing SDF-1 for Attraction of Hematopoietic Stem Cells to Desired Sites in the Body", Correspondence/Medical Hypotheses, 2007, 68:233.

Babincova, Melania et al., "Pepper Soup as an Antioxidant Nutrition Therapy", Correspondence/Medical Hypotheses, 2009, 73:854.

Badillo, Andrea T, M.D. et al., "Lentiviral Gene Transfer of SDF-1a to Wounds Improves Diabetic Wound Healing", Journal of Surgical Research, 2007, 143:35-42.

(Continued)

*Primary Examiner* — Oluwatosin A Ogunbiyi
(74) *Attorney, Agent, or Firm* — Lewis Roca Rothgerber Christie LLP

(57) ABSTRACT

The invention relates to plasmids capable of expressing a protein targeting immune cells when transformed into a lactic acid bacterial cell, wherein the protein is chosen from the group consisting of murine and human CXCL12 1α; CXCL17 and Ym1. The invention further relates to lactic acid bacteria transformed with a said plasmid, as well as the use of said lactic acid bacteria for wound healing in humans and animals.

27 Claims, 25 Drawing Sheets

Specification includes a Sequence Listing.

(56) References Cited

FOREIGN PATENT DOCUMENTS

| WO | WO2010123699 A2 | 10/2011 |
|---|---|---|
| WO | WO2013041672 A1 | 3/2013 |
| WO | WO2013041673 A1 | 3/2013 |
| WO | WO 2013153358 A1 | 10/2013 |
| WO | WO2014145236 A2 | 9/2014 |
| WO | 2016124266 A1 | 8/2016 |
| WO | WO2014179266 A2 | 11/2016 |

OTHER PUBLICATIONS

Bellocq, Agnes et al., "Low Environmental pH is Responsible for the Induction of Nitric-oxide Synthase in Macrophages", J Biol Chem., 1998, 273(9):5086-5092.

Bhaumik, S. et al., "Optical imaging of Renilla luciferase reporter gene expression in living mice", PNAS, 2002, 99 (1):377-382.

Burkhardt, Amanda M. et al., "CXCL17 Is a Mucosal Chemokine Elevated in Idiopathic Pulmonary Fibrosis That Exhibits Broad Antimicrobial Activity", The Journal of Immunology, 2012, 188:6399-6406.

Böhmer, Nico et al.,"A novel manganese starvation-inducible expression system for Lactobacillus plantarum", FEMS Microbiol Lett., 2013, 342(30):37-44.

Castilla, Diego M. et al., "A Novel Autologous Cell Based Therapy to Promote Diabetic Wound Healing", Ann. Surg., 2012, 256(4): 560-572.

Demidova-Rice, Tatiana N., PhD et al., "Acute and Impaired Wound Healing: Pathophysiology and Current Methods for Drug Delivery, Part 1: Normal and Chronic Wounds: Biology, Causes and Approaches to Care", Advances in Skin and Wound Care, 2012, 25(7):304-314.

Demidova-Rice, Tatiana N., PhD et al., "Acute and Impaired Wound Healing: Pathophysiology and Current Methods for Drug Delivery, Part 2: Role of Growth Factors in Normal and Pathological Wound Healing: Therapeutic Potential and Methods of Delivery", Advances in Skin and Wound Care, 2012, 25(8):349-370.

Drury, Luke J. et al., "Monomeric and dimeric CXCL12 inhibit Metastasis through distinct CSCR4 interactions and signaling pathways", PNAS, 2011, 108:43:17655-17660.

Duong, Tri et al., "Construction of vectors for inducible and constitutive gene expression in Lactobacillus", Microbial Biotechnology, 2010, 4(3):357-367.

Eijsink, Vincent, G.H. et al., "Production of class II bacteriocins by lactic acid bacteria; an example of biological warfare and communication", Antonie van Leeuwenhoek, 2002, 81: 639-654.

Gao, Zhan et al., "Molecular analysis of human forearm superficial skin bacterial biota", PNAS, 2007, 104 (8)2927-2932.

Gethin, Georgina et al., "The significance of surface pH in chronic wounds", Wounds UK, 2007, 3(3): 52-56.

Goren, Itamar et al., "Cell Injury, Repair, Aging and Apoptosis, Uptake of Neutrophil-Derived Ym1 Protein Distinguishes Wound Macrophages in the Absence of Interleukin-4 Signaling in Murine Wound Healing", The American Journal of Pathology, 184(12):3249-3261 (2014).

Hatse, Sigrid et al., "Fluorescent CXCL12AF647 as a Novel Probe for Nonradioactive CXCL12/CXCR4 Cellular Interaction Studies", Cytometry Part A, 2004, 61A:178-188.

Hatterman, Kristen et al., "Chemokine expression profile of freshly isolated human glioblastoma-associated macrophages/microglia", Oncology Reports, 2014, 32:270-276.

Holm, Liisa et al., "Protein Structure Comparison by Alignment of Distance Matrices", J. Mol. Biol., 1993, 233:123-138.

Hühne, Kathrin et al., "Analysis of the sakacin P gene cluster from Lactobacillus sake Lb674 and its expression in sakacin-negative Lb. sake strains", Microbiology, 1996, 142:1437-1448.

Lee, Wei-Yu et al., "CXCL17, an orphan chemokine, acts as a novel angiogenic and anti-inflammatory factor", Am J Physiol Endocrinol Metab, 2013, 304:E32-E40.

Massena, Sara et al., "Phagocytes, Granulocytes, and Myelopoiesis, Identification and characterization pf VEGF-A-responsive neutrophils expressing CD49d, VEGFR1, and CXCR4 in mice and humans", Blood, 2015, 126 (17):2016-2026 (doi: 10.1182/blood-2015-03-631572. Epub 2015).

Nakamura, Yoko et al., "Enhanced wound healing by topical administration of mesenchymal stem cells transfected with stromal cell-derived factor-1", Biomaterials 2013, 34: 9393-9400.

Nesmelova, Irina V. et al., "CXC and CC Chemokines Form Mixed Heterodimers, Association Free Energies from Molecular Dynamics Simulations and Experimental Correlations", J Biol Chem, 2008, 283(35):24155-24166, DOI 10.1074/jbc.M803308200.

Nyman, Erika et al., "Hyaluronic acid, an important factor in the wound healing properties of amniotic fluid: In vitro studies of re-epithelialisation in human skin wounds", J Plast Surg Hand Surg., 2013, 47(2): 89-92.

Owhashi, Makoto et al., "Identification of a Novel Eosinophil Chemotactic Cytokine (ECF-L) as a Chitinase Family Protein", J. Biological Chemistry 2000, 275(2): 1279-1286.

Pearson, William R. et al., "Improved tools for biological sequence comparison", PNAS 1988, 85: 2444-2448.

Poutahidis, Theofilos et al., "Microbial Symbionts Accelerate Wound Healing via the Neuropeptide Hormone Oxytocin", Plos One 2013, 8(10) e78898:1-17.

Ramos, Alberto N., "Antipathogenic properties of Lactobacillus plantarum on Pseudomonas aeruginosa: The potential use of its supernatants in the treatment of infected chronic wounds", Wound Repair and Regeneration, 2012, 20:552-562.

Restivo, Terry E., "Application of the Chemokine CXCL12 Expression Plasmic Restores Wound Healing to Near Normal in Diabetic Mouse Model", The Journal of Trauma, 2010, 69(2): 392-398.

Salcedo, Rosalba et al., "Vascular Endothelial Growth Factor and Basic Fibroblast Growth Factor Induce Expressio of CXCR4 on Human Endothelial Cells", The Am. J. of Pathology, 1999, 154(4): 1125-1135.

Sekhar, M. Sonal et al., "Topical application/formulation of probiotics: Will it be a novel treatment approach for diabetic foot ulcer", Medical Hypotheses 2014, 82: 86-88.

Sørvig, Elisabeth et al., "Construction of vectors for inducible gene expression in Lactobacillus sakei and L. plantarum", FEMS Microbiol Lett. 2003, 229: 119-126.

Sørvig, Elisabeth et al., "High-level, inducible gene expression in Lactobacillus sakei and Lactobacillus plantarum using versatile expression vectors", Microbiology 2005, 151: 2439-2449.

Thompson, Julie D., "CLUSTAL W: improving the sensitivity of progressive multiple sequence alignment through sequence weighting, position-specific gap penalties and weight matrix choice", Nucleic Acids Res. 1994, 22(22): 4673-4680.

Vågesjö, Evelina et al., "Immunological Shielding by Induced Recruitment of Regulatory T-Lymphocytes Delays Rejection of Islets Transplanted in Muscle", Cell Transplantation, 2015, 24: 263-276.

Altschul, Stephen F., et al., Gapped BLAST and PSI-BLAST: a new generation of protein database search programs, Nucleic Acids Research (1997), vol. 25, No. 17, pp. 3389-3402.

Babincova, Melania, et al., Probiotic culture genetically modified to produce SDF-1 chemo-kine may be usefor for stem cell based therapy of Crohn's disease, Correspondence/Medical Hypotheses (2009), vol. 73, 1 sheet.

Cortes-Perez, N.G. et al., Production of biologically active CXC chemokines by Lactococcus lactis: Evaluation of its potential as a novel mucosal vaccine adjuvant, Vaccine, vol. 26, (2008) pp. 5778-5783.

Garcia-Cayuela, T., et al., Fluorescent protein vectors for promoter analysis in lactic acid bacteria and *Escherichia coli*, Appl. Microbiol Biotechnol (2012) vol. 96, pp. 171-181.

Holm, Liisa, et al., Touring protein fold space with Dali/FSSP, Nucleic Acids Research (1998), vol. 26, No. 1, pp. 316-319.

Holm, Liisa, et al., Dali: a network tool for protein structure comparison, Trends in Biochem. Sci., Nov. 1995, vol. 20, pp. 478-480.

Villatoro-Hernandez, J., et al., Secretion of biologically active interferon-gamma inducible protein-10 (IP-10) by Lactococcus lactis; Microbial Cell Factories, Bio Med Central, Jul. 28, 2008, 8 pages.

(56) References Cited

OTHER PUBLICATIONS

Villatoro-Hernandez, J., et al., Murine inferferon-gamma inducible protein-10 (IP-10) secreted by lactococcus lactis chemo-attracts human CD3+ lymphocytes, Biotechnology Letters (2009) vol. 31, pp. 1795-1800.
European Patent Office action dated May 10, 2019, issued in corresponding application No. 15822941.9, 4 pages.
Japanese Office action issued in corresponding application No. JP 2017-552233, dated Jan. 4, 2019, 5 pages.
Australian Office action issued in corresponding AU No. 2015370982, dated Jun. 22, 2018, 12 pages.
Suebwongsa, Namfon et al., Cloning and expression of a codon-optimized gene encoding the influenza A virus nucleocapsid protein in Lactobacillus casei, International Microbiology (2013) 16:93-101.
EP Office Action dated Apr. 24, 2020 in corresponding Application No. 15822941.9, 23 pages.
Third Party Observation dated Mar. 27, 2020, filed in corresponding EP Application No. 15822941.9, with Annexes 129 pages.
Vagesjo et al., Supporting Information, PNAS, 10.1073/pnas. 1716580115, 10 pages, available at www.pnas.org/cgi/content/short/1716580115, date unknown (Annex 4 to Third Party Observation dated Mar. 27, 2020).
Unknown, BT-SPEC-2007, OXOID Quality Assurance Product Specification, M17 Broth (OXOID), dated Oct. 14, 2008, 2 pages (Annex 5 to Third Party Observation dated Mar. 27, 2020).
Unknown, 69966 MRS Broth (Lactobacillus Broth acc. De Man, Rogosa and Sharpe), 2018 Merck KGaA, 2 pages, available at www.sigmaaldrich.com (Annex 6 to Third Party Observation dated Mar. 27, 2020).
Vagesjo et al., Accelerated wound healing in mice by on-site production and delivery of CXCL12 by transformed lactic acid bactera, PNAS, vol. 115, No. 8, pp. 1895-1990, 2018.
Babincova et al., Bacteria as a shuttle vector producing SDF-1 for attraction of hematopoietic stem cells to desired sites in body, 2007, Correspondence, p. 233, doi:10.1016/j.mehy2006.06.028 (Annex 7 to Third Party Observation dated Mar. 27, 2020).
Sorvig et al., High-level, inducible gene expression in Lactobacillus sakei and Lactobacillus plantarum using versatile expression vectors, Microbiology (2005), 151, pp. 2439-2449 (Annex 9 to Third Party Observation dated Mar. 27, 2020).
Laguri et al., The Novel CXCL12y Isoform Encodes an Unstructured Cationic Domain Which Regulates Bioactivity and Interaction with Both Glycosaminoglycans and CXCR4, PLoS One, Oct. 2007, Issue 10, e1110, pp. 1-10.

\* cited by examiner

FIG. 16
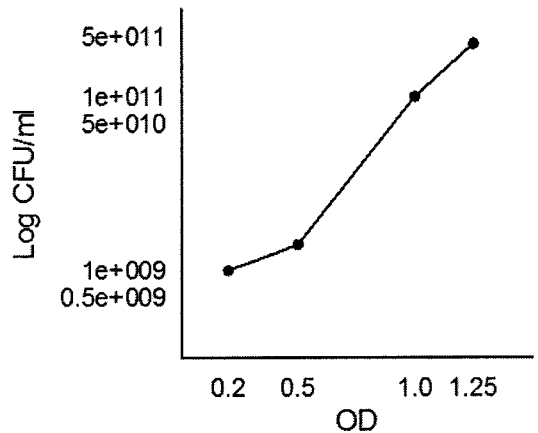
FIG. 17A
FIG. 17B
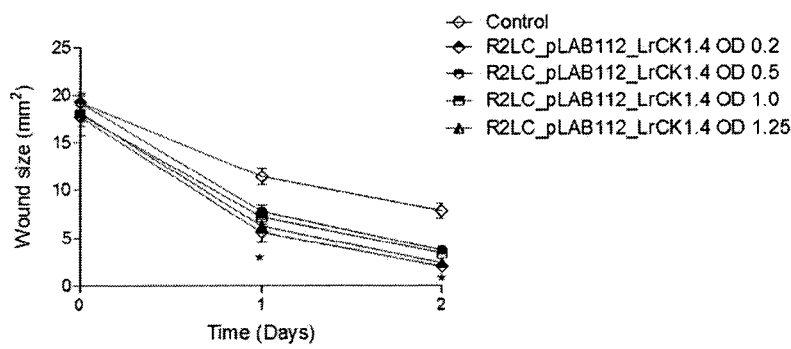
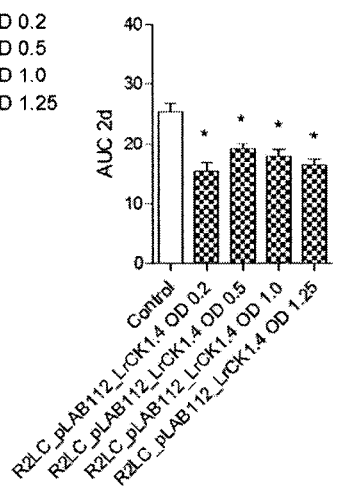

```
                        SEQUENCE LISTING

<160> NUMBER OF SEQ ID NOS: 26

<210> SEQ ID NO 1
<211> LENGTH: 299
<212> TYPE: DNA
<213> ORGANISM: Mus musculus
<220> FEATURE:
<221> NAME/KEY: CDS
<222> LOCATION: (3)..(293)

<400> SEQUENCE: 1 cc atg gca aaa ttt tgg aag aaa gca cta tta aca att gca gcc tta        47
   Met Ala Lys Phe Trp Lys Lys Ala Leu Leu Thr Ile Ala Ala Leu
   1               5                   10                  15 aca gtc ggc acc tcc gca gga att aca agc gtt tct gcc aaa ccg gta       95
Thr Val Gly Thr Ser Ala Gly Ile Thr Ser Val Ser Ala Lys Pro Val
                20                  25                  30 agt ttg tca tat cga tgt cca tgc cgg ttt ttc gaa tct cat att gca      143
Ser Leu Ser Tyr Arg Cys Pro Cys Arg Phe Phe Glu Ser His Ile Ala
            35                  40                  45 cgc gct aat gtc aaa cac tta aag att ctt aat act cct aat tgt gct      191
Arg Ala Asn Val Lys His Leu Lys Ile Leu Asn Thr Pro Asn Cys Ala
        50                  55                  60 ttg cag att gtt gca cgt tta aag aat aac aat cgt caa gtt tgt atc      239
Leu Gln Ile Val Ala Arg Leu Lys Asn Asn Asn Arg Gln Val Cys Ile
    65                  70                  75 gat cca aag ctt aaa tgg att caa gag tac tta gaa aag gcc tta aac      287
Asp Pro Lys Leu Lys Trp Ile Gln Glu Tyr Leu Glu Lys Ala Leu Asn
80                  85                  90                  95 aaa taa ctcgag                                                       299
Lys

<210> SEQ ID NO 2
<211> LENGTH: 96
<212> TYPE: PRT
<213> ORGANISM: Mus musculus

<400> SEQUENCE: 2

Met Ala Lys Phe Trp Lys Lys Ala Leu Leu Thr Ile Ala Ala Leu Thr
1               5                   10                  15

Val Gly Thr Ser Ala Gly Ile Thr Ser Val Ser Ala Lys Pro Val Ser
            20                  25                  30

Leu Ser Tyr Arg Cys Pro Cys Arg Phe Phe Glu Ser His Ile Ala Arg
```

```
                35                  40                  45
Ala Asn Val Lys His Leu Lys Ile Leu Asn Thr Pro Asn Cys Ala Leu
        50                  55                  60

Gln Ile Val Ala Arg Leu Lys Asn Asn Asn Arg Gln Val Cys Ile Asp
65                  70                  75                  80

Pro Lys Leu Lys Trp Ile Gln Glu Tyr Leu Glu Lys Ala Leu Asn Lys
                85                  90                  95

<210> SEQ ID NO 3
<211> LENGTH: 89
<212> TYPE: PRT
<213> ORGANISM: Mus musculus

<400> SEQUENCE: 3

Met Asp Ala Lys Val Val Ala Val Leu Ala Leu Val Leu Ala Ala Leu
1               5                   10                  15

Cys Ile Ser Asp Gly Lys Pro Val Ser Leu Ser Tyr Arg Cys Pro Cys
            20                  25                  30

Arg Phe Phe Glu Ser His Ile Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85

<210> SEQ ID NO 4
<211> LENGTH: 299
<212> TYPE: DNA
<213> ORGANISM: Homo sapiens
<220> FEATURE:
<221> NAME/KEY: CDS
<222> LOCATION: (3)..(293)

<400> SEQUENCE: 4 cc atg gca aaa ttt tgg aag aaa gca cta tta aca att gca gcc tta         47
   Met Ala Lys Phe Trp Lys Lys Ala Leu Leu Thr Ile Ala Ala Leu
   1               5                   10                  15 aca gtc ggc acc tcc gca gga att aca agc gtt tct gcc aaa ccg gta        95
Thr Val Gly Thr Ser Ala Gly Ile Thr Ser Val Ser Ala Lys Pro Val
            20                  25                  30 agt ttg tca tat cga tgt cca tgc cgg ttt ttc gaa tct cat gtt gca       143
Ser Leu Ser Tyr Arg Cys Pro Cys Arg Phe Phe Glu Ser His Val Ala
            35                  40                  45 cgc gct aat gtc aaa cac tta aag att ctt aat act cct aat tgt gct       191
Arg Ala Asn Val Lys His Leu Lys Ile Leu Asn Thr Pro Asn Cys Ala
        50                  55                  60 ttg cag att gtt gca cgt tta aag aat aac aat cgt caa gtt tgt atc       239
Leu Gln Ile Val Ala Arg Leu Lys Asn Asn Asn Arg Gln Val Cys Ile
    65                  70                  75 gat cca aag ctt aaa tgg att caa gag tac tta gaa aag gcc tta aac       287
Asp Pro Lys Leu Lys Trp Ile Gln Glu Tyr Leu Glu Lys Ala Leu Asn
80                  85                  90                  95 aaa taa ctcgag                                                        299
Lys

<210> SEQ ID NO 5
<211> LENGTH: 96
<212> TYPE: PRT
```

<213> ORGANISM: Homo sapiens

<400> SEQUENCE: 5

Met Ala Lys Phe Trp Lys Lys Ala Leu Leu Thr Ile Ala Ala Leu Thr
1               5                   10                  15

Val Gly Thr Ser Ala Gly Ile Thr Ser Val Ser Ala Lys Pro Val Ser
            20                  25                  30

Leu Ser Tyr Arg Cys Pro Cys Arg Phe Phe Glu Ser His Val Ala Arg
        35                  40                  45

Ala Asn Val Lys His Leu Lys Ile Leu Asn Thr Pro Asn Cys Ala Leu
    50                  55                  60

Gln Ile Val Ala Arg Leu Lys Asn Asn Asn Arg Gln Val Cys Ile Asp
65                  70                  75                  80

Pro Lys Leu Lys Trp Ile Gln Glu Tyr Leu Glu Lys Ala Leu Asn Lys
                85                  90                  95

<210> SEQ ID NO 6
<211> LENGTH: 89
<212> TYPE: PRT
<213> ORGANISM: Homo sapiens

<400> SEQUENCE: 6

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85

<210> SEQ ID NO 7
<211> LENGTH: 386
<212> TYPE: DNA
<213> ORGANISM: Mus musculus
<220> FEATURE:
<221> NAME/KEY: CDS
<222> LOCATION: (3)..(380)

<400> SEQUENCE: 7 cc atg gca aaa ttt tgg aag aaa gca cta tta aca att gca gcc tta        47
   Met Ala Lys Phe Trp Lys Lys Ala Leu Leu Thr Ile Ala Ala Leu
   1               5                   10                  15 aca gtc ggc acc tcc gca gga att aca agc gtt tct gcc agc cca aat      95
Thr Val Gly Thr Ser Ala Gly Ile Thr Ser Val Ser Ala Ser Pro Asn
            20                  25                  30 cca ggg gtc gcc aga tct cac ggc gac cag cac ctg gct cct agg aga    143
Pro Gly Val Ala Arg Ser His Gly Asp Gln His Leu Ala Pro Arg Arg
        35                  40                  45 tgg ctc ctg gaa ggc ggc caa gaa tgt gag tgc aaa gat tgg ttc ctg    191
Trp Leu Leu Glu Gly Gly Gln Glu Cys Glu Cys Lys Asp Trp Phe Leu
    50                  55                  60 caa gcc ccg aag aga aaa gcc aca gct gtg ctg ggg cca cca aga aag    239
Gln Ala Pro Lys Arg Lys Ala Thr Ala Val Leu Gly Pro Pro Arg Lys
65                  70                  75

```
cag tgc ccc tgt gat cat gtg aag ggc aga gaa aag aaa aat aga cac      287
Gln Cys Pro Cys Asp His Val Lys Gly Arg Glu Lys Lys Asn Arg His
 80                  85                  90                  95 caa aag cac cac aga aag agc caa aga ccc tcc aga gcc tgc cag caa      335
Gln Lys His His Arg Lys Ser Gln Arg Pro Ser Arg Ala Cys Gln Gln
                100                 105                 110 ttt ctc aaa agg tgt cac cta gcc agc ttt gct ctg cct ttg tag          380
Phe Leu Lys Arg Cys His Leu Ala Ser Phe Ala Leu Pro Leu
                115                 120                 125 ctcgag                                                                386

<210> SEQ ID NO 8
<211> LENGTH: 125
<212> TYPE: PRT
<213> ORGANISM: Mus musculus

<400> SEQUENCE: 8

Met Ala Lys Phe Trp Lys Lys Ala Leu Leu Thr Ile Ala Ala Leu Thr
  1               5                  10                  15

Val Gly Thr Ser Ala Gly Ile Thr Ser Val Ser Ala Ser Pro Asn Pro
             20                  25                  30

Gly Val Ala Arg Ser His Gly Asp Gln His Leu Ala Pro Arg Arg Trp
         35                  40                  45

Leu Leu Glu Gly Gly Gln Glu Cys Glu Cys Lys Asp Trp Phe Leu Gln
 50                  55                  60

Ala Pro Lys Arg Lys Ala Thr Ala Val Leu Gly Pro Pro Arg Lys Gln
 65                  70                  75                  80

Cys Pro Cys Asp His Val Lys Gly Arg Glu Lys Lys Asn Arg His Gln
                 85                  90                  95

Lys His His Arg Lys Ser Gln Arg Pro Ser Arg Ala Cys Gln Gln Phe
            100                 105                 110

Leu Lys Arg Cys His Leu Ala Ser Phe Ala Leu Pro Leu
            115                 120                 125

<210> SEQ ID NO 9
<211> LENGTH: 119
<212> TYPE: PRT
<213> ORGANISM: Mus musculus

<400> SEQUENCE: 9

Met Lys Leu Leu Ala Ser Pro Phe Leu Leu Leu Pro Val Met Leu
  1               5                  10                  15

Met Ser Met Val Phe Ser Ser Pro Asn Pro Gly Val Ala Arg Ser His
             20                  25                  30

Gly Asp Gln His Leu Ala Pro Arg Arg Trp Leu Leu Glu Gly Gly Gln
         35                  40                  45

Glu Cys Glu Cys Lys Asp Trp Phe Leu Gln Ala Pro Lys Arg Lys Ala
 50                  55                  60

Thr Ala Val Leu Gly Pro Pro Lys Gln Cys Pro Cys Asp His Val
 65                  70                  75                  80

Lys Gly Arg Glu Lys Lys Asn Arg His Gln Lys His His Arg Lys Ser
                 85                  90                  95

Gln Arg Pro Ser Arg Ala Cys Gln Gln Phe Leu Lys Arg Cys His Leu
            100                 105                 110

Ala Ser Phe Ala Leu Pro Leu
            115
```

```
<210> SEQ ID NO 10
<211> LENGTH: 386
<212> TYPE: DNA
<213> ORGANISM: Homo sapiens
<220> FEATURE:
<221> NAME/KEY: CDS
<222> LOCATION: (3)..(380)

<400> SEQUENCE: 10 cc atg gca aaa ttt tgg aag aaa gca cta tta aca att gca gcc tta        47
   Met Ala Lys Phe Trp Lys Lys Ala Leu Leu Thr Ile Ala Ala Leu
   1               5                   10                  15 aca gtc ggc acc tcc gca gga att aca agc gtt tct gcc tca tta aat       95
Thr Val Gly Thr Ser Ala Gly Ile Thr Ser Val Ser Ala Ser Leu Asn
             20                  25                  30 cca gga gta gca cgg ggt cat cga gat cgg gga caa gca agt cgg cgt      143
Pro Gly Val Ala Arg Gly His Arg Asp Arg Gly Gln Ala Ser Arg Arg
         35                  40                  45 tgg tta caa gaa ggt ggt caa gaa tgt gaa tgt aaa gat tgg ttt tta      191
Trp Leu Gln Glu Gly Gly Gln Glu Cys Glu Cys Lys Asp Trp Phe Leu
     50                  55                  60 cgt gct cca cgt cgg aag ttt atg act gtt agt ggt ctt cca aag aaa      239
Arg Ala Pro Arg Arg Lys Phe Met Thr Val Ser Gly Leu Pro Lys Lys
 65                  70                  75 caa tgt cct tgt gat cat ttt aag gga aat gtt aag aaa act cga cac      287
Gln Cys Pro Cys Asp His Phe Lys Gly Asn Val Lys Lys Thr Arg His
 80                  85                  90                  95 caa cgt cat cac cgg aaa cct aat aag cat tca cgg gca tgt caa caa      335
Gln Arg His His Arg Lys Pro Asn Lys His Ser Arg Ala Cys Gln Gln
                100                 105                 110 ttt ctt aaa caa tgt caa ctt cgt tct ttt gct ctt cct ctt taa         380
Phe Leu Lys Gln Cys Gln Leu Arg Ser Phe Ala Leu Pro Leu
                115                 120                 125 ctcgag                                                               386

<210> SEQ ID NO 11
<211> LENGTH: 125
<212> TYPE: PRT
<213> ORGANISM: Homo sapiens

<400> SEQUENCE: 11

Met Ala Lys Phe Trp Lys Lys Ala Leu Leu Thr Ile Ala Ala Leu Thr
1               5                   10                  15

Val Gly Thr Ser Ala Gly Ile Thr Ser Val Ser Ala Ser Leu Asn Pro
             20                  25                  30

Gly Val Ala Arg Gly His Arg Asp Arg Gly Gln Ala Ser Arg Arg Trp
         35                  40                  45

Leu Gln Glu Gly Gly Gln Glu Cys Glu Cys Lys Asp Trp Phe Leu Arg
     50                  55                  60

Ala Pro Arg Arg Lys Phe Met Thr Val Ser Gly Leu Pro Lys Lys Gln
 65                  70                  75                  80

Cys Pro Cys Asp His Phe Lys Gly Asn Val Lys Lys Thr Arg His Gln
                 85                  90                  95

Arg His His Arg Lys Pro Asn Lys His Ser Arg Ala Cys Gln Gln Phe
                100                 105                 110

Leu Lys Gln Cys Gln Leu Arg Ser Phe Ala Leu Pro Leu
                115                 120                 125

<210> SEQ ID NO 12
<211> LENGTH: 119
```

<212> TYPE: PRT
<213> ORGANISM: Homo sapiens

<400> SEQUENCE: 12

```
Met Lys Val Leu Ile Ser Ser Leu Leu Leu Leu Pro Leu Met Leu
1               5                   10                  15

Met Ser Met Val Ser Ser Ser Leu Asn Pro Gly Val Ala Arg Gly His
                20                  25                  30

Arg Asp Arg Gly Gln Ala Ser Arg Arg Trp Leu Gln Glu Gly Gly Gln
            35                  40                  45

Glu Cys Glu Cys Lys Asp Trp Phe Leu Arg Ala Pro Arg Arg Lys Phe
50                  55                  60

Met Thr Val Ser Gly Leu Pro Lys Lys Gln Cys Pro Cys Asp His Phe
65                  70                  75                  80

Lys Gly Asn Val Lys Lys Thr Arg His Gln Arg His His Arg Lys Pro
                85                  90                  95

Asn Lys His Ser Arg Ala Cys Gln Gln Phe Leu Lys Gln Cys Gln Leu
            100                 105                 110

Arg Ser Phe Ala Leu Pro Leu
        115
```

<210> SEQ ID NO 13
<211> LENGTH: 1226
<212> TYPE: DNA
<213> ORGANISM: Mus musculus
<220> FEATURE:
<221> NAME/KEY: CDS
<222> LOCATION: (3)..(1220)

<400> SEQUENCE: 13

```
cc atg gca aaa ttt tgg aag aaa gca cta tta aca att gca gcc tta       47
   Met Ala Lys Phe Trp Lys Lys Ala Leu Leu Thr Ile Ala Ala Leu
   1               5                   10                  15 aca gtc ggc acc tcc gca gga att aca agc gtt tct gcc tac caa ctt      95
Thr Val Gly Thr Ser Ala Gly Ile Thr Ser Val Ser Ala Tyr Gln Leu
                20                  25                  30 atg tgt tac tac act tca tgg gct aaa gat cgt cca att gaa ggt tct     143
Met Cys Tyr Tyr Thr Ser Trp Ala Lys Asp Arg Pro Ile Glu Gly Ser
            35                  40                  45 ttt aag cca gga aat att gat cct tgt ctt tgt aca cat ctt att tac     191
Phe Lys Pro Gly Asn Ile Asp Pro Cys Leu Cys Thr His Leu Ile Tyr
        50                  55                  60 gct ttt gct ggt atg caa aat aat gaa att act tac aca cac gaa caa     239
Ala Phe Ala Gly Met Gln Asn Asn Glu Ile Thr Tyr Thr His Glu Gln
65                  70                  75 gat tta cgt gat tac gaa gct ctt aat ggt ctt aag gat aag aat act     287
Asp Leu Arg Asp Tyr Glu Ala Leu Asn Gly Leu Lys Asp Lys Asn Thr
80                  85                  90                  95 gaa ctt aag aca ctt ctt gca att ggt gga tgg aag ttt gga cca gct     335
Glu Leu Lys Thr Leu Leu Ala Ile Gly Gly Trp Lys Phe Gly Pro Ala
                100                 105                 110 cct ttt agt gca atg gtt tca act cca caa aat cgg caa att ttt att     383
Pro Phe Ser Ala Met Val Ser Thr Pro Gln Asn Arg Gln Ile Phe Ile
            115                 120                 125 caa agt gta att cgg ttt tta cgg caa tac aat ttt gat gga ctt aat     431
Gln Ser Val Ile Arg Phe Leu Arg Gln Tyr Asn Phe Asp Gly Leu Asn
        130                 135                 140 ctt gat tgg caa tac cca ggt agt cga gga tca cca cct aag gat aag     479
Leu Asp Trp Gln Tyr Pro Gly Ser Arg Gly Ser Pro Pro Lys Asp Lys
    145                 150                 155
```

```
cat tta ttt agt gtt ctt gta aaa gaa atg cga aag gct ttt gaa gaa      527
His Leu Phe Ser Val Leu Val Lys Glu Met Arg Lys Ala Phe Glu Glu
160                 165                 170                 175 gaa agt gtt gaa aag gat att cca cgt ctt ctt ctt act agt aca ggt      575
Glu Ser Val Glu Lys Asp Ile Pro Arg Leu Leu Leu Thr Ser Thr Gly
                180                 185                 190 gca gga att att gat gta att aag tca ggt tac aag att cca gaa ctt      623
Ala Gly Ile Ile Asp Val Ile Lys Ser Gly Tyr Lys Ile Pro Glu Leu
            195                 200                 205 agt caa tca ctt gat tac att caa gtt atg act tac gat tta cac gat      671
Ser Gln Ser Leu Asp Tyr Ile Gln Val Met Thr Tyr Asp Leu His Asp
        210                 215                 220 cct aag gat ggt tac aca gga gaa aat tct cca ctt tac aag agt cct      719
Pro Lys Asp Gly Tyr Thr Gly Glu Asn Ser Pro Leu Tyr Lys Ser Pro
    225                 230                 235 tac gat att gga aag agt gct gat ctt aat gtt gat tct att att agt      767
Tyr Asp Ile Gly Lys Ser Ala Asp Leu Asn Val Asp Ser Ile Ile Ser
240                 245                 250                 255 tac tgg aaa gat cat gga gct gca tca gaa aag ctt att gtt ggt ttt      815
Tyr Trp Lys Asp His Gly Ala Ala Ser Glu Lys Leu Ile Val Gly Phe
                260                 265                 270 cca gct tac gga cac act ttt att ctt tca gat cca tct aag aca ggt      863
Pro Ala Tyr Gly His Thr Phe Ile Leu Ser Asp Pro Ser Lys Thr Gly
            275                 280                 285 att gga gca cct act att tct aca ggt cca cct gga aag tat act gat      911
Ile Gly Ala Pro Thr Ile Ser Thr Gly Pro Pro Gly Lys Tyr Thr Asp
        290                 295                 300 gaa agt ggt ctt tta gct tac tac gaa gtt tgt aca ttt tta aat gaa      959
Glu Ser Gly Leu Leu Ala Tyr Tyr Glu Val Cys Thr Phe Leu Asn Glu
    305                 310                 315 gga gct aca gaa gtt tgg gat gca cca caa gaa gta cct tat gca tac     1007
Gly Ala Thr Glu Val Trp Asp Ala Pro Gln Glu Val Pro Tyr Ala Tyr
320                 325                 330                 335 cag ggt aat gaa tgg gtt gga tac gat aat gta cgt agt ttt aag ctt     1055
Gln Gly Asn Glu Trp Val Gly Tyr Asp Asn Val Arg Ser Phe Lys Leu
                340                 345                 350 aag gct caa tgg ctt aag gat aat aat tta ggt gga gca gtt gta tgg     1103
Lys Ala Gln Trp Leu Lys Asp Asn Asn Leu Gly Gly Ala Val Val Trp
            355                 360                 365 cca ctt gat atg gat gat ttt tct ggt agt ttt tgt cat caa cgg cac     1151
Pro Leu Asp Met Asp Asp Phe Ser Gly Ser Phe Cys His Gln Arg His
        370                 375                 380 ttt cct ctt act tca aca ctt aag ggt gat ctt aat att cat tca gca     1199
Phe Pro Leu Thr Ser Thr Leu Lys Gly Asp Leu Asn Ile His Ser Ala
    385                 390                 395 tct tgt aag gga cca tat taa ctcgag                                   1226
Ser Cys Lys Gly Pro Tyr
400                 405

<210> SEQ ID NO 14
<211> LENGTH: 405
<212> TYPE: PRT
<213> ORGANISM: Mus musculus

<400> SEQUENCE: 14

Met Ala Lys Phe Trp Lys Lys Ala Leu Leu Thr Ile Ala Ala Leu Thr
1               5                   10                  15

Val Gly Thr Ser Ala Gly Ile Thr Ser Val Ser Ala Tyr Gln Leu Met
                20                  25                  30
```

Cys Tyr Tyr Thr Ser Trp Ala Lys Asp Arg Pro Ile Glu Gly Ser Phe
                35                  40                  45

Lys Pro Gly Asn Ile Asp Pro Cys Leu Cys Thr His Leu Ile Tyr Ala
 50                  55                  60

Phe Ala Gly Met Gln Asn Asn Glu Ile Thr Tyr Thr His Glu Gln Asp
 65                  70                  75                  80

Leu Arg Asp Tyr Glu Ala Leu Asn Gly Leu Lys Asp Lys Asn Thr Glu
                 85                  90                  95

Leu Lys Thr Leu Leu Ala Ile Gly Gly Trp Lys Phe Gly Pro Ala Pro
                100                 105                 110

Phe Ser Ala Met Val Ser Thr Pro Gln Asn Arg Gln Ile Phe Ile Gln
                115                 120                 125

Ser Val Ile Arg Phe Leu Arg Gln Tyr Asn Phe Asp Gly Leu Asn Leu
130                 135                 140

Asp Trp Gln Tyr Pro Gly Ser Arg Gly Ser Pro Pro Lys Asp Lys His
145                 150                 155                 160

Leu Phe Ser Val Leu Val Lys Glu Met Arg Lys Ala Phe Glu Glu Glu
                165                 170                 175

Ser Val Glu Lys Asp Ile Pro Arg Leu Leu Leu Thr Ser Thr Gly Ala
                180                 185                 190

Gly Ile Ile Asp Val Ile Lys Ser Gly Tyr Lys Ile Pro Glu Leu Ser
                195                 200                 205

Gln Ser Leu Asp Tyr Ile Gln Val Met Thr Tyr Asp Leu His Asp Pro
                210                 215                 220

Lys Asp Gly Tyr Thr Gly Glu Asn Ser Pro Leu Tyr Lys Ser Pro Tyr
225                 230                 235                 240

Asp Ile Gly Lys Ser Ala Asp Leu Asn Val Asp Ser Ile Ile Ser Tyr
                245                 250                 255

Trp Lys Asp His Gly Ala Ala Ser Glu Lys Leu Ile Val Gly Phe Pro
                260                 265                 270

Ala Tyr Gly His Thr Phe Ile Leu Ser Asp Pro Ser Lys Thr Gly Ile
                275                 280                 285

Gly Ala Pro Thr Ile Ser Thr Gly Pro Pro Gly Lys Tyr Thr Asp Glu
290                 295                 300

Ser Gly Leu Leu Ala Tyr Tyr Glu Val Cys Thr Phe Leu Asn Glu Gly
305                 310                 315                 320

Ala Thr Glu Val Trp Asp Ala Pro Gln Glu Val Pro Tyr Ala Tyr Gln
                325                 330                 335

Gly Asn Glu Trp Val Gly Tyr Asp Asn Val Arg Ser Phe Lys Leu Lys
                340                 345                 350

Ala Gln Trp Leu Lys Asp Asn Asn Leu Gly Gly Ala Val Val Trp Pro
                355                 360                 365

Leu Asp Met Asp Asp Phe Ser Gly Ser Phe Cys His Gln Arg His Phe
370                 375                 380

Pro Leu Thr Ser Thr Leu Lys Gly Asp Leu Asn Ile His Ser Ala Ser
385                 390                 395                 400

Cys Lys Gly Pro Tyr
                405

<210> SEQ ID NO 15
<211> LENGTH: 398
<212> TYPE: PRT
<213> ORGANISM: Mus musculus

<400> SEQUENCE: 15

```
Met Ala Lys Leu Ile Leu Val Thr Gly Leu Ala Ile Leu Leu Asn Val
1               5                   10                  15

Gln Leu Gly Ser Ser Tyr Gln Leu Met Cys Tyr Tyr Thr Ser Trp Ala
            20                  25                  30

Lys Asp Arg Pro Ile Glu Gly Ser Phe Lys Pro Gly Asn Ile Asp Pro
            35                  40                  45

Cys Leu Cys Thr His Leu Ile Tyr Ala Phe Ala Gly Met Gln Asn Asn
            50                  55                  60

Glu Ile Thr Tyr Thr His Glu Gln Asp Leu Arg Asp Tyr Glu Ala Leu
65                  70                  75                  80

Asn Gly Leu Lys Asp Lys Asn Thr Glu Leu Lys Thr Leu Leu Ala Ile
                85                  90                  95

Gly Gly Trp Lys Phe Gly Pro Ala Pro Phe Ser Ala Met Val Ser Thr
                100                 105                 110

Pro Gln Asn Arg Gln Ile Phe Ile Gln Ser Val Ile Arg Phe Leu Arg
            115                 120                 125

Gln Tyr Asn Phe Asp Gly Leu Asn Leu Asp Trp Gln Tyr Pro Gly Ser
            130                 135                 140

Arg Gly Ser Pro Pro Lys Asp Lys His Leu Phe Ser Val Leu Val Lys
145                 150                 155                 160

Glu Met Arg Lys Ala Phe Glu Glu Ser Val Glu Lys Asp Ile Pro
                165                 170                 175

Arg Leu Leu Leu Thr Ser Thr Gly Ala Gly Ile Ile Asp Val Ile Lys
                180                 185                 190

Ser Gly Tyr Lys Ile Pro Glu Leu Ser Gln Ser Leu Asp Tyr Ile Gln
                195                 200                 205

Val Met Thr Tyr Asp Leu His Asp Pro Lys Asp Gly Tyr Thr Gly Glu
210                 215                 220

Asn Ser Pro Leu Tyr Lys Ser Pro Tyr Asp Ile Gly Lys Ser Ala Asp
225                 230                 235                 240

Leu Asn Val Asp Ser Ile Ile Ser Tyr Trp Lys Asp His Gly Ala Ala
                245                 250                 255

Ser Glu Lys Leu Ile Val Gly Phe Pro Ala Tyr Gly His Thr Phe Ile
                260                 265                 270

Leu Ser Asp Pro Ser Lys Thr Gly Ile Gly Ala Pro Thr Ile Ser Thr
                275                 280                 285

Gly Pro Pro Gly Lys Tyr Thr Asp Glu Ser Gly Leu Leu Ala Tyr Tyr
                290                 295                 300

Glu Val Cys Thr Phe Leu Asn Glu Gly Ala Thr Glu Val Trp Asp Ala
305                 310                 315                 320

Pro Gln Glu Val Pro Tyr Ala Tyr Gln Gly Asn Glu Trp Val Gly Tyr
                325                 330                 335

Asp Asn Val Arg Ser Phe Lys Leu Lys Ala Gln Trp Leu Lys Asp Asn
                340                 345                 350

Asn Leu Gly Gly Ala Val Val Trp Pro Leu Asp Met Asp Asp Phe Ser
                355                 360                 365

Gly Ser Phe Cys His Gln Arg His Phe Pro Leu Thr Ser Thr Leu Lys
                370                 375                 380

Gly Asp Leu Asn Ile His Ser Ala Ser Cys Lys Gly Pro Tyr
385                 390                 395

<210> SEQ ID NO 16
<211> LENGTH: 1181
```

```
<212> TYPE: DNA
<213> ORGANISM: Homo sapiens
<220> FEATURE:
<221> NAME/KEY: CDS
<222> LOCATION: (3)..(1175)

<400> SEQUENCE: 16 cc atg gca aaa ttt tgg aag aaa gca cta tta aca att gca gcc tta        47
   Met Ala Lys Phe Trp Lys Lys Ala Leu Leu Thr Ile Ala Ala Leu
   1               5                  10                  15 aca gtc ggc acc tcc gca gga att aca agc gtt tct gcc tac aag ctt       95
Thr Val Gly Thr Ser Ala Gly Ile Thr Ser Val Ser Ala Tyr Lys Leu
                 20                  25                  30 gtt tgt tac tac act tca tgg tct caa tac cga gaa ggt gat gga agt      143
Val Cys Tyr Tyr Thr Ser Trp Ser Gln Tyr Arg Glu Gly Asp Gly Ser
             35                  40                  45 tgt ttt cca gat gct ctt gat cgg ttt tta tgt aca cat att att tac      191
Cys Phe Pro Asp Ala Leu Asp Arg Phe Leu Cys Thr His Ile Ile Tyr
         50                  55                  60 tct ttt gca aat att agt aat gat cac att gat aca tgg gaa tgg aat      239
Ser Phe Ala Asn Ile Ser Asn Asp His Ile Asp Thr Trp Glu Trp Asn
 65                  70                  75 gat gtt act ctt tac ggt atg ctt aat aca ctt aag aat cgt aat cca      287
Asp Val Thr Leu Tyr Gly Met Leu Asn Thr Leu Lys Asn Arg Asn Pro
 80                  85                  90                  95 aat tta aag act tta ctt agt gta ggt gga tgg aat ttt ggt tct caa      335
Asn Leu Lys Thr Leu Leu Ser Val Gly Gly Trp Asn Phe Gly Ser Gln
                100                 105                 110 cgg ttt agt aag att gct tca aat act caa tct cgt cgg aca ttt att      383
Arg Phe Ser Lys Ile Ala Ser Asn Thr Gln Ser Arg Arg Thr Phe Ile
            115                 120                 125 aaa agt gtt cca cca ttt tta cgt act cat ggt ttt gat gga ctt gat      431
Lys Ser Val Pro Pro Phe Leu Arg Thr His Gly Phe Asp Gly Leu Asp
        130                 135                 140 tta gca tgg ctt tat cca ggt cga cgt gat aag caa cac ttt act aca      479
Leu Ala Trp Leu Tyr Pro Gly Arg Arg Asp Lys Gln His Phe Thr Thr
    145                 150                 155 ctt att aaa gaa atg aag gct gaa ttt att aag gaa gca caa cct ggt      527
Leu Ile Lys Glu Met Lys Ala Glu Phe Ile Lys Glu Ala Gln Pro Gly
160                 165                 170                 175 aaa aag caa ctt ctt ctt agt gct gca tta tca gct gga aag gtt act      575
Lys Lys Gln Leu Leu Leu Ser Ala Ala Leu Ser Ala Gly Lys Val Thr
                180                 185                 190 att gat agt tca tac gat att gca aag att agt caa cat ctt gat ttt      623
Ile Asp Ser Ser Tyr Asp Ile Ala Lys Ile Ser Gln His Leu Asp Phe
            195                 200                 205 att tca att atg aca tac gat ttt cac ggt gct tgg cgg ggt act aca      671
Ile Ser Ile Met Thr Tyr Asp Phe His Gly Ala Trp Arg Gly Thr Thr
        210                 215                 220 gga cat cac agt cca tta ttt cgt gga caa gaa gat gct tca cct gat      719
Gly His His Ser Pro Leu Phe Arg Gly Gln Glu Asp Ala Ser Pro Asp
    225                 230                 235 cgg ttt tct aat act gat tat gca gtt ggt tac atg ctt cgg tta gga      767
Arg Phe Ser Asn Thr Asp Tyr Ala Val Gly Tyr Met Leu Arg Leu Gly
240                 245                 250                 255 gct cca gca tct aaa ctt gta atg ggt att cct act ttt gga cga tca      815
Ala Pro Ala Ser Lys Leu Val Met Gly Ile Pro Thr Phe Gly Arg Ser
                260                 265                 270 ttt aca tta gct tct agt gaa act ggt gtt gga gca cca att tca ggt      863
Phe Thr Leu Ala Ser Ser Glu Thr Gly Val Gly Ala Pro Ile Ser Gly
            275                 280                 285
```

```
cca gga att cct ggt cgt ttt act aag gaa gct gga aca ctt gca tac      911
Pro Gly Ile Pro Gly Arg Phe Thr Lys Glu Ala Gly Thr Leu Ala Tyr
            290                 295                 300 tac gaa att tgt gat ttt ctt cgg ggt gct act gtt cat cga aca ctt      959
Tyr Glu Ile Cys Asp Phe Leu Arg Gly Ala Thr Val His Arg Thr Leu
305                 310                 315 gga caa caa gta cct tat gca act aaa ggt aat caa tgg gtt gga tac     1007
Gly Gln Gln Val Pro Tyr Ala Thr Lys Gly Asn Gln Trp Val Gly Tyr
320                 325                 330                 335 gat gat caa gaa agt gtt aag tca aag gta caa tac ctt aag gat cga     1055
Asp Asp Gln Glu Ser Val Lys Ser Lys Val Gln Tyr Leu Lys Asp Arg
                340                 345                 350 caa tta gct ggt gca atg gta tgg gct ctt gat ctt gat gat ttt caa     1103
Gln Leu Ala Gly Ala Met Val Trp Ala Leu Asp Leu Asp Asp Phe Gln
            355                 360                 365 ggt agt ttt tgt gga caa gat ctt cgt ttt cca ctt act aat gct att     1151
Gly Ser Phe Cys Gly Gln Asp Leu Arg Phe Pro Leu Thr Asn Ala Ile
        370                 375                 380 aag gat gca tta gct gca aca taa ctcgag                              1181
Lys Asp Ala Leu Ala Ala Thr
        385                 390

<210> SEQ ID NO 17
<211> LENGTH: 390
<212> TYPE: PRT
<213> ORGANISM: Homo sapiens

<400> SEQUENCE: 17

Met Ala Lys Phe Trp Lys Lys Ala Leu Leu Thr Ile Ala Ala Leu Thr
1               5                   10                  15

Val Gly Thr Ser Ala Gly Ile Thr Ser Val Ser Ala Tyr Lys Leu Val
            20                  25                  30

Cys Tyr Tyr Thr Ser Trp Ser Gln Tyr Arg Glu Gly Asp Gly Ser Cys
        35                  40                  45

Phe Pro Asp Ala Leu Asp Arg Phe Leu Cys Thr His Ile Ile Tyr Ser
    50                  55                  60

Phe Ala Asn Ile Ser Asn Asp His Ile Asp Thr Trp Glu Trp Asn Asp
65                  70                  75                  80

Val Thr Leu Tyr Gly Met Leu Asn Thr Leu Lys Asn Arg Asn Pro Asn
                85                  90                  95

Leu Lys Thr Leu Leu Ser Val Gly Gly Trp Asn Phe Gly Ser Gln Arg
            100                 105                 110

Phe Ser Lys Ile Ala Ser Asn Thr Gln Ser Arg Arg Thr Phe Ile Lys
        115                 120                 125

Ser Val Pro Pro Phe Leu Arg Thr His Gly Phe Asp Gly Leu Asp Leu
    130                 135                 140

Ala Trp Leu Tyr Pro Gly Arg Arg Asp Lys Gln His Phe Thr Thr Leu
145                 150                 155                 160

Ile Lys Glu Met Lys Ala Glu Phe Ile Lys Glu Ala Gln Pro Gly Lys
                165                 170                 175

Lys Gln Leu Leu Leu Ser Ala Ala Leu Ser Ala Gly Lys Val Thr Ile
            180                 185                 190

Asp Ser Ser Tyr Asp Ile Ala Lys Ile Ser Gln His Leu Asp Phe Ile
        195                 200                 205

Ser Ile Met Thr Tyr Asp Phe His Gly Ala Trp Arg Gly Thr Thr Gly
    210                 215                 220
```

-continued

His His Ser Pro Leu Phe Arg Gly Gln Glu Asp Ala Ser Pro Asp Arg
225                 230                 235                 240

Phe Ser Asn Thr Asp Tyr Ala Val Gly Tyr Met Leu Arg Leu Gly Ala
            245                 250                 255

Pro Ala Ser Lys Leu Val Met Gly Ile Pro Thr Phe Gly Arg Ser Phe
        260                 265                 270

Thr Leu Ala Ser Ser Glu Thr Gly Val Gly Ala Pro Ile Ser Gly Pro
    275                 280                 285

Gly Ile Pro Gly Arg Phe Thr Lys Glu Ala Gly Thr Leu Ala Tyr Tyr
290                 295                 300

Glu Ile Cys Asp Phe Leu Arg Gly Ala Thr Val His Arg Thr Leu Gly
305                 310                 315                 320

Gln Gln Val Pro Tyr Ala Thr Lys Gly Asn Gln Trp Val Gly Tyr Asp
                325                 330                 335

Asp Gln Glu Ser Val Lys Ser Lys Val Gln Tyr Leu Lys Asp Arg Gln
            340                 345                 350

Leu Ala Gly Ala Met Val Trp Ala Leu Asp Leu Asp Asp Phe Gln Gly
        355                 360                 365

Ser Phe Cys Gly Gln Asp Leu Arg Phe Pro Leu Thr Asn Ala Ile Lys
    370                 375                 380

Asp Ala Leu Ala Ala Thr
385                 390

<210> SEQ ID NO 18
<211> LENGTH: 383
<212> TYPE: PRT
<213> ORGANISM: Homo sapiens

<400> SEQUENCE: 18

Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
            20                  25                  30

Gln Tyr Arg Glu Gly Asp Gly Ser Cys Phe Pro Asp Ala Leu Asp Arg
        35                  40                  45

Phe Leu Cys Thr His Ile Ile Tyr Ser Phe Ala Asn Ile Ser Asn Asp
    50                  55                  60

His Ile Asp Thr Trp Glu Trp Asn Asp Val Thr Leu Tyr Gly Met Leu
65                  70                  75                  80

Asn Thr Leu Lys Asn Arg Asn Pro Asn Leu Lys Thr Leu Leu Ser Val
                85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
        115                 120                 125

Thr His Gly Phe Asp Gly Leu Asp Leu Ala Trp Leu Tyr Pro Gly Arg
    130                 135                 140

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
        195                 200                 205

His Gly Ala Trp Arg Gly Thr Thr Gly His His Ser Pro Leu Phe Arg
    210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
                245                 250                 255

Gly Ile Pro Thr Phe Gly Arg Ser Phe Thr Leu Ala Ser Ser Glu Thr
            260                 265                 270

Gly Val Gly Ala Pro Ile Ser Gly Pro Gly Ile Pro Gly Arg Phe Thr
        275                 280                 285

Lys Glu Ala Gly Thr Leu Ala Tyr Tyr Glu Ile Cys Asp Phe Leu Arg
    290                 295                 300

Gly Ala Thr Val His Arg Thr Leu Gly Gln Gln Val Pro Tyr Ala Thr
305                 310                 315                 320

Lys Gly Asn Gln Trp Val Gly Tyr Asp Asp Gln Glu Ser Val Lys Ser
                325                 330                 335

Lys Val Gln Tyr Leu Lys Asp Arg Gln Leu Ala Gly Ala Met Val Trp
            340                 345                 350

Ala Leu Asp Leu Asp Asp Phe Gln Gly Ser Phe Cys Gly Gln Asp Leu
        355                 360                 365

Arg Phe Pro Leu Thr Asn Ala Ile Lys Asp Ala Leu Ala Ala Thr
    370                 375                 380

<210> SEQ ID NO 19
<211> LENGTH: 20
<212> TYPE: PRT
<213> ORGANISM: Lactobacillus

<400> SEQUENCE: 19

Met Ala Gly Asn Ser Ser Asn Phe Ile His Lys Ile Ile Lys Gln Ile
1               5                   10                  15

Phe Thr His Arg
            20

<210> SEQ ID NO 20
<211> LENGTH: 7673
<212> TYPE: DNA
<213> ORGANISM: artificial
<220> FEATURE:
<223> OTHER INFORMATION: Recombinant plasmid
<220> FEATURE:
<221> NAME/KEY: CDS
<222> LOCATION: (5853)..(7658)

<400> SEQUENCE: 20
gaattcggta ccccgggttc gaaggcgcca agcttcaaat tacagcacgt gttgctttga      60
ttgatagcca aaaagcagca gttgataaag caattactga tattgctgaa aaattgtaat     120
ttataaataa aaatcacctt ttagaggtgg tttttttatt tataaattat tcgtttgatt     180
tcgctttcga tagaacaatc aaagcgagaa taaggaagat aaatcccata agggcgggag     240
cagaatgtcc gagactaatt catgagatcg attttttatt aaaacgtctc aaaatcgttt     300
ctgagacgtt ttagcgttta tttcgtttag ttatcggcat aatcgttaaa acaggcgtta     360
tcgtagcgta aaagcccttg agcgtagcgt gctttgcagc gaagatgttg tctgttagat     420
tatgaaagcc gatgactgaa tgaataata agcgcagcgt ccttctattt cggttggagg     480
aggctcaagg gagtttgagg gaatgaaatt ccctcatggg tttgatttta aaaattgctt     540

```
gcaattttgc cgagcggtag cgctggaaaa attttttgaaa aaaatttgga atttggaaaa      600
aaatggggggg aaaggaagcg aatttttgctt ccgtactacg acccccccatt aagtgccgag    660
tgccaatttt tgtgccaaaa acgctctatc ccaactggct caagggtttg aggggttttt       720
caatcgccaa cgaatcgcca acgttttcgc caacgttttt tataaatcta tatttaagta       780
gctttattgt tgtttttatg attacaaagt gatacactaa ttttataaaa ttatttgatt       840
ggagtttttt aaatggtgat ttcagaatcg aaaaaaagag ttatgatttc tctgacaaaa       900
gagcaagata aaaaattaac agatatggcg aaacaaaaag gttttttcaaa atctgcggtt     960
gcggcgttag ctatagaaga atatgcaaga aaggaatcag aataaaaaaa ataagcgaaa      1020
gctcgcgttt ttagaaggat acgagttttc gctacttgtt tttgataagg taatatatca      1080
tggctattaa atactaaagc tagaaatttt ggattttttat tatatcctga ctcaattcct     1140
aatgattgga agaaaaatt agagagtttg gcgtatctta tggctgtcag tcctttacac       1200
gatatggacg aaaaaaaga taaagataca tggaatagta gtgatgttat acgaaatgga       1260
aagcactata aaaaaccaca ctatcacgtt atatatattg cacgaaatcc tgtaacaata      1320
gaaagcgtta ggaacaagat taagcgaaaa ttggggaata gttcagttgc tcatgttgag     1380
atacttgatt atatcaaagg ttcatatgaa tatttgactc atgaatcaaa ggacgctatt      1440
gctaagaata acatatata cgacaaaaaa gatattttga acattaatga ttttgatatt       1500
gaccgctata taacacttga tgaaagccaa aaaagagaat tgaagaattt acttttagat      1560
atagtggatg actataattt ggtaaataca aaagatttaa tggcttttat tcgccttagg     1620
ggagcggagt ttggaatttt aaatacgaat gatgtaaaag atattgtttc aacaaactct     1680
agcgccttta gattatggtt tgagggcaat tatcagtgtg gatatagagc aagttatgca     1740
aaggttcttg atgctgaaac ggggggaaata aaatgacaaa caagagaaaaa gagttatttg   1800
ctgaaaatga ggaattaaaa aaagaaatta aggacttaaa agagcgtatt gaaagataca     1860
gagaaatgga agttgaatta agtacaacaa tagatttatt gagaggaggg attattgaat     1920
aaataaaagc cccccctgacg aaagtcgaag ggggcttta ttttggttttg atgttgcgat    1980
taatagcaat acgattgcaa taaacaaaat gatcccctta gaagcaaact taagagtgtg    2040
ttgatagtgc attatcttaa aatttttgtat aataggaatt gaagttaaat tagatgctaa    2100
aaataggaat tgaagttaaa ttagatgcta aaaatttgta attaagaagg agggattcgt     2160
catgttggta ttccaaatgc gtaatgtaga taaaacatct actgttttga aacagactaa     2220
aaacagtgat tacgcagata aataaatacg ttagattaat tcctaccagt gactaatctt     2280
atgactttt aaacagataa ctaaaattac aaacaaatcg tttaacttca ggagagatta      2340
catgaacaaa aatataaata tctcaaactt tttaacgagt gaaaaagtac tcaaccaaat     2400
aataaaacaa ttgaatttaa agaaaccga taccgtttac gaaattggaa caggtaaagg     2460
gcatttaacg acgaaactgg ctaaaataag taaacaggta acgtctattg aattagacag     2520
tcatctattc aacttatcgt cagaaaaatt aaaactgaat actcgtgtca ctttaattca     2580
ccaagatatt ctacagtttc aattccctaa caaacagagg tataaaattg ttgggaatat     2640
tccttacaat ttaagcacac aaattattaa aaaagtggtt tttgaaagcc gtgcgtctga    2700
catctatctg actgttgaag aaggattcta caagcgtacc ttggatattc accgaacact     2760
aggggttgctc ttgcacactc aagtctcgat tcagcaattg cttaagctgc cagcggaatg    2820
cttttcatcct aaaccaaaag taaacagtgt cttaataaaa cttacccgcc ataccacaga    2880
tgttccagat aaatattgga agctatataa gtactttgtt tcaaaatggg tcaatcgaga     2940
```

```
atatcgtcaa ctgtttacta aaaatcagtt tcgtcaagca atgaaacacg ccaaagtaaa    3000
caatttaagt accattactt atgagcaagt attgtctatt tttaatagtt atctattatt    3060
taacgggagg aaataattct atgagtcgct tttttaaatt tggaaagtta cacgttacta    3120
aagggaatgg agaccggggt cgacccttca atagagttct taacgttaat ccgaaaaaaa    3180
ctaacgttaa tattaaaaaa taagatccgc ttgtgaatta tgtataattt gattagacta    3240
aagaatagga gaaagtatga tgatatttaa aaaactttct cgttaagata ggttgttggt    3300
gagcatgtta tatacggatg tatcggtttc cttaatgcaa aattttgttg ctatcttatt    3360 aattttcta ttatatagat atattcaaag aaagataaca tttaaacgga tcatattaga    3420
tattttaata gcgattattt tttcaatatt atatctgttt atttcagatg cgtcattact    3480
tgtaatggta ttaatgcgat tagggtggca ttttcatcaa caaaaagaaa ataagataaa    3540
aacgactgat acagctaatt taattctaat tatcgtgatc cagttattgt tagttgcggt    3600
tgggactatt attagtcagt ttaccatatc gattatcaaa agtgatttca gccaaaatat    3660
attgaacaat agtgcaacag ataaactttt attaggtatt ttctttgctg ttttatttga    3720
cggcttgttc tttatattat tgaagaataa gcggactgaa ttacaacatt taaatcaaga    3780
aatcattgaa ttttcgttag aaaaacaata ttttatattt atatttattt tatttatagt    3840
aatagaaatt attttagcag ttgggaatct tcaaggagta acagccacga tattattaac    3900
cattatcatt attttttgtg tccttatcgg gatgactttt tggcaagtga tgcttttttt    3960
gaaggcttat tcgattcgcc aagaagccaa tgaccaattg gtccggaatc aacaacttca    4020
agattatcta gtcaatatcg aacagcagta caccgaatta cggcgattta agcatgatta    4080
tcaaaacatc ttattatcgt tggagagttt tgccgaaaag ggcgatcagc aacagtttaa    4140
ggcgtattac caagaattat tagcacaacg gccaattcaa agtgaaatcc aaggggcagt    4200
cattgcacaa ctcgactact tgaaaaatga tcctattcga ggattagtca ttcaaaagtt    4260
tttggcagcc aaacaggctg tgttactttt aaaattcgaa atgaccgaac caatcgaatt    4320
agcaaccgct aatctattaa cggttattcg gattatcggt attttattag acaatgcgat    4380
tgaacaagcc gttcaagaaa ccgatcaatt ggtgagttgt gctttcttac aatctgatgg    4440
tttaatcgaa attacgattg aaaatacggc cagtcaagtt aagaatctcc aagcattttc    4500
agagttaggc tattcaacga aaggcgctgg tcggggggact ggtttagcta atgtgcagga    4560
tttgattgcc aaacaaacca atttattctt agaaacacag attgaaaata gaaagttacg    4620
acagacattg atgattacgg aggaaactta atttgtatcc cgtttattta ttagaggatg    4680
atttacagca acaagcgatt tatcagcaaa ttatcgcgaa tacgattatg attaacgaat    4740
ttgcaatgac tttaacatgc gctgccagtg atactgagac attgttggcg gcaattaagg    4800
atcagcaacg aggtttattc tttttggata tggaaattga ggataaccgc caagccggtt    4860
tagaagtggc aactaagatt cggcagatga tgccgtttgc gcaaattgtc ttcattacaa    4920
cccacgagga actgacatta ttaacgttag aacgaaaaat agcgccttta gattacattc    4980
tcaaggacca aacaatggct gaaatcaaaa ggcaattgat tgatgatcta ttgttagctg    5040
agaagcaaaa cgaggcggca gcgtatcacc gagaaaattt atttagttat aaaataggtc    5100
ctcgcttttt ctcattacca ttaaaggaag ttgtttattt atatactgaa aaagaaaatc    5160
cgggtcatat taatttgtta gccgttacca gaaaggttac ttttccagga aatttaaatg    5220
cgctggaagc ccaatatcca atgctctttc ggtgtgataa aagttactta gttaacctat    5280
```

-continued

```
ctaatattgc caattatgac agtaaaacac ggagtttaaa atttgtagat ggcagtgagg   5340
caaaagtctc gttccggaaa tcacgggaac tagtggccaa attaaaacaa atgatgtagc   5400
gcctgcaggc acgccaaatg atcccagtaa aaagccaccc gcatggcggg tggctttta    5460 ttagccctag aagggcttcc cacacgcatt tcagcgcctt agtgccttag tttgtgaatc   5520
ataggtggta tagtcccgaa atacccgtct aaggaattgt cagataggcc taatgactgg   5580
cttttataat atgagataat gccgactgta cttttacag tcggttttct aatgtcacta    5640
acctgccccg ttagttgaag aaggttttta tattacagct ccagatctac cggtttaatt   5700
tgaaaattga tattagcgtt taacagttaa attaatacgt taataatttt tttgtcttta   5760
aatagggatt tgaagcataa tggtgttata gcgtacttag ctggccagca tatatgtatt   5820
ctataaaata ctattacaag gagatttag cc atg gta cgt cct gta gaa acc      5873
                                    Met Val Arg Pro Val Glu Thr
                                    1               5
```

```
cca acc cgt gaa atc aaa aaa ctc gac ggc ctg tgg gca ttc agt ctg     5921
Pro Thr Arg Glu Ile Lys Lys Leu Asp Gly Leu Trp Ala Phe Ser Leu
        10              15                  20 gat cgc gaa aac tgt gga att gat cag cgt tgg tgg gaa agc gcg tta     5969
Asp Arg Glu Asn Cys Gly Ile Asp Gln Arg Trp Trp Glu Ser Ala Leu
    25                  30                  35 caa gaa agc cgg gca att gct gtg cca ggc agt ttt aac gat cag ttc     6017
Gln Glu Ser Arg Ala Ile Ala Val Pro Gly Ser Phe Asn Asp Gln Phe
40              45                  50                  55 gcc gat gca gat att cgt aat tat gcg ggc aac gtc tgg tat cag cgc     6065
Ala Asp Ala Asp Ile Arg Asn Tyr Ala Gly Asn Val Trp Tyr Gln Arg
                60                  65                  70 gaa gtc ttt ata ccg aaa ggt tgg gca ggc cag cgt atc gtg ctg cgt     6113
Glu Val Phe Ile Pro Lys Gly Trp Ala Gly Gln Arg Ile Val Leu Arg
            75                  80                  85 ttc gat gcg gtc act cat tac ggc aaa gtg tgg gtc aat aat cag gaa     6161
Phe Asp Ala Val Thr His Tyr Gly Lys Val Trp Val Asn Asn Gln Glu
        90                  95                  100 gtg atg gag cat cag ggc ggc tat acg cca ttt gaa gcc gat gtc acg     6209
Val Met Glu His Gln Gly Gly Tyr Thr Pro Phe Glu Ala Asp Val Thr
    105                 110                 115 ccg tat gtt att gcc ggg aaa agt gta cgt atc acc gtt tgt gtg aac     6257
Pro Tyr Val Ile Ala Gly Lys Ser Val Arg Ile Thr Val Cys Val Asn
120             125                 130                 135 aac gaa ctg aac tgg cag act atc ccg ccg gga atg gtg att acc gac     6305
Asn Glu Leu Asn Trp Gln Thr Ile Pro Pro Gly Met Val Ile Thr Asp
                140                 145                 150 gaa aac ggc aag aaa aag cag tct tac ttc cat gat ttc ttt aac tat     6353
Glu Asn Gly Lys Lys Lys Gln Ser Tyr Phe His Asp Phe Phe Asn Tyr
            155                 160                 165 gcc gga atc cat cgc agc gta atg ctc tac acc acg ccg aac acc tgg     6401
Ala Gly Ile His Arg Ser Val Met Leu Tyr Thr Thr Pro Asn Thr Trp
        170                 175                 180 gtg gac gat atc acc gtg gtg acg cat gtc gcg caa gac tgt aac cac     6449
Val Asp Asp Ile Thr Val Val Thr His Val Ala Gln Asp Cys Asn His
    185                 190                 195 gcg tct gtt gac tgg cag gtg gtg gcc aat ggt gat gtc agc gtt gaa     6497
Ala Ser Val Asp Trp Gln Val Val Ala Asn Gly Asp Val Ser Val Glu
200             205                 210                 215 ctg cgt gat gcg gat caa cag gtg gtt gca act gga caa ggc act agc     6545
Leu Arg Asp Ala Asp Gln Gln Val Val Ala Thr Gly Gln Gly Thr Ser
                220                 225                 230 ggg act ttg caa gtg gtg aat ccg cac ctc tgg caa ccg ggt gaa ggt     6593
```

-continued

```
Gly Thr Leu Gln Val Val Asn Pro His Leu Trp Gln Pro Gly Glu Gly
                235                 240                 245 tat ctc tat gaa ctg tgc gtc aca gcc aaa agc cag aca gag tgt gat    6641
Tyr Leu Tyr Glu Leu Cys Val Thr Ala Lys Ser Gln Thr Glu Cys Asp
        250                 255                 260 atc tac ccg ctt cgc gtc ggc atc cgg tca gtg gca gtg aag ggc gaa    6689
Ile Tyr Pro Leu Arg Val Gly Ile Arg Ser Val Ala Val Lys Gly Glu
265                 270                 275 cag ttc ctg att aac cac aaa ccg ttc tac ttt act ggc ttt ggt cgt    6737
Gln Phe Leu Ile Asn His Lys Pro Phe Tyr Phe Thr Gly Phe Gly Arg
280                 285                 290                 295 cat gaa gat gcg gac ttg cgt ggc aaa gga ttc gat aac gtg ctg atg    6785
His Glu Asp Ala Asp Leu Arg Gly Lys Gly Phe Asp Asn Val Leu Met
            300                 305                 310 gtg cac gac cac gca tta atg gac tgg att ggg gcc aac tcc tac cgt    6833
Val His Asp His Ala Leu Met Asp Trp Ile Gly Ala Asn Ser Tyr Arg
        315                 320                 325 acc tcg cat tac cct tac gct gaa gag atg ctc gac tgg gca gat gaa    6881
Thr Ser His Tyr Pro Tyr Ala Glu Glu Met Leu Asp Trp Ala Asp Glu
    330                 335                 340 cat ggc atc gtg gtg att gat gaa act gct gct gtc ggc ttt aac ctc    6929
His Gly Ile Val Val Ile Asp Glu Thr Ala Ala Val Gly Phe Asn Leu
345                 350                 355 tct tta ggc att ggt ttc gaa gcg ggc aac aag ccg aaa gaa ctg tac    6977
Ser Leu Gly Ile Gly Phe Glu Ala Gly Asn Lys Pro Lys Glu Leu Tyr
360                 365                 370                 375 agc gaa gag gca gtc aac ggg gaa act cag caa gcg cac tta cag gcg    7025
Ser Glu Glu Ala Val Asn Gly Glu Thr Gln Gln Ala His Leu Gln Ala
            380                 385                 390 att aaa gag ctg ata gcg cgt gac aaa aac cac cca agc gtg gtg atg    7073
Ile Lys Glu Leu Ile Ala Arg Asp Lys Asn His Pro Ser Val Val Met
        395                 400                 405 tgg agt att gcc aac gaa ccg gat acc cgt ccg caa ggt gca cgg gaa    7121
Trp Ser Ile Ala Asn Glu Pro Asp Thr Arg Pro Gln Gly Ala Arg Glu
    410                 415                 420 tat ttc gcg cca ctg gcg gaa gca acg cgt aaa ctc gac ccg acg cgt    7169
Tyr Phe Ala Pro Leu Ala Glu Ala Thr Arg Lys Leu Asp Pro Thr Arg
425                 430                 435 ccg atc acc tgc gtc aat gta atg ttc tgc gac gct cac acc gat acc    7217
Pro Ile Thr Cys Val Asn Val Met Phe Cys Asp Ala His Thr Asp Thr
440                 445                 450                 455 atc agc gat ctc ttt gat gtg ctg tgc ctg aac cgt tat tac gga tgg    7265
Ile Ser Asp Leu Phe Asp Val Leu Cys Leu Asn Arg Tyr Tyr Gly Trp
            460                 465                 470 tat gtc caa agc ggc gat ttg gaa acg gca gag aag gta ctg gaa aaa    7313
Tyr Val Gln Ser Gly Asp Leu Glu Thr Ala Glu Lys Val Leu Glu Lys
        475                 480                 485 gaa ctt ctg gcc tgg cag gag aaa ctg cat cag ccg att atc atc acc    7361
Glu Leu Leu Ala Trp Gln Glu Lys Leu His Gln Pro Ile Ile Ile Thr
    490                 495                 500 gaa tac ggc gtg gat acg tta gcc ggg ctg cac tca atg tac acc gac    7409
Glu Tyr Gly Val Asp Thr Leu Ala Gly Leu His Ser Met Tyr Thr Asp
505                 510                 515 atg tgg agt gaa gag tat cag tgt gca tgg ctg gat atg tat cac cgc    7457
Met Trp Ser Glu Glu Tyr Gln Cys Ala Trp Leu Asp Met Tyr His Arg
520                 525                 530                 535 gtc ttt gat cgc gtc agc gcc gtc gtc ggt gaa cag gta tgg aat ttc    7505
Val Phe Asp Arg Val Ser Ala Val Val Gly Glu Gln Val Trp Asn Phe
            540                 545                 550
```

```
gcc gat ttt gcg acc tcg caa ggc ata ttg cgc gtt ggc ggt aac aag      7553
Ala Asp Phe Ala Thr Ser Gln Gly Ile Leu Arg Val Gly Gly Asn Lys
            555                 560                 565 aaa ggg atc ttc act cgc gac cgc aaa ccg aag tcg gcg gct ttt ctg      7601
Lys Gly Ile Phe Thr Arg Asp Arg Lys Pro Lys Ser Ala Ala Phe Leu
570             575                 580 ctg caa aaa cgc tgg act ggc atg aac ttc ggt gaa aaa ccg cag gga      7649
Leu Gln Lys Arg Trp Thr Gly Met Asn Phe Gly Glu Lys Pro Gln Gly
    585                 590                 595 ggc aaa caa tgatctagac tcgag                                         7673
Gly Lys Gln
600
```

<210> SEQ ID NO 21
<211> LENGTH: 602
<212> TYPE: PRT
<213> ORGANISM: artificial
<220> FEATURE:
<223> OTHER INFORMATION: Synthetic Construct

<400> SEQUENCE: 21

```
Met Val Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285
```

Tyr Phe Thr Gly Phe Gly Arg His Glu Asp Ala Asp Leu Arg Gly Lys
            290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Ala Val Asn Gly Glu Thr
370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
        435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
        515                 520                 525

Trp Leu Asp Met Tyr His Arg Val Phe Asp Arg Val Ser Ala Val Val
530                 535                 540

Gly Glu Gln Val Trp Asn Phe Ala Asp Phe Ala Thr Ser Gln Gly Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gly Gly Lys Gln
        595                 600

<210> SEQ ID NO 22
<211> LENGTH: 22
<212> TYPE: DNA
<213> ORGANISM: artificial
<220> FEATURE:
<223> OTHER INFORMATION: PCR primer

<400> SEQUENCE: 22
gcagccttaa cagtcggcac ct                                          22

<210> SEQ ID NO 23
<211> LENGTH: 23
<212> TYPE: DNA
<213> ORGANISM: artificial
<220> FEATURE:

<223> OTHER INFORMATION: PCR primer

<400> SEQUENCE: 23
acgtgcaaca atctgcaaag cac 23

<210> SEQ ID NO 24
<211> LENGTH: 2999
<212> TYPE: DNA
<213> ORGANISM: artificial
<220> FEATURE:
<223> OTHER INFORMATION: pVAX vector

<400> SEQUENCE: 24

```
gactcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga     240
ctatttacgg taaactgccc acttggcagt acatcaagtg tatcatatgc caagtacgcc     300
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca gctggctag cgtttaaact taagcttggt     720
accgagctcg gatccactag tccagtgtgg tggaattctg cagatatcca gcacagtggc     780
ggccgctcga gtctagaggg cccgtttaaa cccgctgatc agcctcgact gtgccttcta     840
gttgccagcc atctgttgtt tgcccctccc ccgtgccttc cttgaccctg gaaggtgcca     900
ctcccactgt cctttcctaa taaaatgagg aaattgcatc gcattgtctg agtaggtgtc     960
attctattct ggggggtggg gtggggcagg acagcaaggg ggaggattgg gaagacaata    1020
gcaggcatgc tggggatgcg gtgggctcta tggcttctac tgggcggttt tatggacagc    1080
aagcgaaccg gaattgccag ctggggcgcc ctctggtaag gttgggaagc cctgcaaagt    1140
aaactggatg gctttctcgc cgccaaggat ctgatggcgc aggggatcaa gctctgatca    1200
agagacagga tgaggatcgt ttcgcatgat tgaacaagat ggattgcacg caggttctcc    1260
ggccgcttgg gtggagaggc tattcggcta tgactgggca acagacaa tcggctgctc     1320
tgatgccgcc gtgttccggc tgtcagcgca ggggcgcccg gttcttttg tcaagaccga    1380
cctgtccggt gccctgaatg aactgcaaga cgaggcagcg cggctatcgt ggctggccac    1440
gacgggcgtt ccttgcgcag ctgtgctcga cgttgtcact gaagcgggaa gggactggct    1500
gctattgggc gaagtgccgg ggcaggatct cctgtcatct caccttgctc ctgccgagaa    1560
agtatccatc atggctgatg caatgcggcg gctgcatacg cttgatccgg ctacctgccc    1620
attcgaccac caagcgaaac atcgcatcga gcgagcacgt actcggatgg aagccggtct    1680
tgtcgatcag gatgatctgg acgaagagca tcaggggctc gcgccagccg aactgttcgc    1740
caggctcaag gcgagcatgc ccgacggcga ggatctcgtc gtgacccatg gcgatgcctg    1800
cttgccgaat atcatggtgg aaaatggccg cttttctgga ttcatcgact gtggccggct    1860
gggtgtggcg gaccgctatc aggacatagc gttggctacc cgtgatattg ctgaagagct    1920
```

```
tggcggcgaa tgggctgacc gcttcctcgt gctttacggt atcgccgctc ccgattcgca    1980
gcgcatcgcc ttctatcgcc ttcttgacga gttcttctga attattaacg cttacaattt    2040
cctgatgcgg tattttctcc ttacgcatct gtgcggtatt tcacaccgca tacaggtggc    2100
acttttcggg gaaatgtgcg cggaacccct atttgtttat ttttctaaat acattcaaat    2160
atgtatccgc tcatgagaca ataaccctga taaatgcttc aataatagca cgtgctaaaa    2220
cttcattttt aatttaaaag gatctaggtg aagatccttt ttgataatct catgaccaaa    2280
atcccttaac gtgagttttc gttccactga gcgtcagacc ccgtagaaaa gatcaaagga    2340
tcttcttgag atcctttttt tctgcgcgta atctgctgct tgcaaacaaa aaaaccaccg    2400
ctaccagcgg tggtttgttt gccggatcaa gagctaccaa ctcttttcc gaaggtaact    2460 ggcttcagca gagcgcagat accaaatact gtccttctag tgtagccgta gttaggccac    2520
cacttcaaga actctgtagc accgcctaca tacctcgctc tgctaatcct gttaccagtg    2580
gctgctgcca gtggcgataa gtcgtgtctt accgggttgg actcaagacg atagttaccg    2640
gataaggcgc agcggtcggg ctgaacgggg ggttcgtgca cacagcccag cttggagcga    2700
acgacctaca ccgaactgag atacctacag cgtgagctat gagaaagcgc cacgcttccc    2760
gaagggagaa aggcggacag gtatccggta agcggcaggg tcggaacagg agagcgcacg    2820
agggagcttc caggggggaaa cgcctggtat ctttatagtc ctgtcgggtt cgccacctc    2880 tgacttgagc gtcgattttt gtgatgctcg tcagggggc ggagcctatg gaaaaacgcc    2940
agcaacgcgg cctttttacg gttcctgggc ttttgctggc cttttgctca catgttctt    2999
```

<210> SEQ ID NO 25
<211> LENGTH: 347
<212> TYPE: DNA
<213> ORGANISM: artificial
<220> FEATURE:
<223> OTHER INFORMATION: synthetic

<400> SEQUENCE: 25

```
gctagcatgg acgccaaggt cgtcgccgtg ctggccctgg tgctggccgc gctctgcatc     60
agtgacggta aaccagtcag cctgagctac cgatgcccct gccggttctt cgagagccac    120
atcgccagag ccaacgtcaa gcatctgaaa atcctcaaca ctccaaactg tgcccttcag    180
attgttgcac ggctgaagaa caacaacaga caagtgtgca ttgacccgaa attaaagtgg    240
atccaagagt acctggagaa agccttaaac aagggatcag gtgccacgaa cttctctctg    300
ttaaagcaag caggagacgt ggaagaaaac cccggtccca aaagctt                   347
```

<210> SEQ ID NO 26
<211> LENGTH: 5395
<212> TYPE: DNA
<213> ORGANISM: artificial
<220> FEATURE:
<223> OTHER INFORMATION: vector

<400> SEQUENCE: 26

```
gactcttcgc gatgtacggg ccagatatac gcgttgacat tgattattga ctagttatta     60
atagtaatca attacggggt cattagttca tagcccatat atggagttcc gcgttacata    120
acttacggta aatggcccgc ctggctgacc gcccaacgac ccccgcccat tgacgtcaat    180
aatgacgtat gttcccatag taacgccaat agggactttc cattgacgtc aatgggtgga    240
ctatttacgg taaactgccc acttggcagt acatcaagtg tatcatatgc caagtacgcc    300
```

```
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttcgc    720
caccatggag agcgacgaga gcggcctgcc cgccatggag atcgagtgcc gcatcaccgg    780
caccctgaac ggcgtggagt cgagctggt gggcggcgga gagggcaccc ccaagcaggg    840
ccgcatgacc aacaagatga agagcaccaa aggcgccctg accttcagcc cctacctgct    900
gagccacgtg atgggctacg gcttctacca cttcggcacc taccccagcg gctacgagaa    960
cccccttcctg cacgccatca caacggcgg ctacaccaac acccgcatcg agaagtacga   1020
ggacggcggc gtgctgcacg tgagcttcag ctaccgctgc gaggccggcc gcgtgatcgg   1080
cgacttcaag gtggtgggca ccggcttccc cgaggacagc gtgatcttca ccgacaagat   1140
catccgcagc aacgccaccg tggagcacct gcaccccatg ggcgataacg tgctggtggg   1200
cagcttcgcc cgcaccttca gcctgcgcga cggcggctac cacagcttcg tggtggacaa   1260
ccacatgcac ttcaagagcg ccatccaccc cagcatcctg cagaacgggg ccccatgtt   1320
cgccttccgc cgcgtggagg agctgcacag caacaccgag ctgggcatcg tggagtacca   1380
gcacgccttc aagaccccca tcgccttcgc cagatcccgc gctcagtcgt ccaattctgc   1440
cgtggacggc accgccggac ccggctccac cggatctcgc gagggcagag gaagtcttct   1500
aacatgcgt gacgtggagg agaatcccgg ccctatggaa gatgccaaaa acattaagaa   1560
gggcccagcg ccattctacc cactcgaaga cgggaccgcc ggcgagcagc tgcacaaagc   1620
catgaagcgc tacgccctgg tgcccggcac catcgccttt accgacgcac atatcgaggt   1680
ggacattacc tacgccgagt acttcgagat gagcgttcgg ctggcagaag ctatgaagcg   1740
ctatgggctg aatacaaacc atcggatcgt ggtgtgcagc gagaatagct tgcagttctt   1800
catgccgtg ttgggtgccc tgttcatcgg tgtggctgtg gccccagcta acgacatcta   1860
caacgagcgc gagctgctga acagcatggg catcagccag cccaccgtcg tattcgtgag   1920
caagaaaggg ctgcaaaaga tcctcaacgt gcaaaagaag ctaccgatca tacaaaagat   1980
catcatcatg gatagcaaga ccgactacca gggcttccaa agcatgtaca ccttcgtgac   2040
ttcccatttg ccacccggct tcaacgagta cgacttcgtg cccgagagct cgaccgggga   2100
caaaaccatc gccctgatca tgaacagtag tggcagtacc ggattgccca agggcgtagc   2160
cctaccgcac cgcaccgctt gtgtccgatt cagtcatgcc cgcgaccccca tcttcggcaa   2220
ccagatcatc cccgacaccg ctatcctcag cgtggtgcca tttcaccacg gcttcggcat   2280
gttcaccacg ctgggctact tgatctgcgg cttccgggtc gtgctcatgt accgcttcga   2340
ggaggagcta ttcttgcgca gcttgcaaga ctataagatt caatctgccc tgctggtgcc   2400
cacactattt agcttcttcg ctaagagcac tctcatcgac aagtacgacc taagcaactt   2460
gcacgagatc gccagcggcg gggcgccgct cagcaaggag gtaggtgagg ccgtggccaa   2520
acgcttccac ctaccaggca tccgccaggg ctacggcctg acagaaacaa ccagcgccat   2580
tctgatcacc cccgaagggg acgacaagcc tggcgcagta ggcaaggtgg tgcccttctt   2640
cgaggctaag gtggtggact tggacaccgg taagacactg ggtgtgaacc agcgcggcga   2700
```

```
gctgtgcgtc cgtggcccca tgatcatgag cggctacgtt aacaacccccg aggctacaaa    2760 cgctctcatc gacaaggacg gctggctgca cagcggcgac atcgcctact gggacgagga    2820
cgagcacttc ttcatcgtgg accggctgaa gagcctgatc aaatacaagg gctaccaggt    2880
agccccagcc gaactggaga gcatcctgct gcaacacccc aacatcttcg acgccggggt    2940
cgccggcctg cccgacgacg atgccggcga gctgcccgcc gcagtcgtcg tgctggaaca    3000
cggtaaaacc atgaccgaga aggagatcgt ggactatgtg ccagccagg ttacaaccgc    3060 caagaagctg cgcggtggtg ttgtgttcgt ggacgaggtg cctaaaggac tgaccggcaa    3120
gttggacgcc cgcaagatcc gcgagattct cattaaggcc aagaagggcg gcaagatcgc    3180
cgtgtaatct agagggcccg tttaaacccg ctgatcagcc tcgactgtgc cttctagttg    3240
ccagccatct gttgtttgcc cctcccccgt gccttccttg accctggaag gtgccactcc    3300
cactgtcctt tcctaataaa atgaggaaat tgcatcgcat tgtctgagta ggtgtcattc    3360
tattctgggg ggtggggtgg ggcaggacag caagggggag gattgggaag acaatagcag    3420
gcatgctggg gatgcggtgg gctctatggc ttctactggg cggttttatg gacagcaagc    3480
gaaccggaat tgccagctgg ggcgccctct ggtaaggttg ggaagccctg caaagtaaac    3540
tggatggctt tctcgccgcc aaggatctga tggcgcaggg gatcaagctc tgatcaagag    3600
acaggatgag gatcgtttcg catgattgaa caagatggat tgcacgcagg ttctccggcc    3660
gcttgggtgg agaggctatt cggctatgac tgggcacaac agacaatcgg ctgctctgat    3720
gccgccgtgt tccggctgtc agcgcagggg cgcccggttc tttttgtcaa gaccgacctg    3780
tccggtgccc tgaatgaact gcaagacgag gcagcgcggc tatcgtggct ggccacgacg    3840
ggcgttcctt gcgcagctgt gctcgacgtt gtcactgaag cgggaaggga ctggctgcta    3900
ttgggcgaag tgccggggca ggatctcctg tcatctcacc ttgctcctgc cgagaaagta    3960
tccatcatgg ctgatgcaat gcggcggctg catacgcttg atccggctac ctgcccattc    4020
gaccaccaag cgaaacatcg catcgagcga gcacgtactc ggatggaagc cggtcttgtc    4080
gatcaggatg atctggacga agagcatcag gggctcgcgc cagccgaact gttcgccagg    4140
ctcaaggcga gcatgcccga cggcgaggat ctcgtcgtga cccatggcga tgcctgcttg    4200
ccgaatatca tggtggaaaa tggccgcttt tctggattca tcgactgtgg ccggctgggt    4260
gtggcggacc gctatcagga catagcgttg gctacccgtg atattgctga agagcttggc    4320
ggcgaatggg ctgaccgctt cctcgtgctt tacggtatcg ccgctcccga ttcgcagcgc    4380
atcgccttct atcgccttct tgacgagttc ttctgaatta ttaacgctta caatttcctg    4440
atgcggtatt ttctccttac gcatctgtgc ggtatttcac accgcataca ggtggcactt    4500
ttcggggaaa tgtgcgcgga acccctattt gtttattttt ctaaatacat tcaaatatgt    4560
atccgctcat gagacaataa ccctgataaa tgcttcaata atagcacgtg ctaaaacttc    4620 attttaatt taaaggatc taggtgaaga tccttttga taatctcatg accaaaatcc    4680
cttaacgtga gttttcgttc cactgagcgt cagacccgt agaaaagatc aaaggatctt    4740
cttgagatcc ttttttttctg cgcgtaatct gctgcttgca acaaaaaaaa ccaccgctac    4800
cagcggtggt ttgtttgccg gatcaagagc taccaactct ttttccgaag gtaactggct    4860
tcagcagagc gcagatacca aatactgtcc ttctagtgta gccgtagtta ggccaccact    4920
tcaagaactc tgtagcaccg cctacatacc tcgctctgct aatcctgtta ccagtggctg    4980
ctgccagtgg cgataagtcg tgtcttaccg ggttggactc aagacgatag ttaccggata    5040
```

-continued

```
aggcgcagcg gtcgggctga acgggggggtt cgtgcacaca gcccagcttg gagcgaacga    5100
cctacaccga actgagatac ctacagcgtg agctatgaga aagcgccacg cttcccgaag    5160
ggagaaaggc ggacaggtat ccggtaagcg gcagggtcgg aacaggagag cgcacgaggg    5220
agcttccagg gggaaacgcc tggtatcttt atagtcctgt cgggtttcgc cacctctgac    5280
ttgagcgtcg atttttgtga tgctcgtcag ggggcggag cctatggaaa aacgccagca    5340
acgcggcctt tttacggttc ctgggctttt gctggccttt tgctcacatg ttctt         5395
```

METHODS FOR WOUND HEALING

CROSS-REFERENCE TO RELATED APPLICATION(S)

This application is a National Phase Patent Applications of International Patent Application Number PCT/EP2015/081146, filed on Dec. 23, 2015, which claims priority of Swedish Patent Application 1451658-7, filed Dec. 23, 2014. The entire contents of both of which are incorporated herein by reference.

SEQUENCE LISTING

The instant application contains a Sequence Listing which has been submitted in ASCII format via EFS-Web and is hereby incorporated by reference in its entirety. Said ASCII copy filed in the International Patent Application number PCT/EP2015/081146, was modified on Oct. 23, 2017 and is named amendedeolf-seql.txt and is 75,467 bytes in size.

FIELD OF THE INVENTION

The invention relates generally to recombinant plasmids, and in particular to plasmids capable of expressing a recombinant protein targeting immune cells when transformed into a lactic acid bacterial cell, wherein the said protein is chosen from the group consisting of murine and human CXCL12 1α, CXCL17 and Ym1. The invention further relates to lactic acid bacteria transformed with a said plasmid, as well as the use of said lactic acid bacteria for wound healing in humans and animals.

BACKGROUND TO THE INVENTION

The process of wound healing has overlapping phases (coagulation phase, inflammatory phase and proliferative/remodelling phase) where constituents of the local microenvironment change over time and distinct cell types play different roles. Key cell players in the healing process are platelets, keratinocytes/epithelial cells, fibroblasts/myofibroblasts, different immune cells and endothelial cells. All tissues in the body can be injured and the healing process is somewhat specific to the organ, however the initial signals elicited by the damaged cells are similar. The most studied form of wound healing is in skin.

Tissue injury disrupts homeostasis, which initiates the coagulation process and activates the sympathetic nervous system. The platelets forming the blood clots release signals, mainly PDGF (platelet derived growth factor) and TGF (transforming growth factor) changing the local environment (Ref. 1). Injured and stressed cells release alarm signals that initiate the recruitment of immune cells such as neutrophils and monocytes. Within the wounded tissue, the immune cells secrete various chemokines, growth factors like VEGF-A, FGF, and EGF (vascular endothelial growth factor A, fibroblast growth factor, epidermal growth factor), ROS (reactive oxygen species) and matrix digestive enzymes, which change the microenvironment and allow the healing process to enter the proliferative phase where failing and dead tissue is removed by macrophages. Cells from the wound edges, such as fibroblasts and keratinocytes, migrate inwards to the wound centre and cover the wound surface with a layer of collagen and extracellular matrix. The fibroblasts within the wound are then transformed into myofibroblasts expressing contractile α-SMA (α-smooth muscle actin) allowing the wound to contract and finally close. The transition from fibroblasts into myofibroblasts is dependent on signals from the microenvironment, some of which originate from immune cells, mainly macrophages. During this process, blood vessels are growing into the newly formed tissue, the granulation tissue. Blood flow to the adjacent area is normally increased during this phase to increase the availability of oxygen and nutrients, in addition to immune cell recruitment and migration to the afflicted site.

Following wound closure, the afflicted site becomes re-epithelialized by keratinocytes/epithelial cells whereby the integrity of the organ barrier is regained. Even after wound closure, some tissue remodelling occurs to normalize the matrix structure and the majority of involved immune cells either die or leave the site. Also at this stage dead or dying cells are ingested and cleared (phagocytosed) by the remaining tissue macrophages (Ref. 1). Faster wound healing reduces complications and discomfort to the patient, Impaired or delayed cutaneous or mucosal wound healing is a worldwide clinical problem causing pain, direct exposure to pathogens, loss of tissue function and loss of temperature and fluid balance regulation. There are several conditions where the tightly regulated wound healing process is impaired and the cutaneous or mucosal wounds remain unhealed for longer time periods than normal, which in worst case become chronic.

Reduced blood flow to the skin, especially in extremities, significantly reduces the efficiency of the healing process. There are several clinical conditions where the skin perfusion is either reduced or the function of the vasculature is impaired such as PAD (peripheral artery disease), intermittent claudication, vein insufficiency or vessel obstruction by arteriosclerotic plaques. Impaired blood flow to the wound area results in shortage of oxygen and nutrients and the cells aiding in the tissue remodeling either die from necrosis or are unable to perform their tasks on site. Also the surrounding tissue will if not sufficiently supplied lose functionality and ultimately start to die. Tissues are during the remodeling phase very metabolically active and have high oxygen consumption.

Another factor impairing cutaneous wound healing is hyperglycemia and diabetes mellitus. During hyperglycemic conditions cell signaling and immune system functions are impaired. Complications resulting from diabetes include microvascular changes and damage to peripheral neurons. As a result, diabetic patients often develop chronic wounds on their feet, commonly called diabetic foot. The available treatment for these patients today is removal of dead tissue using surgical debridement or collagenase together with systemic antibiotic treatment and closed wound dressing. There are experimental studies where growth factors and biomaterials have been applied to chronic wounds (Ref. 2).

The stromal cell-derived factor 1 (SDF-1) also known as C-X-C motif chemokine 12 (CXCL12) is a chemokine protein that in humans is encoded by the CXCL12 gene. WO 2009/079451 discloses a method for promoting wound healing in a subject, comprising administering directly to the wound or an area proximate the wound an amount of SDF-1 effective to promote healing of the wound of the subject.

Certain probiotics (*Lactobacillus reuteri* ATCC PTA 6475) have been shown to facilitate wound healing if supplemented in the drinking water during the healing process (Ref. 9), i.e. the bacteria were ingested. Further, supernatants from culture of *Lactobacillus plantarum* have been demonstrated to inhibit biofilm production by *Pseudomonas aeruginosa*, commonly infecting chronic wounds (Ref. 10).

It has surprisingly been found that lactic acid bacteria which are modified, according to the present invention, to express specific proteins, such as cytokines, are useful for promoting wound healing. Lactic acid bacteria are sparsely present on the human skin (Ref. 13) and are not the expected choice of bacteria to use for any intervention on the skin. *Lactobacilli* are difficult to work with since they grow relatively slowly and require special medium and conditions in comparison with more commonly used bacteria like *E. coli* and *S. aureus*. Further, *Lactobacilli* have limited intracellular machinery for transcription, translation and protein folding. For this reason, nucleotide sequences coding for heterologous proteins have to be optimized to fit the specific bacterial strain.

The different phases of wound healing comprise distinct key events that could be altered to change the healing process. Vascular remodeling during the healing process is highly dependent on induction of hypoxia inducible factor 1α (HIF-1α) that regulates the expression of VEGF-A (vascular endothelial growth factor A) and a range of chemokines, such as CXCL12 (also known as SDF-1; SEQ ID NO: 3 and 6). CXCL12 is constitutively expressed in tissues and acts through the receptor CXCR4 found on leukocytes and endothelial cells inducing multiple cellular actions (Ref. 3). CXCL12 is found in high levels in macrophages specialized in tissue remodeling (Ref. 4). Dermal overexpression of CXCL12 using lentiviral vectors improves wound healing in diabetic mice (Ref. 5).

Another recently discovered chemokine is CXCL17 (SEQ ID NO: 9 and 12), which has similar effects on the phenotype of tissue macrophages as CXCL12. In similarity with CXCL12, CXCL17 is co-regulated with VEGF-A measured in cell culture (Ref. 6). CXCL17 is found mainly in mucosal tissues and have been reported to be directly antimicrobial to pathogenic bacteria that are also found on skin whilst showing no effect on survival of *Lactobacillus casei* (Ref. 7).

A further protein of interest is Ym1 (SEQ ID NO: 15 and 18), which is a chitinase-like protein. Chitin is a common polysaccharide in bacterial biofilm. Ym1 both counteracts biofilm production and induces macrophage functions important for tissue remodeling and wound healing and is specific to macrophages since it is not taken up by either vascular cells or epithelial cells (Ref. 8).

Consequently, in a first aspect the invention provides a recombinant plasmid which is capable of expressing a protein in lactic acid bacteria (i.e. when transformed into a lactic acid bacterial cell), wherein the said protein is useful for improving wound healing, such as cutaneous or mucosal wound healing, in a human or animal subject. Preferably, the said protein is useful for wound healing due to its capability of targeting immune cells such as macrophages and their precursors. Preferably, the said protein is a cytokine or chemokine. Most preferably, the said protein is chosen from the group consisting of murine CXCL12, in particular murine CXCL12-1α (SEQ ID NO: 3); human CXCL12, in particular human CXCL12-1α (SEQ ID NO: 6); murine CXCL17 (SEQ ID NO: 9); human CXCL17 (SEQ ID NO: 12); murine Ym1 (SEQ ID NO: 15); and human Ym1 (SEQ ID NO: 18).

This first aspect of the invention more particularly provides a plasmid which is capable of expressing a recombinant protein in lactic acid bacteria (i.e. when transformed into a lactic acid bacterial cell), wherein said plasmid comprises a nucleotide sequence encoding a protein selected from CXCL12, CXCL17 and Ym1.

More specifically the nucleotide sequence may encode murine CXCL12, in particular murine CXCL12-1α; human CXCL12, in particular human CXCL12-1α; murine CXCL17; human CXCL17; murine Ym1; or human Ym1.

In one embodiment, the plasmid comprises a nucleotide sequence encoding a protein selected from murine CXCL12-1α having an amino acid sequence as shown in SEQ ID NO: 3 or 2, or an amino acid sequence with at least 80% sequence identity thereto; human CXCL12-1α having an amino acid sequence as shown in SEQ ID NO: 6 or 5, or an amino acid sequence with at least 80% sequence identity thereto; murine CXCL17 having an amino acid sequence as shown in SEQ ID NO: 9 or 8, or an amino acid sequence with at least 80% sequence identity thereto; human CXCL17 having an amino acid sequence as shown in SEQ ID NO: 12 or 11, or an amino acid sequence with at least 80% sequence identity thereto; murine Ym1 having an amino acid sequence as shown in SEQ ID NO: 15 or 14, or an amino acid sequence with at least 80% sequence identity thereto; and human Ym1 as shown in SEQ ID NO: 18 or 17 or an amino acid sequence with at least 80% sequence identity thereto.

More particularly, the plasmid is for use in expressing a protein in lactic acid bacteria and is accordingly provided, or adapted, for such use (e.g. it is designed, selected, adapted or modified for specific or particular use in lactic acid bacteria). Thus in one embodiment the plasmid is for specific expression in lactic acid bacteria, as compared to bacteria or microorganisms generally. The plasmid may be adapted for expression in lactic acid bacteria by means of its regulatory elements (regulatory sequences) and/or coding sequences, e.g. which are selected or modified for expression in lactic acid bacteria.

Accordingly, in a more particular aspect the plasmid comprises one or more regulatory (i.e. expression control) sequences which permit expression, or which are specific for expression, in lactic acid bacteria. Thus, the plasmid may contain expression control sequences derived from, or suitable for, or specific for, expression in lactic acid bacteria. Appropriate expression control sequences include for example translational (e.g. start and stop codons, ribosomal binding sites) and transcriptional control elements (e.g. promoter-operator regions, termination stop sequences), linked in matching reading frame with the nucleotide sequence(s) which encode the protein(s) to be expressed. The regulatory sequences(s) are operably linked to a nucleotide sequence encoding said protein, such that they drive, or control, expression of the protein. The plasmid may be introduced into a lactic acid bacterial cell. Suitable transformation techniques are well described in the literature. The bacterial cell may be cultured or otherwise maintained under conditions permitting expression of said protein from the plasmid. This may include conditions in a wound in a subject.

In one embodiment the promoter in the plasmid which controls expression of the protein is a promoter which permits, or which is specific for, expression in lactic acid bacteria. Thus the plasmid may comprise a nucleotide sequence(s) encoding the protein(s), under the control of (or operably linked to) a promoter capable of expressing the protein in lactic acid bacteria. In a particular preferred embodiment the plasmid comprises a lactic acid bacteria promoter, that is the promoter which controls expression of the protein(s) is a promoter which is derived from a lactic acid bacterium, or more particularly which is obtained or derived from a gene expressed in a lactic acid bacterium.

In some embodiments, in addition to a lactic acid bacterial promoter, the plasmid may also contain other regulatory elements or sequences obtained or derived from lactic acid bacteria to control expression of the protein(s). Thus for example such other lactic acid bacterial expression control elements or sequences may include enhancers, terminators and/or translational control elements or sequences as discussed above. In some embodiments the plasmid may also contain regulatory elements or sequences which control or regulate expression from the promoter e.g. operator sequences etc. or one or more regulatory genes, as discussed further below.

Alternatively or additionally the plasmid may be adapted (or modified etc.) for use in lactic acid bacteria by virtue of the nucleotide sequences encoding the protein(s) being codon-optimised for expression in lactic acid bacteria.

In a preferred embodiment the promoter for expression of the protein is a regulated (regulatable) or inducible promoter. Thus, expression of the protein may be controlled or regulated (e.g. initiated, for example at a desired or appropriate time) by providing or contacting the bacteria with a regulatory molecule or inducer which activates or turns on (induces) the promoter. This is advantageous in the context of delivery of the protein to a wound.

Accordingly, a further aspect of the invention provides an expression system for use in expressing a protein in lactic acid bacteria, said expression system comprising (i) a plasmid as defined herein, wherein said plasmid comprises a nucleotide sequence encoding a said protein under the control of an inducible promoter capable of expressing the protein in lactic acid bacteria; and (ii) an inducer (or regulatory molecule) for the promoter. The expression system may conveniently be provided in the form of a kit comprising components (i) and (ii) above.

A still further aspect of the present invention is a bacterium, or bacteria, (i.e. a bacterial cell or strain) transformed with (i.e. comprising) a plasmid of the invention, as defined herein. Particularly, the bacterium is a lactic acid bacterium and the invention accordingly provides lactic acid bacteria (or a lactic acid bacterium) comprising a plasmid of the invention, as defined herein. Alternatively expressed, this aspect of the invention provides a bacterium (or bacterial cell) into which a plasmid of the invention has been introduced.

As described further herein, the plasmids and bacteria of the invention are useful for promoting healing, and thus have particular utility in promoting healing of wounds, which are defined herein to include injured tissue generally (see further below). Accordingly further aspects of the invention provide such plasmids and bacteria for use in therapy, and more particularly for use in wound healing.

The bacteria may be provided for administration to a wound in a subject to be treated in the form of a pharmaceutical composition. Accordingly a still further aspect of the invention provides a pharmaceutical composition comprising bacteria of the invention as defined herein, together with at least one pharmaceutically acceptable carrier or excipient.

More generally, the invention provides a probiotic product comprising the bacteria of the invention.

Such a product, or pharmaceutical composition, may conveniently take the form of a wound dressing comprising the bacteria of the invention. Thus, in a further aspect the invention provides a wound dressing comprising bacteria of the invention as hereinbefore defined, together with at least one dressing material.

A yet further aspect of the invention provides use of a plasmid or of bacteria of the invention as defined herein for the manufacture of a medicament (or a probiotic product) for use in wound healing.

Also provided is a method of treating a subject to heal a wound, said method comprising administering to said subject, or to the wound in said subject, an amount of bacteria of the invention as defined herein effective to promote healing of the wound.

Another aspect of the invention provides a kit for healing wounds, said kit comprising:
(i) lactic acid bacteria comprising a plasmid of the invention as defined herein, wherein said plasmid comprises a nucleotide sequence encoding a said protein under the control of an inducible promoter capable of expressing the protein in lactic acid bacteria; and
(ii) an inducer (or regulatory molecule) for the promoter.

A still further aspect of the invention comprises a pharmaceutical product (e.g. a kit or combination product) comprising;
(i) lactic acid bacteria comprising a plasmid of the invention as defined herein, wherein said plasmid comprises a nucleotide sequence encoding a said protein under the control of an inducible promoter capable of expressing the protein in lactic acid bacteria; and
(ii) an inducer (or regulatory molecule) for the promoter, as a combined preparation for separate, sequential or simultaneous use in wound healing (or for treating a wound in a subject).

The term "wound healing" is used broadly herein to include any aspect of promoting or improving the healing of a wound. Thus, the various aspects of the invention set out above may alternatively be defined with respect to a utility of the plasmids or bacteria in promoting or enhancing or improving wound healing or simply promoting or enhancing healing.

Wound healing may accordingly include or encompass any effect which results in faster wound healing, or more complete healing of a wound or indeed any amelioration or improvement in the healing of a wound, e.g. reduced healing time, for example reduced time to achieve partial or complete closure of a wound, improved wound appearance (e.g. the appearance of a healed or healing wound), reduced or improved scar formation, the promotion of healing of a chronic or recalcitrant wound etc. (i.e. the application of the bacteria of the invention to a wound may induce, or cause, or start, the healing of a wound which has up to now not healed or shown any signs of healing). Wounds are discussed in more detail below.

The subject having a wound to be treated may be any human or animal subject, including for example domestic animals, livestock animals, laboratory animals, sports animals or zoo animals. The animal is preferably a mammalian animal, but other animals, e.g. birds are included. Thus the animal may be a primate, a rodent (e.g. a mouse or rat), or a horse, dog or cat. Most preferably the subject is a human.

Lactic acid bacteria (LAB) or Lactobacillales are a clade of Gram-positive, low-GC, acid-tolerant, generally nonsporulating, nonrespiring, either rod-shaped (*bacillus*), or spherical (*coccus*) bacteria which share common metabolic and physiological characteristics. These bacteria produce lactic acid as the major metabolic end product of carbohydrate fermentation and are characterized by an increased tolerance to acidity (low pH range). These characteristics of LAB allow them to outcompete other bacteria in a natural fermentation because LAB can withstand the increased acidity from organic acid production (e.g. lactic acid). Thus LAB play an important role in food fermentations, as acidification inhibits the growth of spoilage agents. Several LAB strains also produce proteinaceous bacteriocins which further inhibit spoilage and growth of pathogenic microorganisms. LAB have generally recognized as safe (GRAS) status and are amongst the most important groups of microorganisms used in the food industry.

The core genera that comprise the lactic acid bacteria clade are *Lactobacillus, Leuconostoc, Pediococcus, Lactococcus*, and *Streptococcus*, as well as the more peripheral *Aerococcus, Carnobacterium, Enterococcus, Oenococcus, Sporolactobacillus, Tetragenococcus, Vagococcus*, and *Weissella*. Any lactic acid bacteria from these genera are included within the scope of the present invention, but particularly bacteria from the genera *Lactobacillus* or *Lactococcus*.

The plasmid may encode one or more of said proteins. Thus it may encode a combination of a CXCL12, CXCL17 and/or a Ym1 protein (e.g. 2 or more of CXCL12, CXCL17 or Ym1). Alternatively, it may encode 2 or more types of a CXCL12, CXCL17 and/or Ym1 protein (e.g. both murine and human CXCL12 etc.). Where more than one protein is encoded, the protein may be expressed from a nucleotide sequence encoding the proteins under the control of a single promoter, or more than one promoter may be used. For example, each protein may be expressed from a separate promoter, which may be the same or different. Techniques for expression of 2 or more proteins together from the same plasmid are well known in the art and include for example translational coupling techniques etc., means for achieving this are known and available in the art. For example multiple transgenes can be expressed simultaneously under one promoter using P2A and T2A sequences.

The CXCL12, CXCL17 or Ym1 protein may be a native or natural protein (i.e. the nucleotide sequence may encode a protein having an amino acid sequence as found in nature) and may be from any species in which these proteins occur. Generally the protein will be a mammalian protein and as indicated above human and murine proteins are preferred. However, the native nucleotide sequences or protein sequences may be modified, for example by one or more amino acid additions, insertions, deletions and/or substitutions, as long as the function or activity of the protein is not substantially or significantly altered, e.g. as long as the activity of the protein is substantially retained. The protein may be a fragment or truncated variant of a natural protein. For example, a sequence-modified variant protein may exhibit at least 80, 85, 90 or 95% of the activity of the parent protein from which it is derived. This may be assessed according to tests known in the art for activity of the protein in question. For example, activity can be measured in systems of receptor phosphorylation or calcium flux upon ligation in culture cells treated with the protein, in systems of cell chemotaxis in vitro or in vivo in models of cell recruitment to the infected protein. An in vitro assay based on chemotaxis is described in Refs. 22 and 32. Ref. 33 describes a further in vitro chemokine activity test which might be used. The terms "CXCL12", "CXCL17" or "Ym1" thus include not only the native proteins but also functionally equivalent variants or derivatives thereof. The proteins may thus be synthetic or sequence-modified variants, or may comprise one or more other modifications, e.g. post-translational modifications etc.

As mentioned above, the encoded proteins may have the amino acid sequences indicated above for the native human or murine proteins, namely SEQ ID NOS. 3 and 6 for murine and human CXCL12 respectively, 9 and 12 for murine and human CXCL17 respectively, and 15 and 18 for murine and human Ym1 respectively, or an amino acid sequence having at least 80% sequence identity to any aforesaid sequence. Advantageously, as further indicated above, the nucleotide sequences encoding these native proteins may be codon-optimised for expression in lactic acid bacteria. This may result in a modified amino acid sequence of the protein encoded. For example codon optimised sequences may encode sequences such as secretion sequences suitable, (or better suited) for lactic acid bacteria. Thus the "optimized" protein encoded by a codon-optimised nucleotide sequence may include an altered or substituted leader or signal sequence (e.g. secretory sequence) as compared to the native protein. In a preferred embodiment the mature or cleaved form of the protein encoded by the codon optimised sequence is identical to the native protein. Proteins encoded by codon-optimised nucleotide sequences may have an amino acid sequence as shown in SEQ ID NOS. 2, 5, 8, 11, 14, or 17 as listed in Table IV below. Thus, the protein encoded by the plasmid may have an amino acid sequence as shown in SEQ ID NOS. 2 and 5 for murine and human CXCL12 respectively, 8 and 11 for murine and human CXCL17 respectively, and 14 and 17 for murine and human Ym1 respectively, or an amino acid sequence having at least 80% sequence identity to any aforesaid sequence.

In other embodiments the encoded protein(s) may have an amino acid sequence which has at least 81%, 82%, 83%, 84%, 85%, 86%, 87%, 88%, 89% 90%, 91% 92% 93%, 94%, 95%, 96%, 97%, 98% or 99% sequence identity with any aforesaid amino acid sequence.

Sequence identity may readily be determined by methods and software known and readily available in the art. Thus, sequence identity may be assessed by any convenient method. However, for determining the degree of sequence identity between sequences, computer programs that make multiple alignments of sequences are useful, for instance Clustal W (Ref. 24). Programs that compare and align pairs of sequences, like ALIGN (Ref. 25), FASTA (Ref. 26 and Ref. 27), BLAST and gapped BLAST (Ref. 28) are also useful for this purpose, and may be used using default settings. Furthermore, the Dali server at the European Bioinformatics institute offers structure-based alignments of protein sequences (Ref. 29, Ref. 30 and Ref. 31). Multiple sequence alignments and percent identity calculations may be determined using the standard BLAST parameters, (e.g. using sequences from all organisms available, matrix Blosum 62, gap costs: existence 11, extension 1). Alternatively, the following program and parameters may be used: Program: Align Plus 4, version 4.10 (Sci Ed Central Clone Manager Professional Suite). DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix.

Variants of the naturally occurring polypeptide sequences as defined herein can be generated synthetically e.g. by using standard molecular biology techniques that are known in the art, for example standard mutagenesis techniques such as site-directed or random mutagenesis (e.g. using gene shuffling or error prone PCR).

Derivatives of the proteins as defined herein may also be encoded. By derivative is meant a protein as described above or a variant thereof in which the amino acid is chemically modified e.g. by glycosylation and such like etc.

Where a protein comprises an amino acid substitution relative to the sequence of the native protein, the substitution may preferably be a conservative substitution. The term "a conservative amino acid substitution" refers to any amino acid substitution in which an amino acid is replaced (substituted) with an amino acid having similar physicochemical properties, i.e. an amino acid of the same class/group. For instance, small residues Glycine (G), Alanine (A) Serine (S) or Threonine (T); hydrophobic or aliphatic residues Leucine (L), Isoleucine (I); Valine (V) or Methionine (M); hydrophilic residues Asparagine (N) and Glutamine (Q); acidic residues Aspartic acid (D) and Glutamic acid (E); positively-charged (basic) residues Arginine (R), Lysine (K) or Histidine (H); or aromatic residues Phenylalanine (F), Tyrosine (Y) and Tryptophan (W), may be substituted interchangeably without substantially altering the function or activity of the protein.

As indicated above, it is preferred to use an inducible promoter for expression of the protein. By "inducible" is meant any promoter whose function (i.e. activity, or effect in allowing or causing transcription of the coding nucleotide sequence) can be regulated or controlled. The term "inducible" is thus synonymous, and may be used interchangeably with "regulatable" (or "regulated"). Thus, there is not constitutive expression of the protein. Accordingly, expression of the protein may be induced, or turned on (or more particularly turned on and off). More particularly, expression may be induced, or turned on for a finite or defined time. This may be because expression ceases after a period of time, and/or because the bacterial cells die.

In some embodiments there may be no expression (transcription) from the promoter until the promoter is induced (or alternatively termed, activated). However, as with any biological system, lack of activity may not be absolute and there may be some basal promoter activity in the absence of promoter activation or induction. However, in a preferred embodiment any basal expression of the uninduced promoter is low, minimal, or insignificant, or more preferably de minimis or negligible. Thus, expression from the inducible promoter is advantageously measurably or demonstrably increased when the promoter is induced compared to the promoter when it is not induced.

Inducible promoters are well known in the art, including inducible promoters for use in lactic acid bacteria and any appropriate inducible promoter may be used, suitable for expression in lactic acid bacteria.

An inducible promoter may be induced (or activated) in the presence of an inducer or activator molecule, which may act directly or indirectly on the promoter, and which may be added to induce the promoter, or more generally to cause or enable induction or activation of the promoter, and permit expression of the protein, or it may be induced (or activated) by a change in conditions of the bacteria containing the plasmid, e.g. by introducing a change of conditions to the lactic acid bacteria, e.g. starvation or depletion of a particular nutrient. An inducer of the promoter may be encoded by a regulatory gene, which in an embodiment may itself be induced or activated. The term "inducer" is thus used broadly herein to include any regulatory molecule, or indeed any permissive condition, which may activate or turn on an inducible promoter, or allow or cause an inducible promoter to be induced. Thus, induction of an inducible promoter may comprise the introduction of (e.g. contacting the lactic acid bacteria containing the plasmid with) a regulatory molecule or of a condition permissive to promoter induction (activation). In some embodiments the inducer can be an activation peptide. This may act directly, or indirectly to induce the promoter, for example as described further below.

As noted above, promoters obtained or derived from lactic acid bacteria are preferred. These may be native promoters or modified or mutant promoters. A suitable promoter may for example be identified by growing lactic acid bacteria in a wound, and by determining which genes are expressed, or upregulated in the bacteria in the wound. The promoters from such genes may then be identified. Alternatively a number of different promoters and expression systems in or for use in lactic acid bacteria have been identified and described or available in the art, including expression plasmids containing such promoters or expression systems for use in LAB. Any such known plasmid or expression system may be used as the basis for the recombinant plasmid of the invention.

Various inducible expression systems are known in the art for use with LAB such as *Lactobacilli*. One example includes an auto-inducing system based on the manganese starvation-inducible promoter from the manganese transporter of *L. plantarum* NC8 as described in Ref. 19. This system does not require the addition of external inducers for recombinant protein production.

Duong et al. (Ref. 20) describe expression vectors for use with *lactobacilli* based on the broad range pWV01 replicon and containing promoters from operons involved in fructooligosaccharide (FOS), lactose or trehalose metabolism or transport, or in glycolysis. Such promoters may be induced by their specific carbohydrate and repressed by glucose.

More particularly, the inducible expression system may comprise inducible promoters involved in the production of LAB proteins, and in particular bacteriocins. The activity of such promoters may be controlled by a cognate regulatory system based on the bacteriocin regulon, for example a two-component regulatory (signal transduction) system which responds to an externally added activator peptide (i.e. an inducer/regulatory molecule in peptide form) and genes encoding a histidine protein kinase and response regulator necessary to activate this promoter upon induction by an activator peptide.

In an embodiment the expression system may be based on the nisin-controlled expression (NICE) system, based on the combination of the nisA promoter and the nisRK regulatory genes. This system is based on the promoters and regulatory genes from the *Lactococcus lactis* nisin gene cluster and has been used to develop regulated gene expression systems for *lactococci, lactobacilli* and other Gram-positive bacteria (reviewed briefly in Ref. 15 and Ref. 21). Whilst the NICE systems are efficient and well regulated in *Lactococci*, these systems can exhibit significant basal activity. This can be circumvented by integrating the histidine kinase and response regulator genes in the chromosome, limiting the expression systems to specially designed host strains.

In another embodiment the expression system may be based on the genes and promoter involved in the production of class II bacteriocins sakacin A (sap genes) by the sakacin A regulon or sakacin P (spp genes) by the sakacin P regulon. Such vectors are known as pSIP vectors and contain a promoter element derived from either the sakacin A or the sakacin P structural gene with an engineered NcoI site for translational fusion cloning. A variety of such vectors containing different promoters from the regulons and/or different replicons are described in Ref. 21 and Ref. 15 and any of these vectors could be used as the basis for the recombinant plasmid of the invention.

In a representative embodiment the promoter may be the $P_{sapA}$, $P_{sppA}$ or $P_{orfX}$ promoter from the sakacin A or P regulon, together with its associated or cognate regulatory genes.

In a particularly preferred embodiment the plasmid contains the pSH71 replicon, the $P_{orfX}$ promoter from the sakacin P regulon and the cognate regulatory genes, based on the vector pSIP411 depicted in FIG. 12 and described in Ref. 21. Plasmid pSIP411 is designated pLAB112 in the present application. The inducer for use in such an embodiment is preferably an activation peptide based on the peptide SppIP, e.g. an activation peptide having the sequence of SEQ ID NO: 19, or an amino acid sequence with at least 80% (or more particularly at least 85, 90 or 95) sequence identity thereto. In a preferred embodiment the said recombinant plasmid is derived from the plasmid designated pLAB112 having the nucleotide sequence shown in SEQ ID NO: 20.

The use of an inducible promoter (or inducible expression system) may provide the advantage of a more controlled, and in particular prolonged expression of the protein in the wound setting i.e. when the bacteria are administered to the subject or to the wound. For a better effect in promoting wound healing it is advantageous for the protein to be expressed by the bacteria for a period of time at the site of the wound (e.g. at the wound surface), e.g. for at least 40, 45, 50, 55 or 60 minutes, notably for at least one hour, or more. Thus the protein may be expressed for a finite, a defined or a prolonged period of time. Results presented in the Examples below show that using plasmids and bacteria according to the present invention, the protein may be expressed for a period of about an hour at the wound surface. The plasmids and bacteria may in some embodiments be optimised to allow expression of the protein (e.g. in a wound) for 2, 3 or 4 hours or more.

Continuous expression and delivery of the protein is thus desirable and this may be afforded by using the transformed bacteria of the invention. By "continuous" or "prolonged" is meant that there is expression, and hence delivery, of the protein over a period of time e.g. over a period of at least an hour (or so, as discussed above). In particular this allows the protein to be effective over a period of time which is increased as compared to administration of the protein directly (i.e. as a protein product rather than by expression by the bacteria).

As discussed above, the nucleotide sequences encoding the protein(s) may be codon optimised for expression in LAB. Accordingly, in preferred embodiments the nucleotide sequences (or inserts) in the recombinant plasmids, which encode the proteins, may be selected from the codon-optimised nucleotide sequences shown in SEQ ID NOS. 1, 4, 7, 10, 13 and 16 which encode murine CXCL12, human CXCL12, murine CXCL17, human CXCL17, murine Ym1 and human Ym1 respectively, or a nucleotide sequence having at least 80% sequence identity therewith.

Thus in representative embodiments the recombinant plasmid may be chosen from the group consisting of the plasmids designated mLrCK1, comprising a nucleotide sequence as shown in SEQ ID NO: 1; mLrCK1.4, comprising a nucleotide sequence as shown in SEQ ID NO: 1; mLrCK1.7, comprising a nucleotide sequence as shown in SEQ ID NO: 1; hLrCK1, comprising a nucleotide sequence as shown in SEQ ID NO: 4; mLrCK2, comprising a nucleotide sequence as shown in SEQ ID NO: 7; hLrCK2, comprising a nucleotide sequence as shown in SEQ ID NO: 10; hLrMP1, comprising a nucleotide sequence as shown in SEQ ID NO: 13; and mLrMP2, comprising a nucleotide sequence as shown in SEQ ID NO: 16.

In some embodiments the plasmid of the invention comprises a nucleotide sequence which has at least 80%, 81%, 82%, 83%, 84%, 85%, 86%, 87%, 88%, 89% 90%, 91% 92% 93%, 94%, 95%, 96%, 97%, 98% or 99% sequence identity to a nucleotide sequence of the following codon optimised inserts mLrCK1 (i.e., to the nucleotide sequence of SEQ ID NO: 1), mLrCK1.4 (i.e., to the nucleotide sequence of SEQ ID NO: 1), mLrCK1.7 (i.e., to the nucleotide sequence of SEQ ID NO: 1), hLrCK1 (i.e., to the nucleotide sequence of SEQ ID NO: 4), mLrCK2 (i.e., to the nucleotide sequence of SEQ ID NO: 7), hLrCK2 (i.e., to the nucleotide sequence of SEQ ID NO: 10), hLrMP1 (i.e., to the nucleotide sequence of SEQ ID NO: 13), and mLrMP2 (i.e., to the nucleotide sequence of SEQ ID NO: 16).

Sequence identity of nucleotide molecules may be determined by methods and software known and widely available in the art, for example by FASTA Search using GCG packages, with default values and a variable pamfactor, and gap creation penalty set at 12.0 and gap extension penalty set at 4.0 with a window of 6 nucleotides.

Such sequence identity related nucleotide sequences may be functionally equivalent to the nucleotide sequence which is set forth in SEQ ID NO: 1, 4, 10, 13 or 16. Such nucleotide sequences may be considered functionally equivalent if they encode polypeptides which would be considered functional equivalents to the respective CXCL12, CXCL17 or Ym1 proteins. Preferred functional equivalents are those which encode the preferred proteins as set out above.

In another aspect, the invention provides a bacterial strain transformed with the recombinant plasmid described above. The said bacterial strain is preferably a lactic acid bacteria strain such as a *Lactobacillus* strain or a *Lactococcus* (e.g. *Lactococcus lactis*) strain. More preferably, the bacterial strain is a *Lactobacillus reuteri* strain such as *Lactobacillus reuteri* R2LC or *Lactobacillus reuteri* DSM20016. The said strains (*Lactobacillus reuteri* R2LC/DSM20016 and *Lactococcus lactis*) are not found on human skin as determined by phylogenetic analysis of the forearm skin biota of six subjects (Ref. 13).

As well as the plasmids, expression systems, bacteria and kits, further products of the invention include pharmaceutical compositions and medical devices containing the bacteria. Such compositions and devices may include in particular wound dressings, packing materials, swabs, implants etc., or indeed any wholly or partially in-dwelling medical device which may be introduced or present at the site of a wound (e.g. at a surgical wound site), for example a line or catheter or implant. Also included are probiotic products, that is products containing the bacteria for administration to a subject, e.g. for oral administration, for example for consumption or ingestion, or for topical application to a wound or direct administration to a wound site, e.g. during surgery, or rectally, vaginally, etc.

Accordingly, the products (e.g. plasmids, bacterial strains, probiotics and wound dressings etc.) according to the invention are useful in medical therapy, in particular for promoting wound healing in human or animal subjects. As used herein, the term "promoting wound healing" means augmenting, improving, increasing, or inducing closure, healing, or repair of a wound. In preferred aspects of the invention, the human or animal subject is in need of wound healing due to an underlying medical condition leading to impaired wound healing, such as reduced peripheral blood perfusion (peripheral artery disease), hyperglycemia or neuropathy, or the subject may be immunocompromised for any reason, e.g. due to an underlying disease (whether acquired or inherited) or as an effect of medical treatment. In particular the subject may be suffering from diabetes.

The wound to be healed can include any injury, trauma or damage to any portion of the body of a subject. Examples of wounds that can be treated by the method include acute conditions or wounds; such as thermal burns (hot or cold), chemical burns, radiation burns, electrical burns, burns caused by excess exposure to ultraviolet radiation (e.g. sunburn); damage to bodily tissues, such as the perineum as a result of labor and childbirth; injuries sustained during medical procedures, such as episiotomies, trauma-induced injuries including cuts, incisions, excoriations; injuries sustained from accidents; post-surgical injuries, as well as chronic conditions; such as pressure sores, bedsores, ulcers, conditions related to diabetes and poor circulation, and all types of acne. In addition, the wound can include dermatitis, wounds following dental surgery; periodontal disease; wounds following trauma; and tumor associated wounds. Further examples are gastrointestinal wounds occurring during for instance gastritis or inflammatory bowel disease.

Thus the term "wound" is used broadly herein to include any breach of the integrity of a tissue or any damage or injury to a tissue. Thus the term includes any damage, trauma or injury to tissue or any lesion, howsoever caused (e.g. due to accidental injury or trauma, surgical or other intended or purposeful injury or disease). The trauma may include any physical or mechanical injury or any damage caused by an external agent including pathogens or biological or chemical agents. Tissue damage may also be caused by hypoxia, ischemia or reperfusion. Wounds may include any type of burn. The wound may be acute or chronic. A chronic wound may be described as any wound stalled in a healing stage, e.g. in the inflammatory phase, or any wound that has not healed in 30, 40, 50 or 60 days or more. The wound may be present in or on an internal or external surface or tissue of the body.

In a particular embodiment the wound is on an external surface or tissue of the body, e.g. it is a skin (i.e. cutaneous) wound or a mucosal wound, in particular a wound in an external mucosal tissue or surface of the body (e.g. in the eye, ear or nose etc.) In another embodiment it is a gastrointestinal wound. In a different embodiment it is not a gastrointestinal wound (i.e. it is a wound other than a gastrointestinal wound).

The bacteria may be administered in any convenient or desired way, e.g. orally, or topically, or by direct administration to a wound site e.g. by direct injection or infusion or application or introduction of a pharmaceutical composition or dressing or device containing the bacteria. In other embodiments it may be administered to the oral cavity, or intranasally or by inhalation, rectally or vaginally. The bacteria may thus be administered to, or via, any orifice of the body. For administration to a gastrointestinal wound the bacteria may be administered perorally.

The bacteria may be formulated or prepared in any convenient or desired way for administration by any of the above routes, according to procedures and using means well known and routine in the art. Thus, as well as pharmaceutical compositions, medical devices and dressings etc., the probiotic products of the invention may be formulated and provided as or in nutritional supplements or foods, e.g. functional foods.

Oral administration forms include powders, tablets, capsules and liquids etc. For topical administration, the product may be formulated as a liquid e.g. a suspension, or a spray or aerosol (powder or liquid), gel, cream, lotion, paste, ointment or salve etc. or as any form of dressing, e.g. bandage, plaster, pad, strip, swab, sponge, mat etc., with or without a solid support or substrate. Further the bacteria may be provided on (e.g. coated on) the surface of a medical device such as an implant (e.g. a prosthetic implant), tube, line or catheter etc.

The bacteria may be provided in any convenient or desired form, e.g. as an active or growing culture or in lyophilized or freeze-dried form.

The bacterial strains according to the invention can be formulated for topical or oral administration to treat surface wounds of skin or mucosa. Consequently, the invention further provides a probiotic product comprising a bacterial strain according to the invention. The said probiotic product is e.g. a pharmaceutical composition, preferably for oral administration. Alternatively, for topical application, the probiotic product is e.g. a lotion or a lotion-soaked wound dressing, comprising a bacterial strain according to the invention.

The product of the invention (i.e. the pharmaceutical composition or device or dressing etc.) may also contain the inducer (where an inducible promoter is used). This may be provided as part of the product (e.g. incorporated into or included in a dressing) or separately, e.g. as part of a kit or combination product, as defined above.

When co-formulated together in a product (e.g. a dressing or device) the bacteria and the inducer may be provided in a format in which the bacteria are separated from the inducer and are brought together (or contacted) in use. For example, the bacteria and inducer may be in separate compartments which are brought together (e.g. contacted or mixed), or may be separated by a barrier (e.g. a membrane or other partition) which may be broken or disrupted or opened in use.

Alternatively, the inducer may be formulated and provided separately (e.g. in a kit also containing the bacteria, or a product containing the bacteria), and the inducer and bacteria (or product containing the bacteria) may be brought together (e.g contacted) during use. This may be before, during or after administration to the subject. For example, a product comprising the bacteria may be administered first and then the inducer may be added or applied to the bacteria. In another embodiment the bacteria and inducer may be premixed before administration, e.g. just before or immediately before, or during administration.

Where bacteria are provided in lyophilized or freeze-dried form, it may be desirable to reconstitute, or resuspend, them prior to administration e.g. prior to or during use. This may depend on the wound and the format of the product which is used. For example, in the case of some wounds there may be sufficient liquid present to allow for the bacteria to be reconstituted/resuspended and become active. However, in other embodiments it may be desirable to provide a liquid for reconstitution (or alternatively expressed, for suspension or resuspension) of the bacteria. This may be provided in a separate vessel or container (e.g. as part of a kit or combination product) or in a separate compartment of a container, or vessel or device. The liquid may comprise or contain the inducer, or the inducer, when present, may be provided in a separate vessel or container or compartment. The liquid may be any suitable liquid for reconstitution or suspension of freeze-dried bacteria, e.g. water, or an aqueous solution, or buffer or growth or culture medium.

Thus, by way of example a two compartment system (e.g. in a dressing or device or container or vessel (e.g. a bottle)) may comprise freeze-dried bacteria in one compartment and a liquid in another. The liquid may optionally contain an inducer. In use, or prior to use, the two compartments may be mixed or brought into contact, and applied to the wound. In a more particular embodiment, the bacteria may be administered to a wound in liquid form, and a separate dressing may then be applied. It will be seen therefore that in one simple embodiment, a kit may simply contain a first vessel or container comprising the freeze-dried bacteria and a second vessel or container containing a liquid for reconstitution of the bacteria. Optionally the kit may also contain an inducer, which is also contained in the second vessel or in separate third vessel or container.

Hence, for example a said probiotic product preferably comprises an activation peptide capable of activating expression of the protein to be expressed in the lactic acid bacteria strain. The said activation peptide is preferably the peptide SppIP (i.e. a peptide comprising the amino acid sequence of SEQ ID NO: 19, or a sequence with at least 80% sequence identity thereto).

For cutaneous wounds, the said wound dressing can comprise freeze-dried bacteria in one compartment and an activation peptide in another compartment. When applied to the wound, the two compartments are brought together so that the bacteria are brought into contact with the activation peptide. Alternatively, bacteria can be contained in a gel-like structure on the adhesive side of a waterproof plaster or the side of the dressing in contact with the exudate. At the time of use, activation peptide is manually applied to the bacteria and the plaster or dressing is applied to the wound area.

Viable bacteria may also be comprised in a hydrocolloid, for example a natural gelatin. The bacteria can be incorporated by crosslinking into hydrocolloid e.g. gelatin films, plasticised and dried, retaining viability during storage until hydration. Viable bacteria may also be encapsulated within cross-linked electrospun hydrogel fibers. In this format the bacteria need not be freeze-dried.

For wounds in the gastrointestinal tract, a tablet is designed comprising at least two separate compartments, wherein one compartment comprises freeze-dried bacteria and the other compartment comprises liquid and an activation peptide. The tablet is squeezed before ingestion so that an inner membrane, separating the two compartments, is broken and the contents are mixed together. For wounds in the mouth (e.g. on the gums), bacteria according to the invention can be administered in a high viscous paste.

Specifically, formulations for topical administration to the skin can include ointments, creams, gels, and pastes to be administered in a pharmaceutically acceptable carrier. Topical formulations can be prepared using oleaginous or water-soluble ointment bases, as is well known to those in the art. For example, these formulations may include vegetable oils, animal fats, and more preferably semisolid hydrocarbons obtained from petroleum. Particular components used may include white ointment, yellow ointment, acetyl esters wax, oleic acid, olive oil, paraffin, petrolatum, white petrolatum, spermaceti, starch glycerite, white wax, yellow wax, lanolin, anhydrous lanolin, and glyceryl monostearate. Various water-soluble ointment bases may also be used including, for example, glycol ethers and derivatives, polyethylene glycols, polyoxyl 40 stearate, and polysorbates.

The bacterial strain can be provided in and/or on a substrate, solid support, and/or wound dressing for delivery of active substances to the wound. The solid support or substrate may be a medical device or a part thereof. As used herein, the term "substrate" or "solid support" and "wound dressing" refer broadly to any substrate when prepared for, and applied to, a wound for protection, absorbance, drainage, etc.

In an embodiment the invention provides a wound healing material or dressing attached to or comprising the transformed bacterial strain i.e. the dressing is a vehicle for administering the transformed bacteria of the invention. Alternatively the vehicle may be a plaster or bandage. The present invention may include any one of the numerous types of substrates and/or backings that are commercially available, the choice of wound healing material will depend on the nature of the wound to be treated. The most commonly used wound dressings are described briefly below.

Transparent film dressings are made of e.g. polyurethane, polyamide, or gelatin. These synthetic films are permeable to water vapor oxygen and other gases but impermeable to water and bacteria, have low absorbency and are suitable for wounds with low exudate), hydrocolloids (hydrophilic colloidal particles bound to polyurethane foam), hydrogels (cross-linked polymers containing about at least 60% water have higher absorbency and eliminate toxic components from the wound bed and maintain the moisture level and temperature in the wound area), foams (hydrophilic or hydrophobic e.g. polymeric foam dressings produced through the modification of polyurethane foam have good absorbency and are permeable to water vapour), calcium alginates (non-woven composites of fibers from calcium alginate from the phycocolloid group, alginates have a very high absorbent capacity. They also promote autolytic debridement because ion-exchange between the alginate and the exudate converts the insoluble calcium alginate into soluble sodium alginate, providing the wound bed with a moist, intact surface ideal for wound healing), and cellophane (cellulose with a plasticizer). The shape and size of a wound may be determined and the wound dressing customized for the exact site based on the measurements provided for the wound. As wound sites can vary in terms of mechanical strength, thickness, sensitivity, etc., the substrate can be molded to specifically address the mechanical and/or other needs of the site. For example, the thickness of the substrate may be minimized for locations that are highly innervated, e.g. the fingertips. Other wound sites, e.g. fingers, ankles, knees, elbows and the like, may be exposed to higher mechanical stress and require multiple layers of the substrate.

In yet a further aspect, the invention provides a method for wound healing in a human or animal subject, comprising administering to a human or animal subject in need thereof a bacterial strain according to the invention. The said bacterial strain is preferably comprised in a pharmaceutical composition or wound dressing as hereinbefore described. In such methods, the human or animal subject is preferably in need of wound healing due to an underlying medical condition leading to impaired wound healing, such as reduced peripheral blood perfusion (peripheral artery disease), hyperglycemia or neuropathy.

Results obtained and included in the Examples below demonstrate the advantages of the invention. In particular, improved wound healing (e.g. in terms of better or faster wound closure) may be obtained by using the protein-expressing transformed bacteria of the invention, as compared to, for example, a protein preparation directly (i.e. just the protein, no bacteria) or just bacteria alone (bacteria which are not modified to express the protein, e.g. not containing the recombinant plasmid). Further, an improved effect may be seen when bacteria are administered to wound, compared to administration of a supernatant obtained from a transformed bacterial culture. It is thus advantageous to deliver the protein to the wound by means of a lactic acid bacterial host expressing the protein. It is believed that there may be synergistic effect. In other words there may be a synergy between the effect of the bacteria and the effect of the protein on wound healing. Accordingly, in some embodiments there may be a greater than cumulative effect of the transformed bacteria on wound healing, relative to the effect of corresponding untransformed bacteria (i.e. not containing the plasmid) and the effect of the protein when provided as a protein (i.e. not expressed from bacteria in situ).

It is believed in this respect that the effect of the bacteria in lowering pH e.g. in the site of the wound may assist in augmenting or enhancing or promoting the activity of the protein. Whilst not wishing to be bound by theory, it is further believed that administration of the transformed bacteria according to the invention may have a beneficial effect in promoting macrophage activity at the site of the wound. For example, the number of macrophages may be increased.

The effect of the transformed bacteria on wound healing may or may not be immediate, and may take some time to be seen (e.g. 1, 2, 3, 4, 5 or 6 or more hours to be seen, or longer, e.g. 8, 10, 12, 15, 18, 20 or 24 hours or more, or 1, 2, 3, 4, 5 or 6 or more days to be seen, or longer e.g. 8, 10, 12, 15, 18, 20 or 24 days or more, before improved wound healing can be observed). For chronic wounds in elderly humans it may take longer to see a difference between the treatment group and control group for example it may take around 12 weeks.

A particular and important utility of the present invention lies in the treatment of chronic wounds, particularly ulcers and in particular in the treatment of diabetic foot ulcers.

The prevalence of chronic foot ulcers in persons with diabetes is about 18%. In 2013, the European population reached 742.5 million, which translates into 32.7 million with diabetes, of which 2.9-5.8 million have chronic foot ulcers. Mean duration of an ulcer of this type is in the range of months where less than 25% of the wounds are healed within 12 weeks when standard care is given. The end stage of this condition is amputation of the affected limb. Today the treatment of people having chronic foot ulcers is divided between primary care, home care, nursing homes, relatives, self-management and visits to hospital wound clinics. The current treatment relies on off-loading, removal of dead tissue using surgical debridement, repeated changes of wound dressings, systemic antibiotics and in special cases treatment with living larvae or collagenase and at a few locations in Sweden hyperbaric oxygen treatment can be offered. If an underlying cause also includes obstructions of larger arteries, this can be corrected surgically by bypassing vein graft. Today the wounds are treated every second to third day. Treatment with the suggested modified lactic acid bacteria in any of the suggested forms or formulations would not disrupt this practical routine. Improved healing of such wounds by the treatments of the present invention would thus be of considerable economic benefit, as well as of personal benefit to the patient.

The bacteria are active and produce and deliver the encoded proteins to the wound surface for a period of time (e.g. about one hour) in vivo. They may then become inactive and die. Slow or dead lactic acid bacteria can with no risk be in the wound/dressing environment until the dressing is changed as normal.

The biotherapeutic according to the present invention will have significantly lower production cost compared to protein drug compounds. This is because the biotherapeutics produces the active protein itself directly in the wound.

Open wounds such as diabetic foot ulcers, together with loss of function in the foot, cause considerable discomfort, and even disability to the patient, and can have a significant negative impact on quality of life, including significant risk or infection and therefore prolonged use of antibiotics, and ultimately amputation. Improved healing would thus be of tremendous personal benefit to the patient and would also have the benefit of reducing antibiotic use (and consequently the spread of antibiotic resistance). It is believed that treating such chronic wounds according to the invention may amplify endogenous alarm signals in the wound, and kick start the healing process in stalled or chronic wounds, and accelerate healing time.

Further, the invention may have advantages in flexibility and ease of use by medical staff.

BRIEF DESCRIPTION OF THE DRAWINGS

Representative methods and preferred embodiments according to the present invention will be further described with reference to the following non-limiting Examples and Figures in which:

FIGS. 4A, 4B, 4C, One-way ANOVA, Bonferroni compare all columns.

FIG. 5A, Two-way ANOVA, Bonferroni compare all columns, d0-d5 analyzed. Change due to time and treatment. Decreased wound size by R2LC_pLAB112_LrCK1.4 at d1 and d2 compared to Controls. FIG. 5B, One-way ANOVA, Bonferroni compare all columns, all days analyzed. Decreased wound exposure by R2LC_pLAB112_LrCK1.4 for the whole healing process.

FIGS. 7A, 7B & 7C, One-way ANOVA, Bonferroni compare all columns.

FIG. 8A, Two-way ANOVA, Bonferroni compare all columns, d0-d7 analyzed. Change due to time and treatment. Decreased wound size R2LC_pLAB112_LrCK1.4 at d1 and d2 compared to Controls. FIG. 8B, One-way ANOVA, Bonferroni compare all columns, all days analyzed. Decreased wound exposure by R2LC_pLAB112_LrCK1.4 for the whole healing process.

FIGS. 9A and 9B, Two-way ANOVA, Bonferroni compare all columns, d0-d6 analyzed. No change was observed due to time or treatment.

FIGS. 10A, 10B & 10C, One-way ANOVA, Bonferroni compare all columns.

FIG. 11A, Two-way ANOVA, Bonferroni compare all columns, d0-d6 analyzed. Change due to time. FIG. 11B, One-way ANOVA, Bonferroni compare all columns, all days analyzed. No diff. (p=0.08).

FIGS. 14A, 14B & 14C, Students unpaired two-tailed t-test.

(FIG. 15A) Two-way ANOVA, Bonferroni compare all columns, d0-d7 analyzed. Change due to time. (FIG. 15B) Students two-tailed unpaired t-test. Tendency (p=0.08) to decreased wound exposure by pCXCL12 for the whole healing process.

FIG. 16. Measurements of bacterial concentrations for Lactobacillus reuteri R2LC expressed as optical density (OD) and colony forming units per ml (CFU/ml).

FIGS. 17A & 17B. Wound size (FIG. 17A) and wound exposure (FIG. 17B) over time in healthy mice treated with different concentrations of Lactobacillus reuteri R2LC_pLAB112_LrCK1.4. Wound size measured daily from images with a scale included. FIG. 17A, Two-way ANOVA, Bonferroni compare all columns, d0-d2 analyzed. Change due to time and treatment. (FIG. 17A) Two way ANOVA Bonferroni compare all columns, (FIG. 17B) One Way ANOVA Bonferroni compare all columns (p<0.05). Decreased wound exposure by treatment with Lactobacillus reuteri R2LC_pLAB112_LrCK1.4 at OD 0.2, 0.5, 1.0 and 1.25 as compared to wound receiving no treatment. (Control, n=15; OD 0.2, n=4; 0.5, n=10, OD 1.0, n=4; OD 1.25, n=5).

FIG. 18A, Two-way ANOVA, Bonferroni compare all columns, d0-d2 analyzed. Change due to time. FIG. 18B, wound exposure the first two days. (Control, n=15; 0.2 μg CXCL12 1α, n=4; 0.6 μg CXCL12 1α, n=5, 1.0 μg CXCL12 1α, n=4).

FIG. 19A, Two-way ANOVA, Bonferroni compare all columns, d0-d2 analyzed. Change due to time. FIG. 19B, wound exposure the first two days. (No treatment, n=15; CXCL12 1α, n=6; CXCL17, n=9, Ym1, n=9).

FIG. 20A shows pH measured in culture medium after 24 hours of culturing skin discs with epidermal wounds with no treatment or treatment with LB_Luc or LB_LrCK1. FIG. 20B shows length of the newly formed epidermis sleeve growing from the wound edge over the exposed dermis after 14 days of culture. * indicates difference, One Way ANOVA Bonferroni compare selected columns (p<0.05).

(FIG. 23A) Two-way ANOVA, Bonferroni compare all columns, d0-d2 analyzed. Change due to time and treatment. (FIG. 23B) One Way ANOVA Bonferroni compare all columns (p<0.05). Decreased wound size was observed following treatment with Lactobacillus reuteri R2LC_pLAB112_LrCK1.4 compared to Lactobacillus reuteri R2LC_pLAB112_Luc also when the bacteria had been freeze-dried and directly revived, induced and applied to wounds (R2LC_pLAB112_Luc, n=4, R2LC_pLAB112_LrCK1.4, n=5).

EXAMPLES

Materials and Methods

Gene Construct Design and Production

Figure 1A:
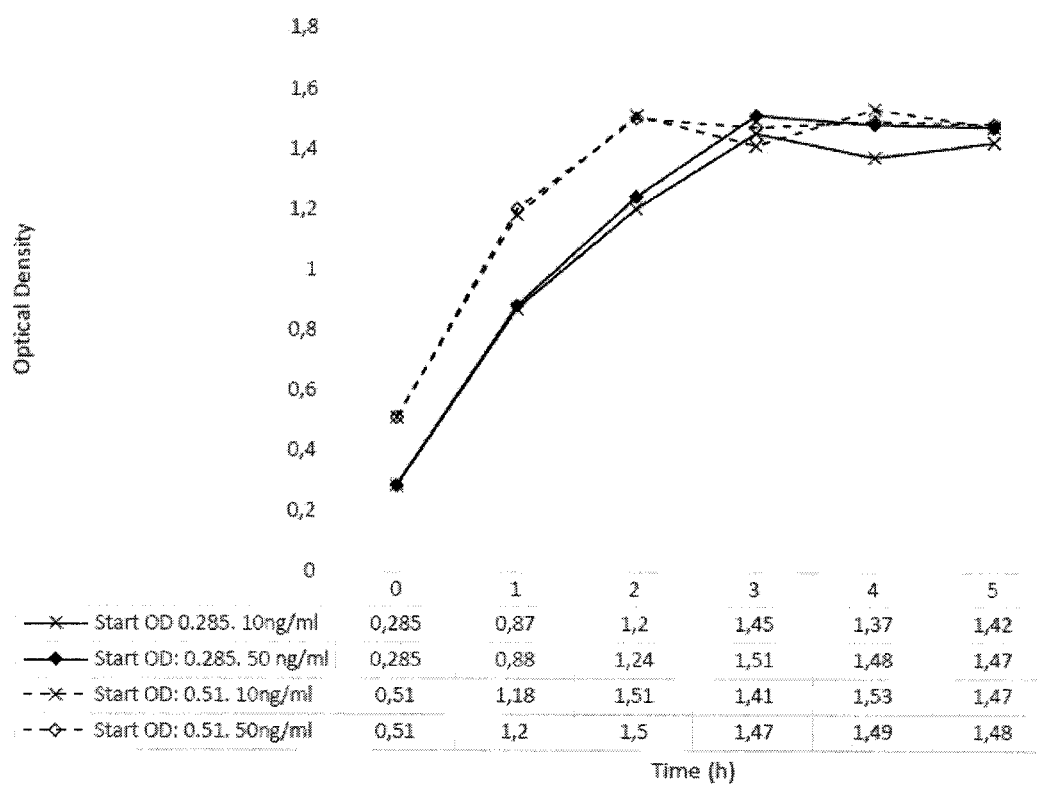
FIGS. 1A & 1B. Growth (FIG. 1A) and pH (FIG. 1B) over time in mLrCK1 *Lactococcus lactis* re-inoculated from overnight culture at start OD 0.285 and 0.51 with addition of 10 or 50 ng/ml promoter activation peptide SppIP.

The plasmid backbone pLAB112 (equal to pSIP411; Refs. 11 and 15; Table I) was provided by Professor Lars Axelsson (Norwegian Food Research Institute). *Lactococcus lactis* MG1363 bacteria was transformed with pLAB112 and expanded for 24 hours. The plasmid was then purified and the DNA product was verified on a gel.

TABLE I

| Main features of pSIP411/pLAB112 | |
|---|---|
| Feature | Positions (SEQ ID NO: 20) |
| Replication determinant (replicon region) | 260-2010 |
| ermB (erythromycin resistance marker) | 2342-2840 |
| $P_{spp}IP$ (inducible promoter) | 3139-3290 |
| sppK (histidine protein kinase) | 3305-4647 |
| sppR (response regulator) | 4653-5396 |
| gusA (beta-glucuronidase) | 5853-7658 |
| $P_{orf}X$ (inducible promoter) | 5689-5835 |
| Transcriptional terminators | 129-155; 5428-5460; 5602-5624 |
| Multicloning sites | 1-35; 5851-5856; 7662-7673 |

The sequence for murine CXCL12-1α was optimized for translation in *Lactobacillus reuteri* by Stefan Roos at the Swedish University of Agricultural Sciences (SLU) using DNA2.0 (Menlo Park, Calif., USA). The optimized sequence (SEQ ID NO: 1) was synthesized by DNA 2.0 in plasmid vector pJ204. The sequences for human CXCL12-1α, murine CXCL17, human CXCL17, murine Ym1 and human Ym1 were optimized for translation in *Lactobacillus*

*reuteri* by Stefan Roos at SLU using GenScript (Piscataway, N.J., USA). The optimized sequences are shown as SEQ ID NO: 4 (human CXCL12-1α); SEQ ID NO: 7 (murine CXCL17); SEQ ID NO: 10 (human CXCL17); SEQ ID NO: 13 (murine Ym1); and SEQ ID NO: 16 (human Ym1).

Primers were designed to detect the insert (hCXCL12opt), 171 bp in pLAB112:

| | |
|---|---|
| 5'GCAGCCTTAACAGTCGGCACCT3'; | (SEQ ID NO: 22) |
| 5'ACGTGCAACAATCTGCAAAGCAC3'. | (SEQ ID NO: 23) |

The ends of the insert were also optimized for continuing the molecular processing so the insert would fit in the new vector pLAB112. The optimized mCXCL12opt sequence was delivered in a plasmid PJ204. *E. coli* PK401 was transformed with pJ204. Plasmids (pLAB112 and pJ204) were cleaved with the restriction enzymes XhoI and NcoI in NEB2 buffer. The fragment mCXCL12opt was then purified on a gel. The mCXCL12opt insert was then ligated into the pLAB112 vector using T4 DNA ligase, resulting in the construct mLrCK1. The insert construct in the pLAB112 vector was verified by PCR. The construct was then verified by sequence analysis (Macrogen). Finally *Lactobacillus reuteri* strain R2LC and DSM 20016 was transformed with mLrCK1 and two R2LC clones (4 and 7) positive for the construct were collected and the plasmid mLrCK1 (now mLrCK1.4 and mLrCK1.7) from these colonies were again verified by sequence analysis (Macrogen).

The plasmids hLrCK1, mLrCK2, hLrCK2, mLrMP1 and hLrMP2 were produced in an analogous way following the same protocol and procedure (See Table II below).

TABLE II

Overview of plasmids

| Plasmid | Description |
|---|---|
| pLAB112 | Identical with pSIP411 (Ref. 15 and SEQ ID NO: 20) |
| mLrCK1 | pLAB112 with optimized mCXCL12-1α insert |
| mLrCK1.4 | mLrCK1 from transformed *Lactobacillus reuteri* R2LC clone 4 |
| mLrCK1.7 | mLrCK1 from transformed *Lactobacillus reuteri* R2LC clone 7 |
| hLrCK1 | pLAB112 with optimized hCXCL12-1α insert |
| mLrCK2 | pLAB112 with optimized mCXCL17 insert |
| hLrCK2 | pLAB112 with optimized hCXCL17 insert |
| hLrMP1 | pLAB112 with optimized human Ym1 insert |
| mLrMP2 | pLAB112 with optimized murine Ym1 insert |
| pLAB112_Luc | pLAB112 with luciferase insert |

In Vitro Analysis of Plasmid Expression

*Lactobacillus reuteri* R2LC pLAB112_Luc cultured overnight, re-inoculated and grown to OD 0.5 were plated (200 μl/well) on a 96 well plate or immediately resuspended from freeze-dried formulation. Luminescence intensity was determined using non-invasive bioimaging (IVIS Spectrum, Perkin Elmer). A baseline image at time 0 was acquired. Then activation peptide SppIP (50 ng/ml) and D-Luciferin (150 μg/ml) was added immediately after. The plate was then imaged at 5 minutes and then every $30^{th}$ minute for 1400 minutes. Data was quantified using Living Image 3.1 software (Perkin Elmer) and imaging parameters were maintained for comparative analysis. Radiance was considered proportional to plasmid expression.

Animals

Experiments were approved by Uppsala Regional Laboratory Animal Ethical Committee. Mice, C57Bl/6 (Taconic) and CX3CR1$^{+/GFP}$ on C57Bl/6 background (originally from The Jackson Laboratory) were used. Animals had free access to water and chow throughout experiments.

Wound Induction

Mice were anesthetized (1-3% isoflurane, 200 ml/min) and hair was removed on the hind limb by shaving and then by 1 min application of hair removal cream (Veet®) that were rinsed off with water. A sterile punch biopsy needle (5 mm diameter) was used to induce full-thickness (epidermis, dermis and subcutis) wounds. Local topical analgesic (Embla cream) was applied daily for the first 5 days.

Topical Wound Treatments

Wounds were treated daily with either 25 μl saline, *Lactobacillus reuteri* R2LC pLAB112_Luc or R2LC pLAB112_LrCK1. Bacteria was cultured overnight, re-inoculated and grown to OD 0.5, preactivated 5 min prior to application with activation peptide SppIP (50 ng/ml) and added topically to the middle of the wound surface. For dosing experiments wounds were treated daily for two days with either 25 μl saline or *Lactobacillus reuteri* R2LC pLAB112_LrCK1 re-inoculated from overnight culture and grown to OD 0.5, preactivated 5 min prior to application with activation peptide SppIP (50 ng/ml) and added topically to the middle of the wound surface at concentrations of OD 0.2, 0.5, 1.0 or 1.25. For comparative experiments with the respective proteins wounds were treated daily with either 10 μl saline or murine CXCL12, CXCL17 or Ym1 (total of 200 ng protein in 60 μl saline given in 10 min intervals for one hour). For a dose escalation study of CXCL12 200 ng, 600 ng or 1 μg was added to the wound in 10 μl saline at one time point once per day.

In Vivo Analysis of Plasmid Expression

*Lactobacillus reuteri* R2LC pLAB112_Luc were cultured overnight, re-inoculated and grown to OD 0.5. Luminescence intensity was determined using non-invasive bioimaging (IVIS Spectrum, Perkin Elmer). A baseline image at time 0 was acquired. Then 25 μl *Lactobacillus reuteri* R2LC pLAB112_Luc was added in the middle of the wound. Bacteria was preactivated 5 min prior to application with activation peptide SppIP (50 ng/ml) and D-Luciferin (150 μg/ml). Mice were the imaged every $15^{th}$ minute for 270 minutes. Data was quantified using Living Image 3.1 software (Perkin Elmer) and imaging parameters were maintained for comparative analysis. Radiance was considered proportional to plasmid expression.

Wound Size and Appearance Monitoring

The size and appearance of the wounds were monitored daily in anesthetized mice (1-3% isoflurane, 200 ml/min) by acquisition of conventional photos. A scale was included in the image at acquisition and wound size was analyzed using ImageJ (Free software from NIH). Wounds were considered healed when <0.5 mm$^2$ in size.

Cutaneous Blood Flow Monitoring

Blood flow in the whole hind limb with the healing wound was measured in anesthetized (1-3% isoflurane, 200 ml/min) mice using noninvasive Laser Speckle Contrast Analysis and data was analyzed, PIMSoft 3 (Perimed). Limbs (Frame 1.4×1.4 cm) were imaged for 2 minutes at 10 images/s with averaging by 20. Data is expressed in perfusion units (PFU).

Reduction of Perfusion

Mice were anesthetized (1-3% isoflurane, 200 ml/min) and hind limb ischemia was induced by ligation and excision of the femoral artery above the superficial epigastric artery branch.

Induction of Hyperglycemia

A single dose of alloxan monohydrate (8 mg/ml, 1 μl/g body weight) immediately dissolved in sterile saline was injected in the tail vein. Blood glucose and body weight was monitored daily throughout the experiment. Hyperglycemia was defined as blood glucose>16.7 mmol/l.

Statistical Analysis

Data are presented as mean±SEM. Two-Way ANOVA with Bonferroni compare all columns post hoc test was used analyzing the healing process over time. One-Way ANOVA with Bonferroni compare all columns post hoc test was used analyzing the healing process at one time point in groups of n>2 and Students two-tailed unpaired t-test was used analyzing the healing process at one time point when n=2. p<0.05 was considered statistically significant.

Example 1: Growth of Bacteria Transformed with Plasmid LrCK1

Figure 1B:
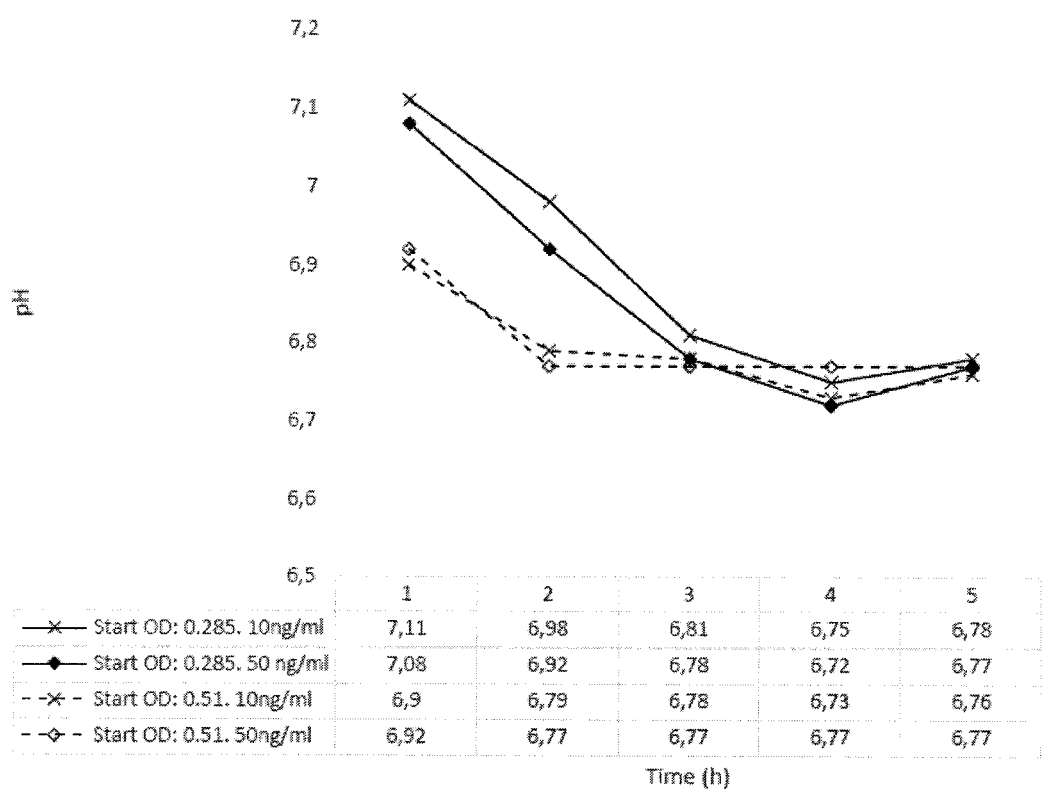

*Lactococcus lactis* with mLrCK1 cultured overnight, re-inoculated and grown to OD 0.3 or 0.5 showed no growth impairment when the activation peptide SppIP (SEQ ID NO: 19) were added at either 10 or 50 ng/ml. During these growth experiments pH was measured and the lowering was most accentuated in the growth phase and then stabilized around pH 6.7 when grown is Mes-medium (FIGS. 1A & 1B). (pH of skin=5,5, pH in wounds=7.15-8.9 where alkaline pH correlates with lower healing rate (Ref. 14))

Example 2: Expression of Plasmid pLAB112 Luc

Figure 2:
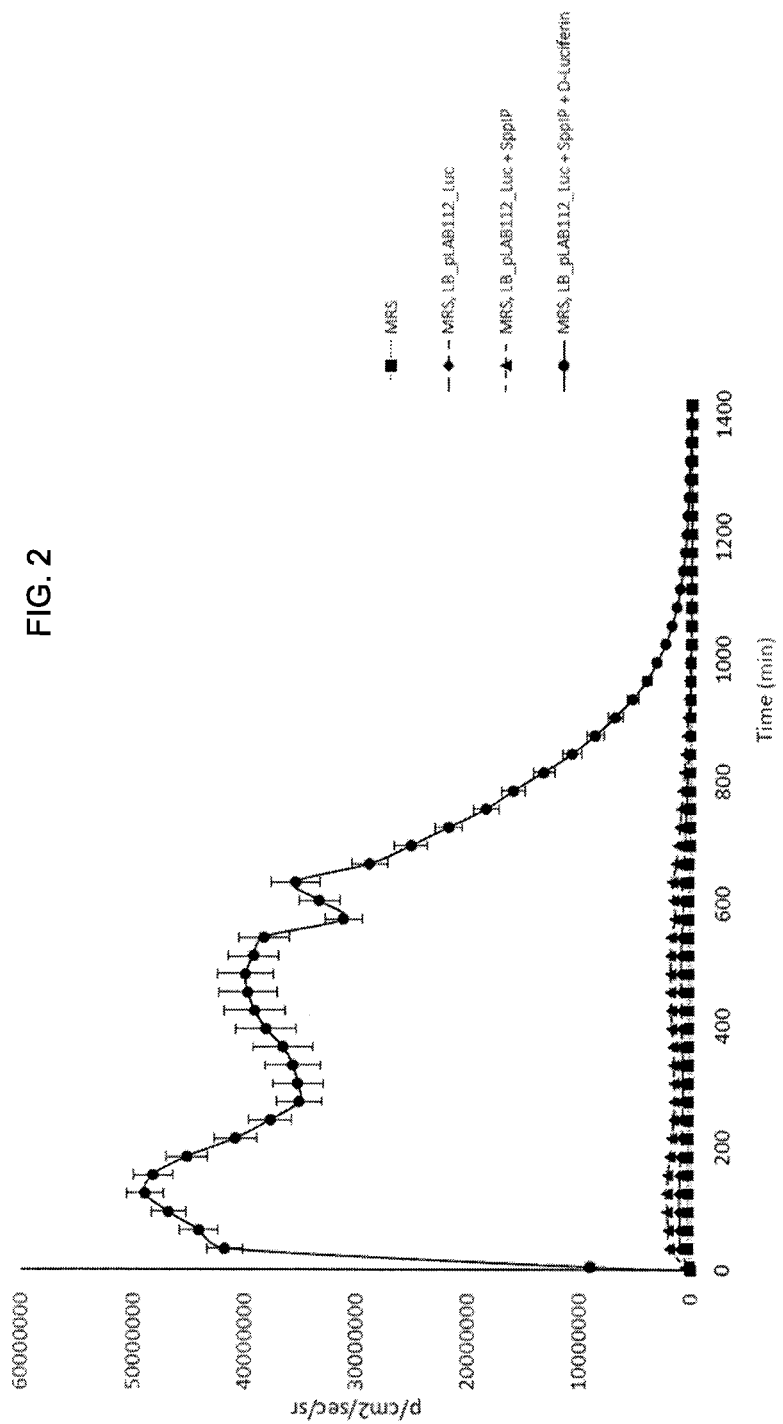
FIG. 2. Expression of pLAB112_Luc in *Lactobacillus reuteri* R2LC re-inoculated from overnight culture at start OD 0.5 in vitro measured by bioimaging over time. A baseline image at time 0 was acquired. Promoter activation peptide SppIP (50 ng/ml) and substrate D-Luciferin (150 µg/ml) were added immediately after. The plate was imaged at 5 minutes and then every 30 minutes for 1400 minutes. Media used in all samples is MRS. Peptide is promoter activation peptide SppIP. Each group consists of eight samples.

In vitro expression of plasmid pLAB112_Luc in *Lactobacillus reuteri* R2LC re-inoculated and grown for 2 hours from overnight culture remained high for more than 600 minutes (10 h.). There was no leakage/expression from plasmids not activated with activation peptide SppIP (FIG. 2).

Figure 3:
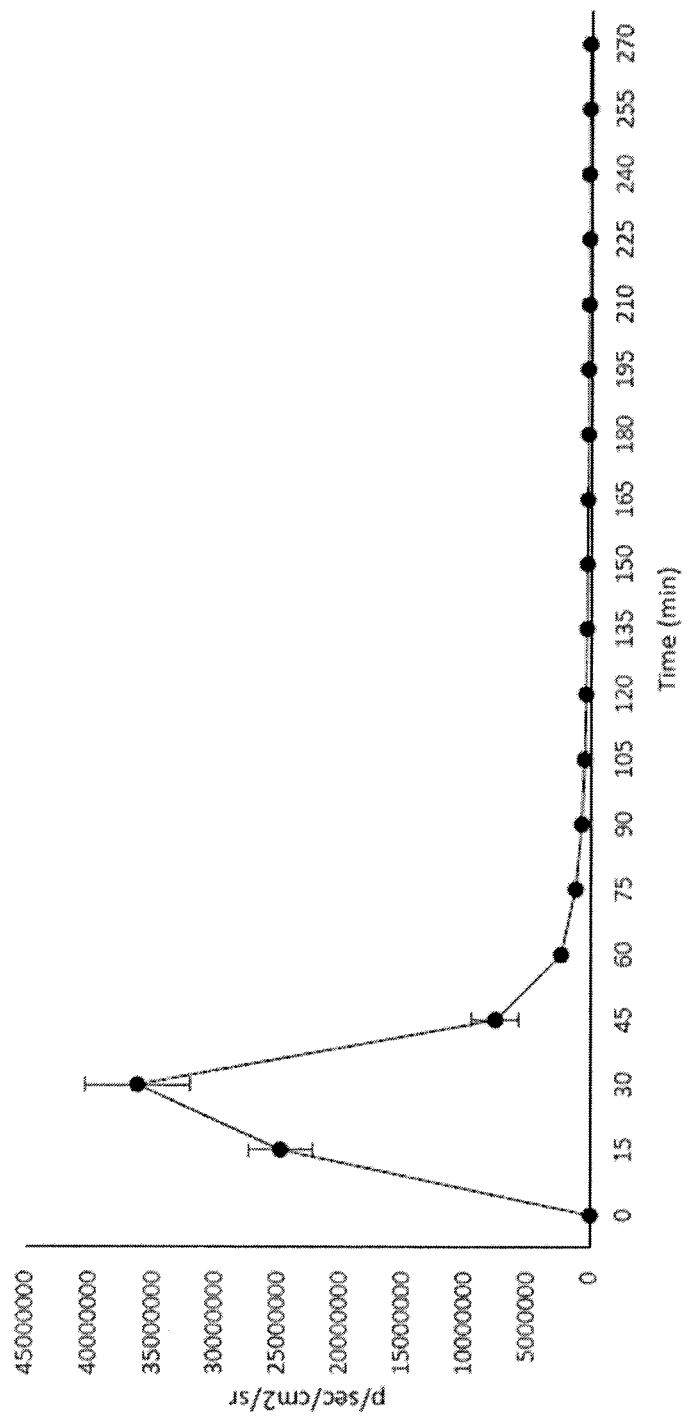
FIG. 3. Expression of pLAB112_Luc in *Lactobacillus reuteri* R2LC re-inoculated from overnight culture to start OD 0.5 applied on 1 day old cutaneous full thickness wounds. In vivo expression measured by non-invasive bioimaging over time. A baseline image at time 0 was acquired on 5 anesthetized mice with 1 day old cutaneous full thickness wounds. Then 25 µl *Lactobacillus reuteri* R2LC_pLAB112_Luc activated with promoter activation peptide SppIP (50 ng/ml) and substrate D-Luciferin (150 µg/ml) was added to the middle of the wounds and mice were imaged at 5 minutes and then every 15 minutes for 270 minutes.

When *Lactobacillus reuteri* R2LC with pLAB112_Luc re-inoculated and grown for 2 hours from overnight culture were placed in 1 day old cutaneous full thickness wounds of anesthetized mice, bacteria was restricted to the wound site and plasmid expression was high for the first hour but signal was detected for more than 4 hours (FIG. 3).

Example 3: Improved Wound Healing in Healthy Mice

Figure 4A:
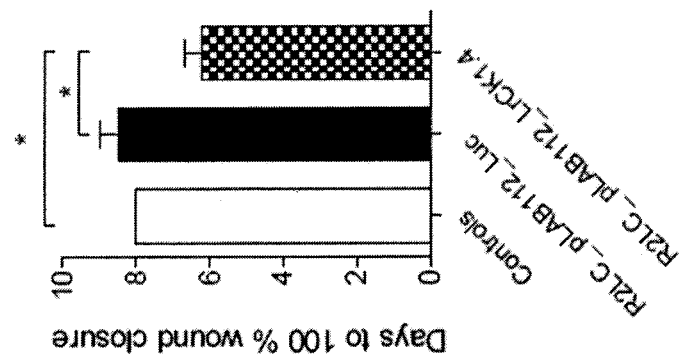
FIGS. 4A, 4B & 4C. Time to wound healing in healthy mice. Time to 50% (FIG. 4A), 75% (FIG. 4B) or complete (100%) (FIG. 4C) healed wound surface, n=5 all groups.
Figure 4B:
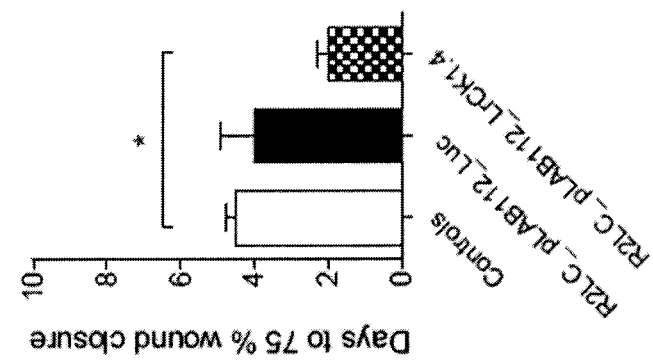
Figure 4C:
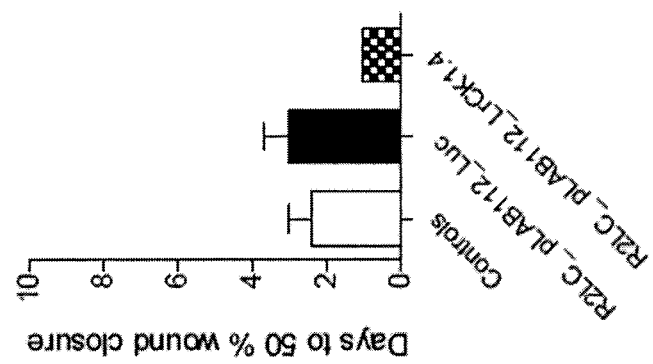
Figure 5B:
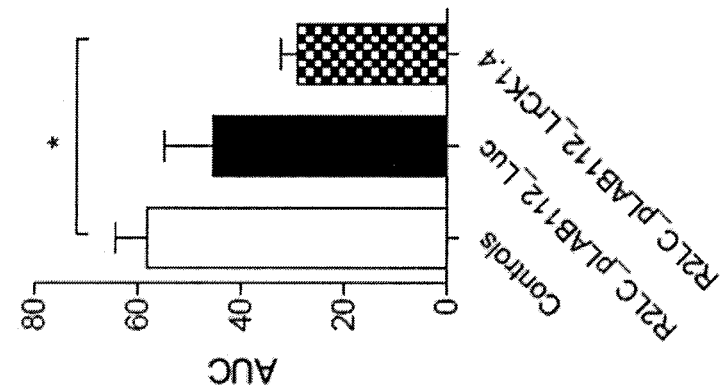
FIGS. 5A & 5B. Wound size (FIG. 5A) and wound exposure (FIG. 5B) over time in healthy mice. Wound size measured daily from images with a scale included, n=5 all groups.
Figure 5A:
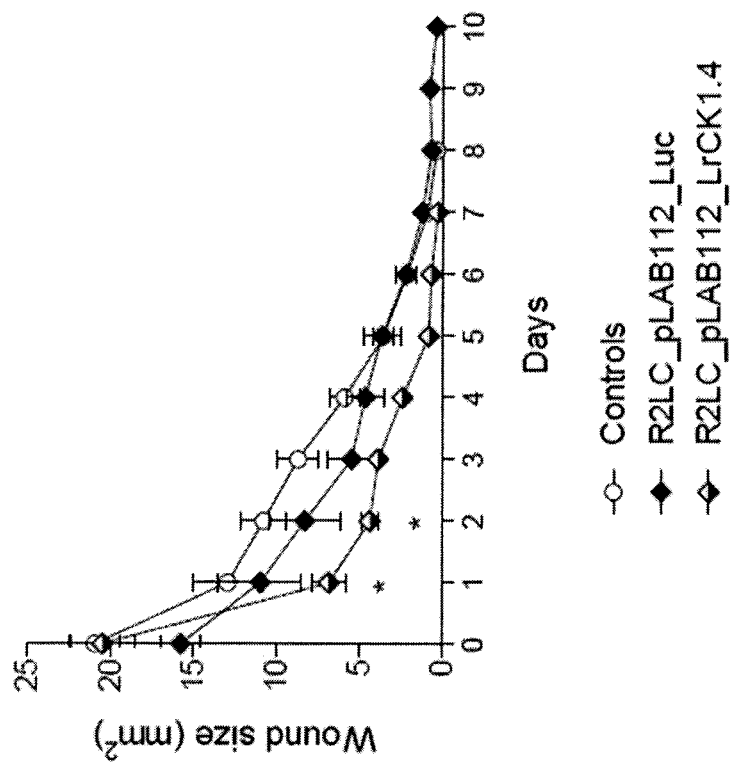
Figure 35A:
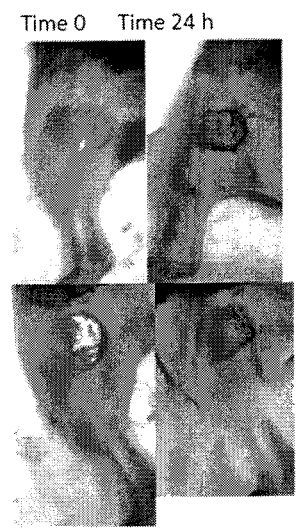
FIGS. 35A, 35B & 35C. Representative images of full thickness skin wounds (5 mm diameter) induced in healthy mice at time 0 and after 24 hours with no treatment, with R2LC Luc or R2LC LrCK1. Images are taken with a scale included in anesthetized mice.
Figure 35B:
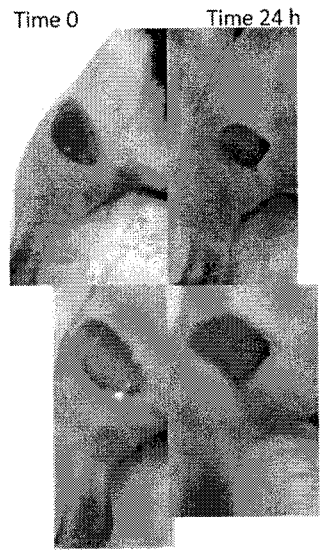
Figure 35C:
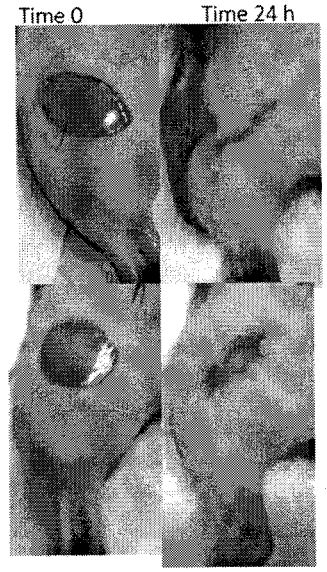

Wounds were monitored daily during the healing process. In healthy mice daily single application of *Lactobacillus reuteri* R2LC_pLAB112_mLrCK1.4 reduced time to both 75% wound surface closure and to complete (100%) wound closure compared to control mice where nothing was applied to the wound and to mice where control *Lactobacillus reuteri* R2LC (pLAB112_Luc) was applied daily (FIGS. 4A, 4B & 4C). The effect of *Lactobacillus reuteri* R2LC_pLAB112_mLrCK1.4 on wound healing was most prominent during the first days post wound induction. Wound size was then further reduced by daily application (one and two days post wound induction) of *Lactobacillus reuteri* R2LC_pLAB112_mLrCK1.4 when compared to control mice where nothing was applied to the wound. The total wound exposure measured as area under curve was also reduced in this group compared to control mice where nothing was applied to the wound (FIGS. 5A & 5B). FIGS. 35A, 35B & 35C show representative images of full thickness skin wounds (5 mm diameter) induced in healthy mice at time 0 and after 24 hours with no treatment, with R2LC Luc or R2LC LrCK1.

Figure 6A:
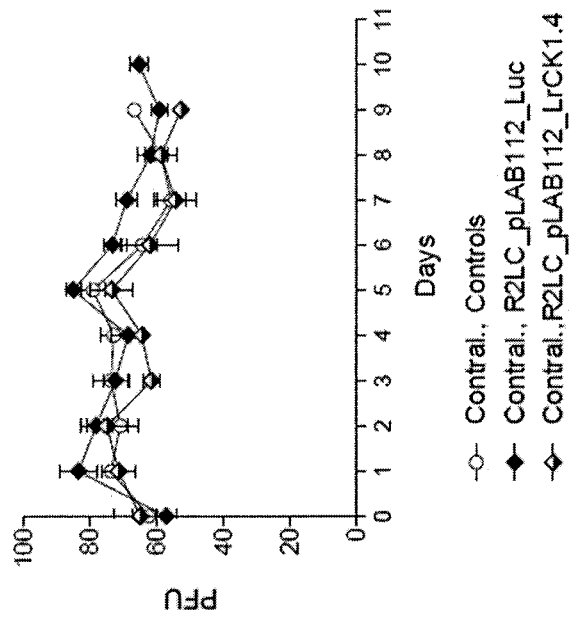
FIGS. 6A & 6B. Ischemia induction by femoral artery ligation prior to wound induction, n=4 in all groups. Cutaneous blood flow measured in ischemic limb (FIG. 6A) and the contralateral corresponding unaffected limb (FIG. 6B) of anesthetized mice over time using Laser Speckle Contrast Analysis. Data is expressed in perfusion unites (PFU). A and B, Two-way ANOVA, Bonferroni compare all columns, d0-d7 analyzed. No change is observed due to time or treatment.
Figure 6B:
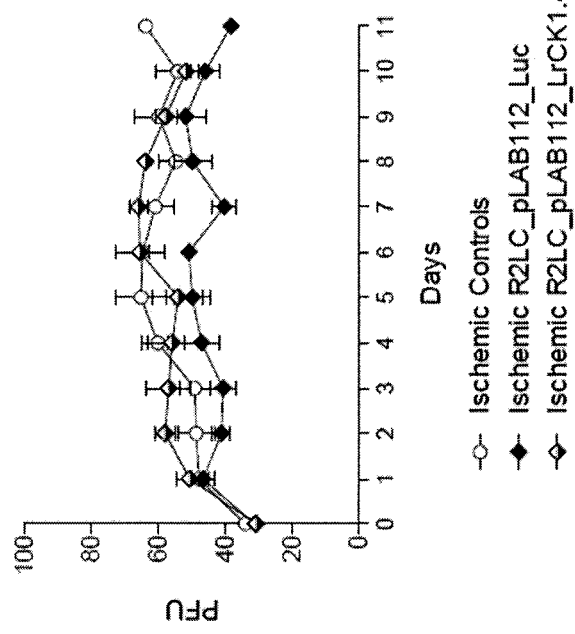
Figure 7A:
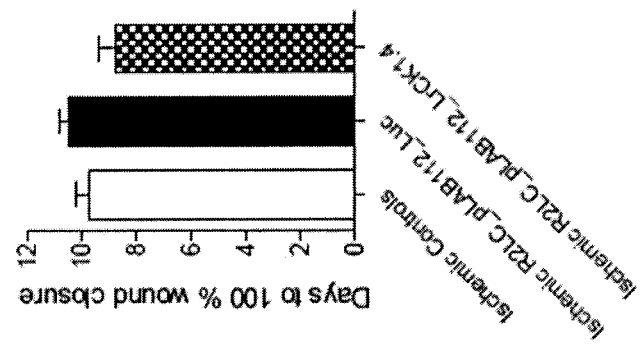
FIGS. 7A, 7B & 7C. Time to wound healing in mice with ischemia at the time of wound induction. Time to 50% (FIG. 7A), 75% (FIG. 7B) or complete (100%) (FIG. 7C) healed wound surface, n=4 all groups.
Figure 7B:
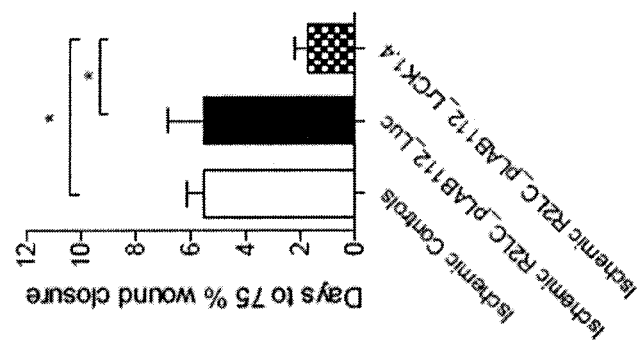
Figure 7C:
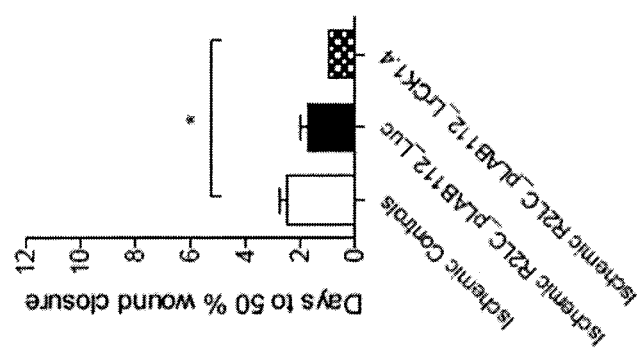
Figure 8B:
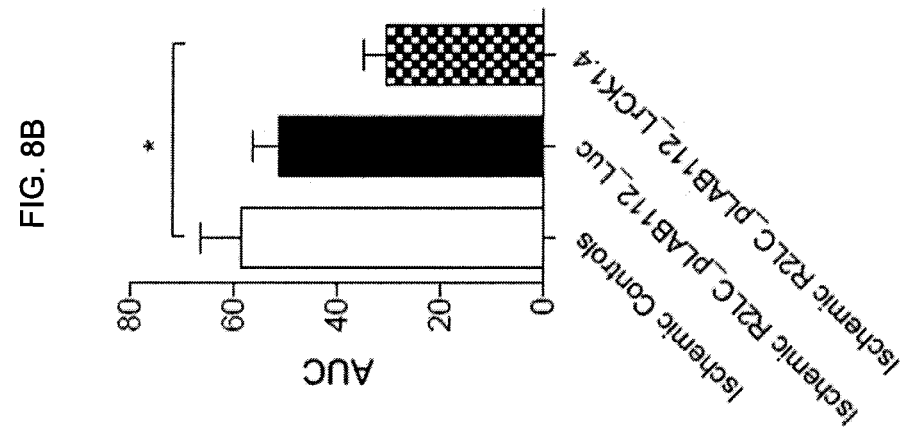
FIGS. 8A & 8B. Wound size and wound exposure over time in mice with local ischemia at the time and location of wound induction. Wound size measured daily from images with a scale included, n=4 all groups.
Figure 8A:
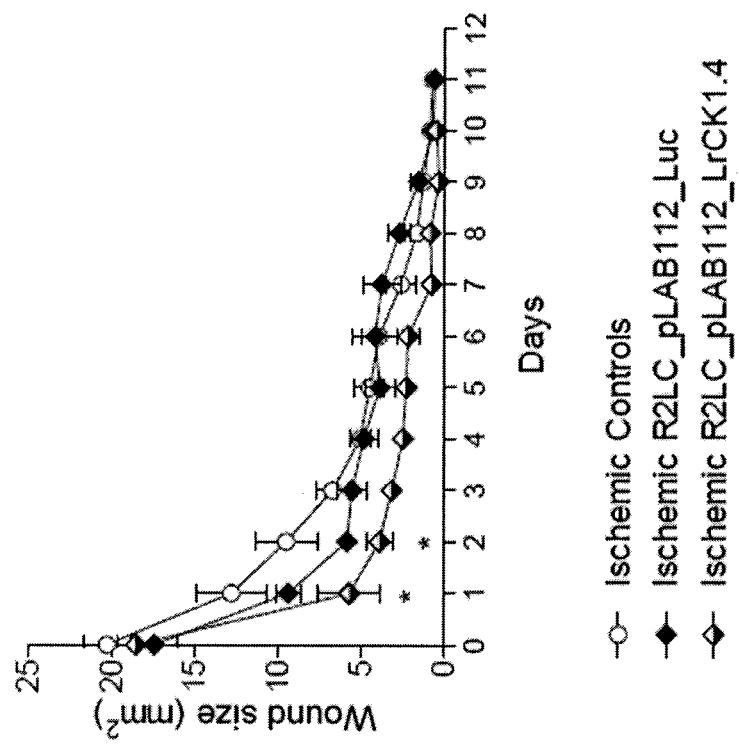

Example 4: Improved Wound Healing in Healthy Mice Having Impaired Tissue Perfusion Cutaneous perfusion was reduced by 50% at the day of wound induction by ligation of the femoral artery in the limb where the wound was induced (FIGS. 6A & 6B and Table III). In mice with ischemia, daily single application of *Lactobacillus reuteri* R2LC_pLAB112_mLrCK1.4 resulted in reduced time to both 50% and 75% wound surface closure compared to control mice where nothing was applied to the wound as well as to mice where control *Lactobacillus reuteri* R2LC (pLAB112_Luc) was applied daily (FIGS. 7A, 7B & 7C). Also in mice with reduced cutaneous perfusion the effect of *Lactobacillus reuteri* R2LC_pLAB112_mLrCK1.4 on wound healing was most prominent during the first days post wound induction, and wound size were reduced by daily application of *Lactobacillus reuteri* R2LC_pLAB112_mLrCK1.4 at one and two days post wound induction compared to control mice where nothing was applied to the wound. The total wound exposure was also reduced in this group compared to control mice where nothing was applied to the wound (FIGS. 8A & 8B).

TABLE III

Basal skin perfusion measured by Laser Speckle Contrast Analysis in anesthetized mice. Data is expressed as Mean ± SEM in perfusion units (PFU), n = 4 all groups.

|  | Healthy | Ischemic | Reduction (%) |
|---|---|---|---|
| Control | 62.5 ± 4.3 | 34.0 ± 1.8 | 46 |
| R2LC_pLAB112_Luc | 57.3 ± 2.7 | 31.3 ± 1.1 | 46 |
| R2LC_pLAB112_LrCK1.4 | 65.0 ± 7.2 | 30.8 ± 0.4 | 52 |

Example 5: Improved Wound Healing in Hyperglycemic Mice

Figures 9A, 9B:
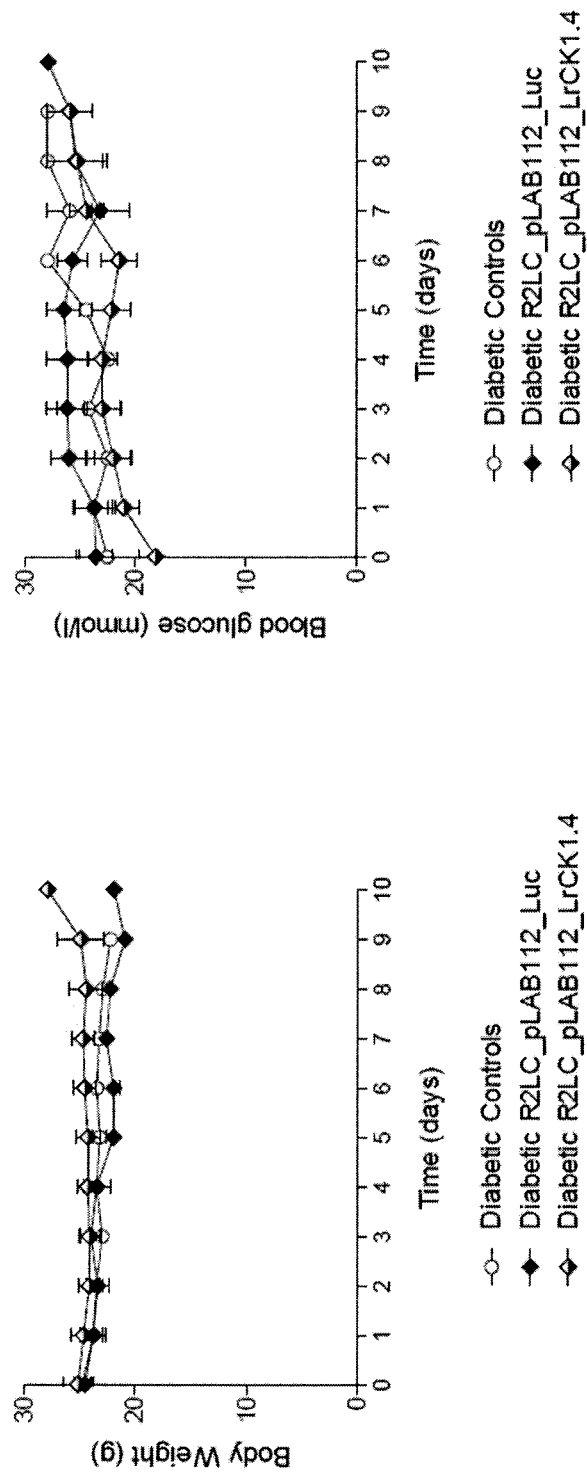
FIGS. 9A & 9B. Body weight (FIG. 9A) and blood glucose (FIG. 9B) following induction of diabetes using a single i.v. injection of alloxan monohydrate. Diabetic Controls, n=4, Diabetic R2LC_pLAB112_Luc, n=5, Diabetic R2LC_pLAB_LrCK1.4, n=4.
Figure 10A:
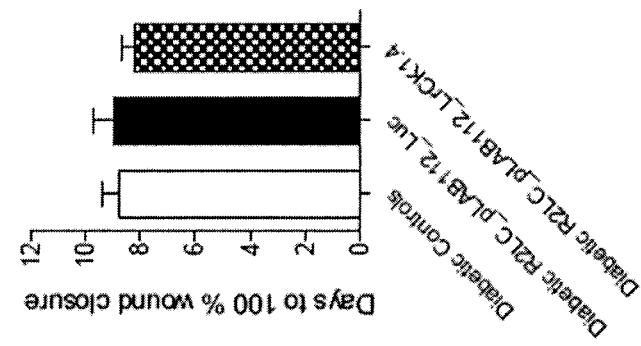
FIGS. 10A, 10B & 10C. Time to wound healing in mice with diabetes at wound induction. Time to 50% (FIG. 10A), 75% (FIG. 10B) or complete (100%) (FIG. 10C) healed wound surface, Diabetic Controls, n=4, Diabetic R2LC_pLAB112_Luc, n=5, Diabetic R2LC_pLAB_LrCK1.4, n=4.
Figure 10B:
Figure 10C:
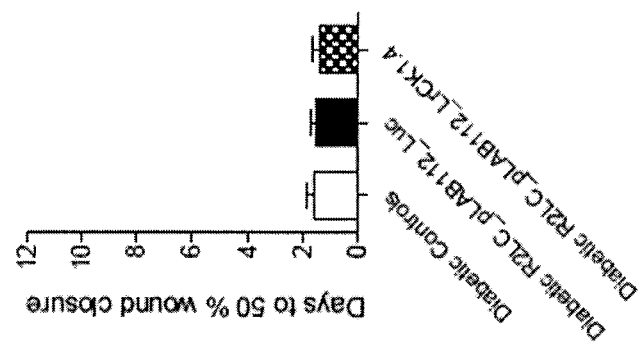
Figure 11B:
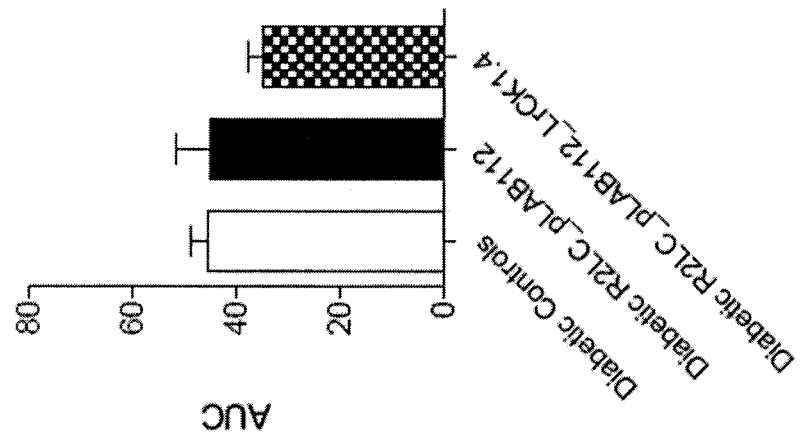
FIGS. 11A & 11B. Wound size and wound exposure over time in mice with diabetes at wound induction. Wound size measured daily from images with a scale included, Diabetic Controls, n=4, Diabetic R2LC_pLAB112_Luc, n=5, Diabetic R2LC_pLAB_LrCK1.4, n=4.
Figure 11A:
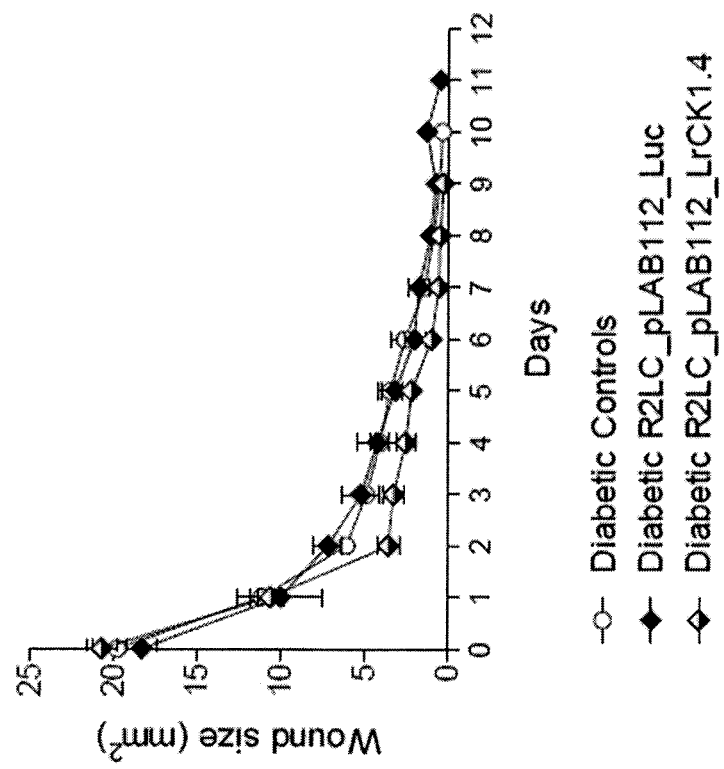
Figure 12:
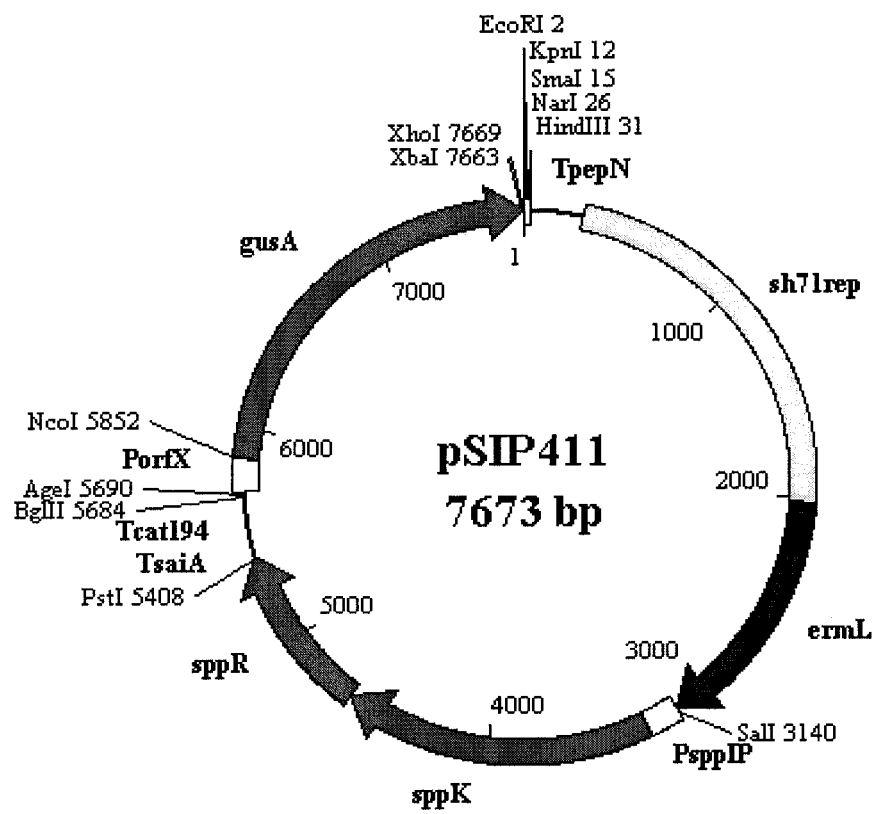
FIG. 12. The pSIP411 plasmid.

Mice were rendered diabetic using alloxan, where after they remained hyperglycemic (>16.7 mmol/l) during the process of wound healing and did not lose weight (FIGS. 9A & 9B). In mice with diabetes, daily single application of *Lactobacillus reuteri* R2LC_pLAB112_LrCK1.4 reduced time to 75% wound surface closure compared to control mice where nothing was applied to the wound and to mice where control *Lactobacillus reuteri* R2LC (pLAB112_Luc) was applied daily (FIGS. 10A, 10B & 10C). There was a trend (p=0.08) towards reduced wound exposure in diabetic mice by daily application of *Lactobacillus reuteri* R2LC_pLAB112_mLrCK1.4 compared to daily application of *Lactobacillus reuteri* R2LC with Luc and control mice where nothing was applied to the wound (FIGS. 11A & 11B).

Example 6: CXCL12 Dermal Overexpression in the Wound Edge Dermis Transfection with Plasmid Encoding CXCL12

Plasmids were constructed on the pVAX1 backbone with CMV promoter (SEQ ID NO: 24) (V260-20, Invitrogen, Waltham, Mass., USA), and either insert -copGFP-T2A-Luc2- referred to as pCTR (SEQ ID NO: 25) or -CXCL12-P2A-copGFP-T2A-Luc2- referred to as pCXCL12 (SEQ ID NO:26) was introduced as previously described (Ref. 18). The secretion sequence for CXCL12 was substituted for the murine IgG secretory sequence. Thus, pCTR plasmids encode GFP (Green Fluorescent Protein) and luciferase but no chemokines. Plasmids (40 μg in a total volume of 100 μl saline) were injected in the dermis in four locations in the wound edge. Transgene expression was measured over time based on luciferase activity following intraperitoneal injection of D-Luciferin (150 mg/kg, #122796, Perkin Elmer, Waltham, Mass., USA) 10 min prior to anesthesia and image acquisition using a bioimaging device (IVIS Spectrum, Perkin Elmer). Data was quantified using Living Image 3.1 software (Perkin Elmer) and imaging parameters were maintained for comparative analysis. Settings were also maintained selecting region of interest where the contralateral reference area was subtracted. Radiance was considered proportional to plasmid expression.

Figure 13:
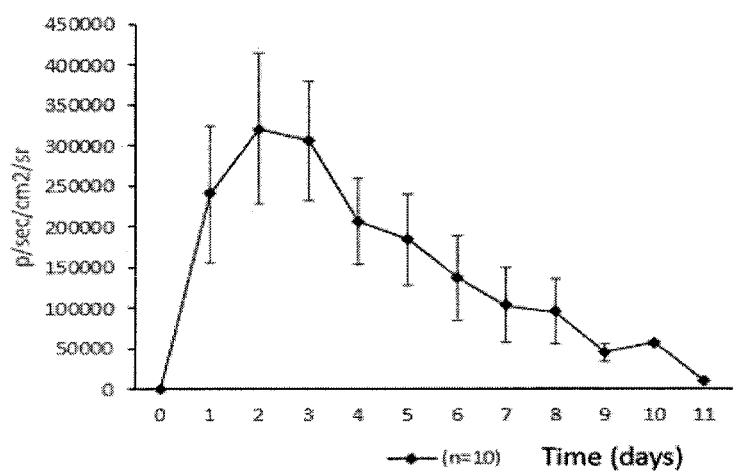
FIG. 13. Quantification of plasmid expression in dermis in wound edge (40 μg DNA) using detection of luminescent signal by non-invasive bioimaging (IVIS Spectrum) over 11 days (n=10).
Figure 14A:
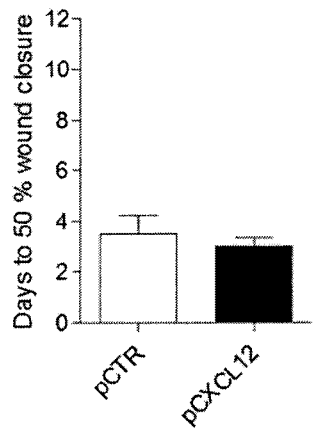
FIGS. 14A, 14B & 14C. Time to wound healing in healthy mice. Time to 50% (FIG. 14A), 75% (FIG. 14B) or complete (100%) (FIG. 14C) healed wound surface (n=8 pCTR, n=9 pCXCL12).
Figure 14B:
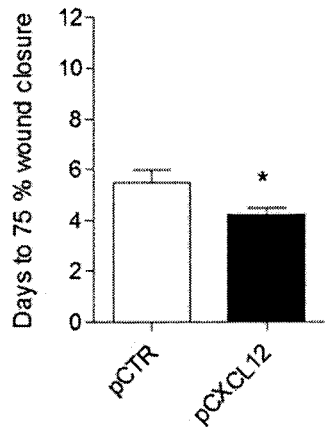
Figure 14C:
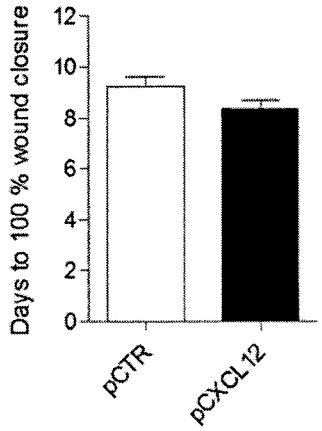
Figure 15A:
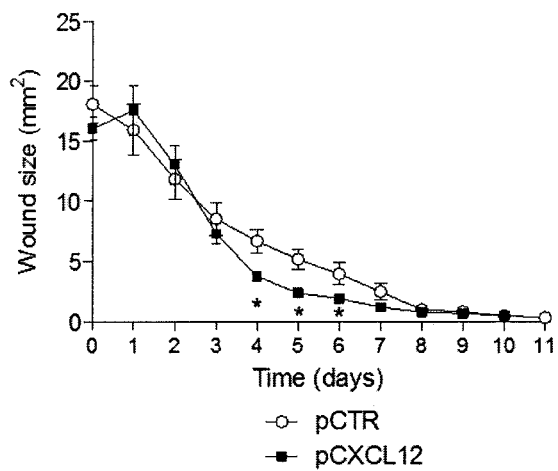
FIGS. 15A & 15B. Wound size (FIG. 15A) and wound exposure (FIG. 15B) over time in healthy mice. Wound size measured daily from images with a scale included (n=8 pCTR, n=9 pCXCL12).
Figure 15B:
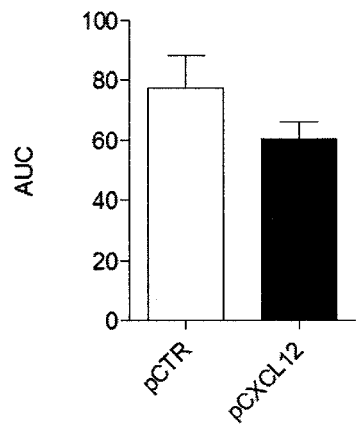

Plasmid expression from the dermis in the wound edge was measured using non-invasive bioimaging and correlated to light produced by the luciferase enzyme encoded by the plasmids equivalent to the expression of CXCL12. Expression peaked on day 2 and then declined as the wound was closing and the dermis reconstituted (FIG. 13). Overexpression of CXCL12 did not result in accelerated complete wound healing but lead to shorter time to closure of 75% of the wound surface as compared to pCTR (FIGS. 14A, 14B & 14C). Wound surface was decreased by pCXCL12 dermal expression as compared to pCTR day 4-6 post wound induction and dermis transfection (FIGS. 15A & 15B). These results demonstrate that with CXCL12 delivered to the wound with this system there is not a dramatic effect the 24 first hours but rather a smaller effect at the later time points.

Example 7: Dose-Response *Lactobacillus reuteri* of Topical Treatment with Luc and LrCK1

*Lactobacillus* was reinoculated from overnight culture and grown to OD 0.5 and then diluted or concentrated to OD 0.2, 0.5, 1.0 and 1.25 in MRS. The four different concentrations were diluted tenfold to $10^{-9}$ and 10 µl of every sample was plated on MRS agar with erythromycin and cultured in an anaerobic chamber overnight in at 37° C., 5% carbon dioxide overnight. Colonies on the plates were counted and concentration expressed as colony forming units per ml (CFU/ml).

For dosing experiments wounds were treated daily for two days with either 25 µl saline or *Lactobacillus reuteri* R2LC pLAB112_LrCK1.4 re-inoculated from overnight culture and grown to OD 0.5, preactivated 5 min prior to application with activation peptide SppIP (50 ng/ml) and added topically to the middle of the wound surface at concentrations of OD 0.2, 0.5, 1.0 or 1.25. In 25 µl OD of 0.5 there are $5 \times 10^7$ bacteria ($2 \times 10^9$ cfu/ml) meaning a dose span of 1000 times.

Bacterial concentration was measured by optical density and colony forming units per ml are displayed in FIG. 16. The lowest dose (OD 0.2 equals $2 \times 10^7$ bacteria) of R2LC_pLAB112_LrCK1.4 cultured and activated as before administered to the wound resulted in the smallest wound size after 24 hours and all four different concentrations resulted in significantly accelerated wound closure at 24 and 48 hours post wound induction (FIG. 17A) and thus resulted in decreased wound exposure to the first 48 hours as compare to wounds receiving no treatment (FIG. 17B). These results indicate that administration of a dose that is $10^3$ higher (OD 1.25 equals $1 \times 10^{10}$ bacteria) than the lowest dose giving the greatest effect also significantly accelerates wound healing the first 48 hours as compared to wounds receiving no treatment and to the same extent as the dose giving maximal wound closure. No signs of induced inflammation or other negative side effects were observed for wounds given the highest dose. The data show that even a low dose of *Lactobacillus reuteri* R2LC_LrCK1 accelerates wound healing.

Example 8: Dose Escalation of mCXCL12 1α Protein as a Topical Treatment

To investigate the effects of the dose of the mCXCL12 1α administered to the wound surface 0.2 µg, 0.6 µg or 1 µg mCXCL12 1α (RnD Systems) was delivered to the wounds daily for two days in 10 µl saline. The administration was once per day.

Figure 18A:
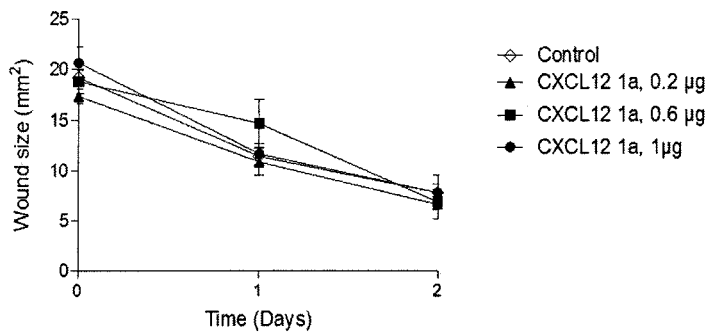
FIGS. 18A & 18B. Wound size (FIG. 18A) and wound exposure (FIG. 18B) over time in healthy mice treated with different concentrations of murine CXCL12 1α at one time point per day for two days. Wound size measured daily from images with a scale included.
Figure 18B:
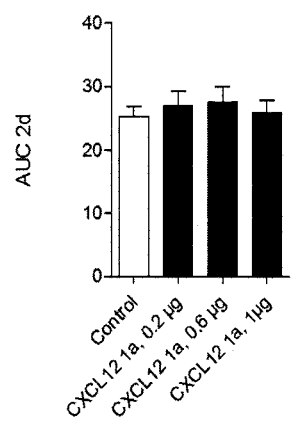
Figure 19A:
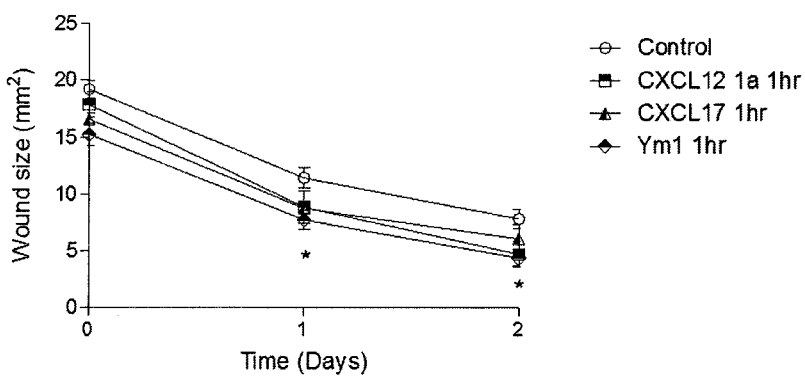
FIGS. 19A & 19B. Wound size (FIG. 19A) and wound exposure (FIG. 19B) over time in healthy mice treated with 0.2 μg recombinant protein every $10^{th}$ minute for one hour every day. Wound size measured daily from images with a scale included.
Figure 19B:
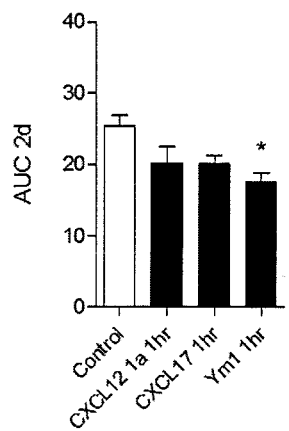

Delivery of the mCXCL12 1α daily at one single time point per day did not accelerate wound healing for the first two days as compared to no treatment (FIGS. 18A & 18B). These data shows that it is the continuous delivery of the CXCL12 1α that causes the accelerated wound healing since a total 0.2 µg mCXCL12 1α given every day for one hour in 10 min intervals accelerated healing the first 48 hours (FIGS. 18A, 18B, 19A & 19B).

Example 9: Re-Epithelialization Assay in Human Skin Biopsies

Sterile normal human skin was obtained from healthy white women having routine breast reduction at Uppsala University Hospital giving consent for donation. Samples were covered with physiological DMEM supplemented with 2% bovine calf serum (Hyclone®, HyClone Laboratories, Logan USA) and transported to the laboratory under sterile conditions.

As previously described (Ref. 17), the subcutis was removed and remaining dermis and epidermis was cut using a 6 mm skin biopsy punch (Integra Miltex, York, Pa., USA) and sterile scissors. In the center of each 6 mm diameter skin disc the epidermis was removed using a 3 mm skin biopsy punch and sterile scissors. Samples were then placed one by one in a sterile 24 well plate with the epidermal side up. All culture media (DMEM) was supplemented with BSA, 2 or 10% and antibiotics (erythromycin Sigma Aldrich, Buchs, Swizerland at 10 µg/ml). To maintain the nutrients on the dermal side i.e. nutrients at the highest concentration on the dermal side of the skin, 0.5 ml medium was added to each well and medium was changed daily. At the same time as the change of medium $10^6$ in 10 µl MRS *Lactobacilus reuteri* R2LC_Luc or *Lactobacilus reuteri* R2LC_LrCK1 were placed in the middle of the epidermal wound in the floating skin discs. The bacteria was inoculated and grown in MRS for 2-4 hours to be in the exponential phase. Samples were incubated at 37° C., 5% carbon dioxide, and 95% humidity for 14 days.

The specimens were cut through the middle and one half was fixated overnight in 4% formaldehyde, pH 7.38 and dehydrated through an ethanol-xylene series to finally be embedded in paraffin. Cross-sections (10 µm) starting from the part being at the center of the specimens, were mounted, deparaffinized, rehydrated, and stained with hematoxylin and eosin. Images were captured using Leica Leits Dmrb with a Leica DFC420 C camera and Plan Fluot 40×0.7 NA objective. Re-epitelialization or epidermis sleeve length was measured in images using ImageJ (NIH).

Figure 20A:
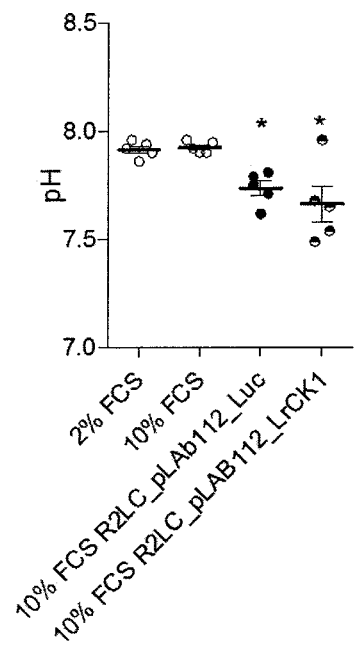
FIGS. 20A & 20B. Re-epithelialization measured in human skin epidermal punch biopsy wounds.
Figure 20B:
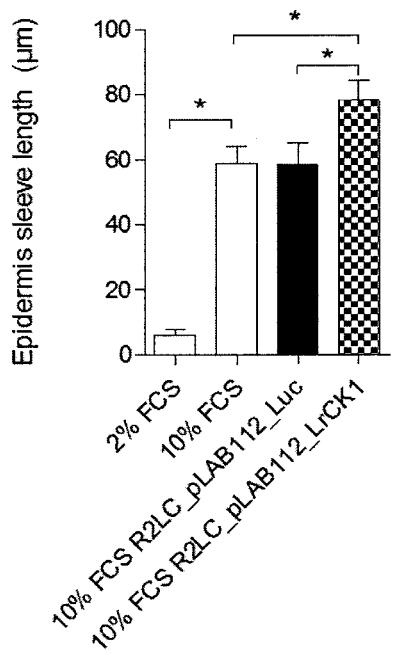

Adding *Lactobacillus* to the skin discs in culture lowered the pH of the culture medium when measured after 24 hours (FIG. 20A). The epidermis on the edges of the induced wound in the skin discs was proliferating to cover the exposed dermis when 10% FCS was present in the culture medium and there was almost no proliferation when skin discs were cultured in medium supplied with 2% FCS after 14 days in culture (FIG. 20B). No detrimental effects were macroscopically detected in the skin discs treated with R2LC pLAB112 Luc or R2LC pLAB112_LrCK1 and increased re-epithelialization was measured on wounds where the skin discs were treated with R2LC pLAB112_LrCK1 for 14 days (FIG. 20B).

Example 10: Functionality of Bacteria after Freeze-Drying and Revival

Different protocols and 35 different formulations for freeze-drying were tested and viability was measured for up to two months. Also a larger batch of freeze-dried *Lactobacillus reuteri* was produced in settings identical to large scale industrialized production and in accordance with good manufacturing practice. The freeze-dried samples from this batch have been analyzed for viability after storing for up to two months in temperatures ranging from −20 to 40° C. Freeze-dried bacteria were revived by adding equivalent volume of water or MRS medium with SppIP (50 ng/ml) and then analyzed immediately for expression in vitro and in vivo by plating them in a 96 well plate or applying them directly on 1 day old wounds as described above.

Figure 21:
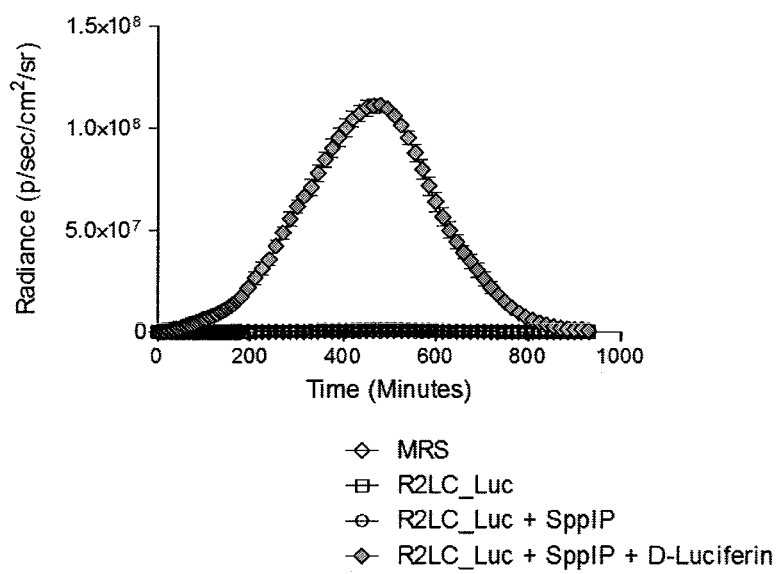
FIG. 21. In vitro expression of pLAB112_Luc in Lactobacillus reuteri R2LC immediately after revival from freeze-dried state measured in vitro by bioimaging over time. A baseline image at time 0 was acquired. Then promoter activation peptide SppIP (50 ng/ml) and substrate D-Luciferin (150 μg/ml) was added immediately after. The plate was imaged at 5 minutes and then every 5-15 minutes for 930 minutes. Media used in all samples is MRS. Peptide is promoter activation peptide SppIP. Each group consists of four samples.
Figure 22:
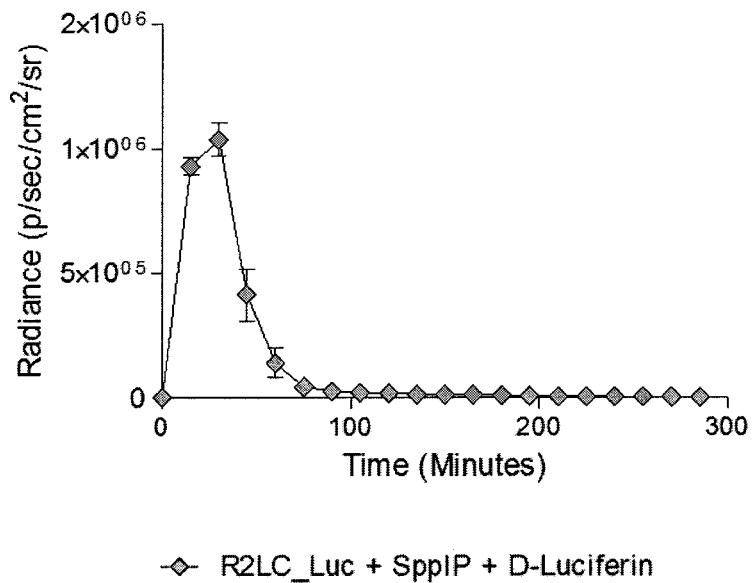
FIG. 22. In vivo expression of pLAB112_Luc in Lactobacillus reuteri R2LC immediately after revival from freeze-dried state and application on 1 day old cutaneous full thickness wounds measured in vivo by bioimaging over time. A baseline image at time 0 was acquired on three anesthetized mice with two separate 1 day old cutaneous full thickness wounds. Then 25 μl Lactobacillus reuteri R2LC_pLAB112_Luc activated with promoter activation peptide SppIP (50 ng/ml) and substrate D-Luciferin (150 μg/ml) was added to the middle of the wounds and mice were imaged at 5 minutes and then every 15 minutes for 270 minutes.

With the most promising formulation, viability was stable from directly after freeze-drying to analysis at two months measured on samples stored at +4° C. The viability was well within range of what is acceptable of freeze-dried bacteria currently being sold as dietary supplements. Measuring the plasmid expression in freeze-dried *Lactobacillus reuteri* R2LC_pLAB112_Luc directly after resuscitation showed immediate induction of expression, which peaked at 450 minutes and then declined (FIG. 21). After 24 hours (1440 minutes) there was no expression and no alive bacteria. When freeze-dried *Lactobacillus reuteri* R2LC_pLAB112_Luc were revived, induced with 50 ng/ml (SppIP) and immediately placed on cutaneous wounds of mice ($5 \times 10^7$ per 25 µl), expression directly increased and was high for about one hour (FIG. 22) in a similar pattern as was seen when adding fresh bacteria in growth phase in solution (FIG. 3).

Figure 23A:
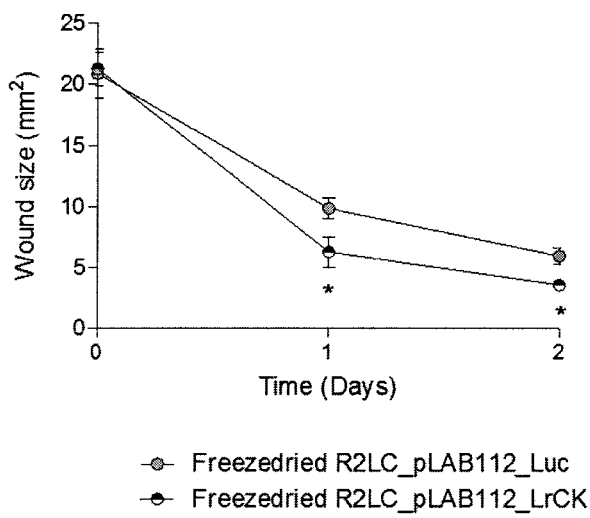
FIGS. 23A & 23B. Wound size (FIG. 23A) and wound exposure (FIG. 23B) over time in healthy mice treated with freeze-dried, revived and induced Lactobacillus reuteri R2LC_pLAB112_LrCK1.4. Wound size measured daily from images with a scale included.
Figure 23B:
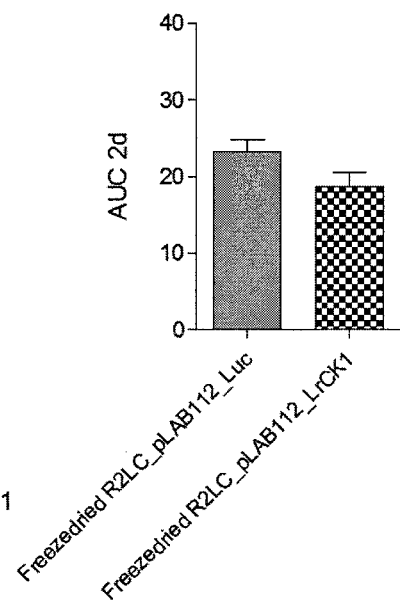

The effect on wound healing was tested where the freeze-dried bacteria ($5 \times 10^7$ per 25 µl) was again revived, induced and immediately placed on cutaneous wounds of mice. The wounds were monitored every day for two days and the wounds treated with *Lactobacillus reuteri* R2LC_pLAB112_LrCK1 showed accelerated healing compared to wounds treated with *Lactobacillus reuteri* R2LC_pLAB112_Luc (FIGS. 23A & 23B) even with this protocol. These data show that the *Lactobacillus reuteri* R2LC_pLAB112 does not have to be precultured to the exponential growth phase in order to produce and deliver enough CXCL12 to accelerate wound healing in vivo.

Example 11: pH Dependent Effects of Chemokine Signaling

Chemokines can appear as monomers, dimers or multimers either with itself or interacting with other chemokines (Ref. 22). The different combinations and conformations induce different receptor signaling and thus different cell responses (Ref. 34). This is a new and unexplored area and the combination of possibilities is dependent on the local tissue microenvironment. Also local pH impacts on local macrophage function (Ref. 23).

For studies of pH dependent effects of chemokine potency, 0.2 µg CXCL12 1α was applied to wounds in 10 µl saline with pH 7.35, 6.35 or 5.35 daily for two days.

Figure 24A:
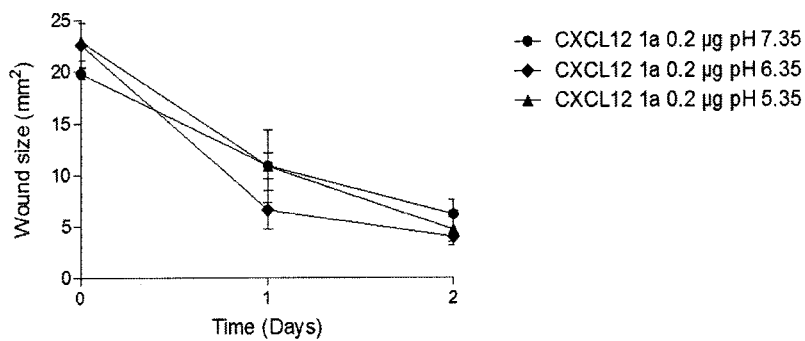
FIGS. 24A & 24B. Wound size (FIG. 24A) and wound exposure (FIG. 24B) over time in healthy mice. Wound size was measured daily from images with a scale included. The change is due to time and treatment and there is a trend towards decreased wound size by CXCL12 1α in pH of 6.35 compared to suspension with pH 7.35 (p=0.07) (pH 7.35; n=8, pH 6.35; n=5, pH 5.35; n=4). One-way ANOVA, Bonferroni compare all columns.
Figure 24B:
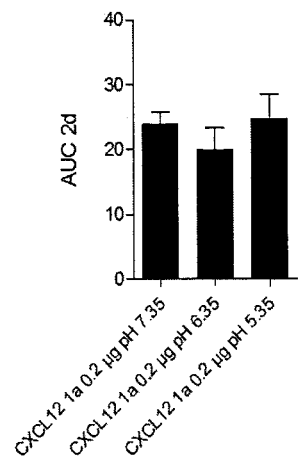

Altering the pH in the buffer containing the chemokines had an effect on the healing pattern of the treated wounds and there was a trend towards smaller wound size one day post wound induction when the CXCL12 were suspended in saline with pH of 6.35 compared to when the CXCL12 were suspended in saline with pH of 7.35 (p=0.07) (FIGS. 24A & 24B). These data indicate that a pH of 6.35 potentiates the effect of recombinant CXCL12 applied to the wound surface in the aspect of inducing accelerated wound healing.

Example 12: Importance of Bacterial on Site Chemokine Delivery to the Wound Surface for Effect For wound treatment with fresh supernatants *Lactobacillus reuteri* R2LC_pLAB112_Luc and R2LC_pLAB112_LrCK1 were inoculated in 10 ml MRS in 37° C. and grown to OD 0.5, centrifuged (>2000 rpm, 5 minutes), resuspended in 1 ml MRS, activated (SppIP, 50 ng/ml) and grown for 4 hours. Samples were then centrifuged (>2000 rpm, 5 minutes) and the supernatant was saved. 25 µl of this supernatant was then applied to wounds once daily for two days.

Figure 25A:
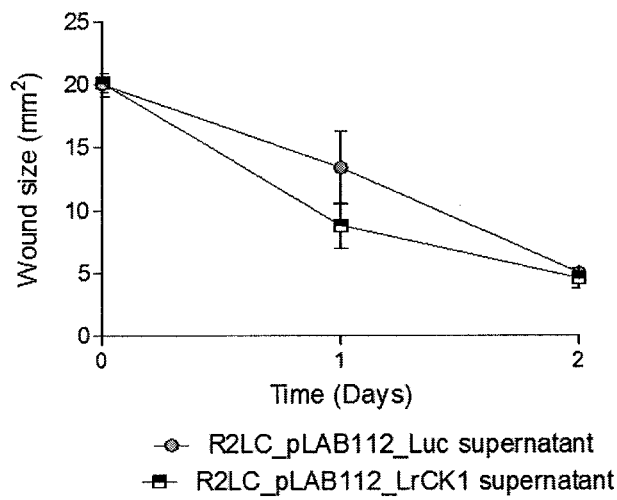
FIGS. 25A & 25B. Wound size (FIG. 25A) and wound exposure (FIG. 25B) over time in healthy mice. Wound size measured daily from images with a scale included. The observed change was only due to time and did not differ between the two different bacterial suspensions (R2LC_pLAB112_Luc; n=4, R2LC_pLAB112_LrCK1; n=5). Student's two-tailed unpaired t-test.
Figure 25B:
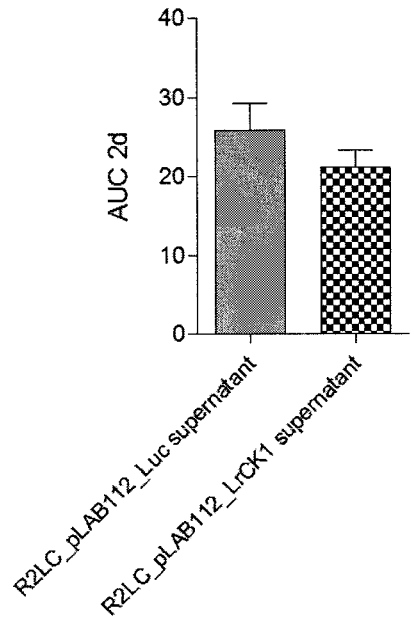

The importance of bacterial delivery of CXCL12 1α directly to the wound surface by the *Lactobacillus reuteri* R2LC_pLAB112_LrCK1 was demonstrated in a model where fresh supernatants from induced *Lactobacillus reuteri* were added to the wounds following wound induction every day for two days. There was no difference in wound size or total wound exposure (p=0.2595) of treatment with fresh supernatants from *Lactobacillus reuteri* R2LC_pLAB112_Luc or R2LC_pLAB112_LrCK1 (FIGS. 25A & 25B).

Example 13: *Lactobacillus* Delivered CXCL12 Increases Levels of CXCL12 in the Skin Surrounding the Wound For quantitative analysis the skin surrounding the wound (0-100 µm from the wound) was removed on the last day of experiments and snap frozen in liquid nitrogen and sectioned (10 µm). After fixation in ice cold methanol (10 min) and permeabilization in 0.5% Triton-X (15 min) tissues were incubated with antibodies targeting CXCL12 1α (polyclonal, Abcam) and macrophage antigen F4/80 (clone BM8, eBioscience) washed and incubated with matching secondary antibodies conjugated to Alexa Fluor488 and Nordic Lights 557 (Invitrogen). Tissues were finally washed and mounted (Fluoromount, #0100-10, Southern Biotech, Birmingham, Ala., USA) before imaging using a line-scanning confocal microscope (Zeiss LSM 5 Live, with a piezo motor-controlled WPlanApo 40×/1.0 with 0.5 optical zoom, Zeiss, Oberkochen, Germany). Protein levels and macrophages were quantified in images using ImageJ (NIH) and IMARIS software 8.2 (Bitplane, Zurich, Switzerland). Microscope settings were maintained during acquisition to allow comparison. Values for CXCL12 1α measurements are presented as mean fluorescent intensity (MFI).

Figure 26A:
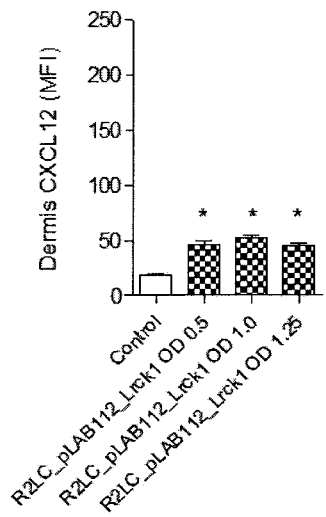
FIGS. 26A, 26B, 26C. Measurements of CXCL12 1α levels sections of the skin just next to the wound two days post wound induction in dermis (FIG. 26A), epidermis (FIG. 26B) and hair follicles (FIG. 26C) where the wounds were treated with *Lactobacillus reuteri* R2LC_pLAB112_LrCK1 at OD 0.5, 1.0, and OD 1.25. One-way ANOVA, Bonferroni compare all columns.
Figure 26B:
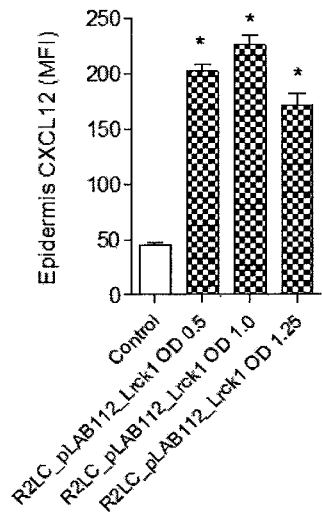
Figure 26C:
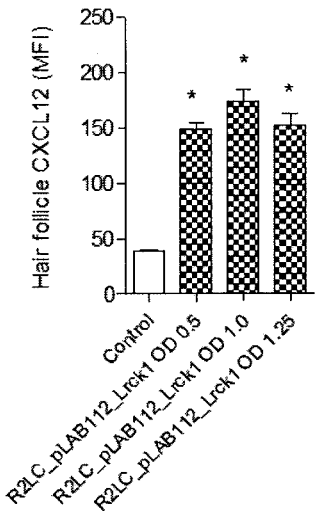

Treatment of wounds once daily for two days with *Lactobacillus reuteri* R2LC_pLAB112_LrCK1 in different doses resulted in increased skin tissue levels of CXCL12 1α in the skin just next to the wound compared to in the skin next to wounds receiving no treatment (FIGS. 26A, 26B & 26C) and this was true for both dermis, epidermis and in hair follicles.

Figure 27A:
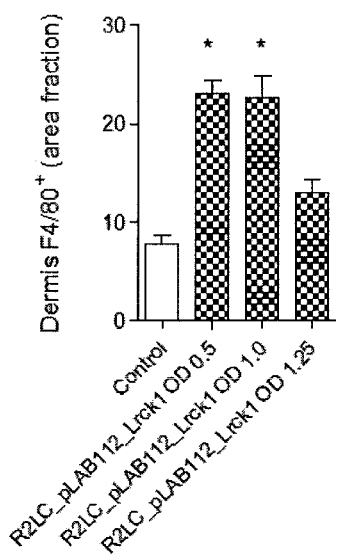
FIGS. 27A & 27B. Measurements of density of F4/80$^+$ macrophages in dermis (FIG. 27A) and epidermis (FIG. 27B) in the skin next to the wound two days following wound induction in control wounds and wounds treated with *Lactobacillus reuteri* R2LC_pLAB112_LrCK1 at OD 0.5, 1.0 and OD 1.25. (Control, n=15; 0.5, n=10, OD 1.0, n=4; OD 1.25, n=5). One-way ANOVA, Bonferroni compare all columns.
Figure 27B:
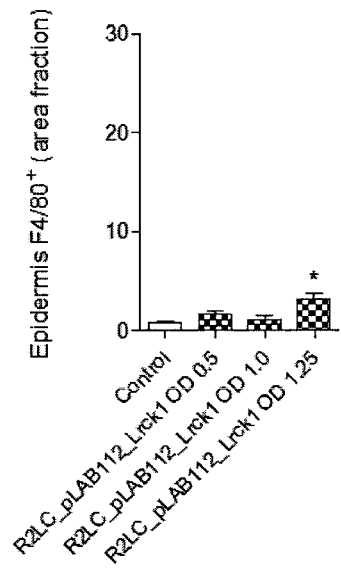

Example 14: *Lactobacillus* Delivered CXCL12 Increases Macrophages in the Skin Surrounding the Wound Treatment of wounds once daily for two days with *Lactobacillus reuteri* R2LC_pLAB112_LrCK1 in different doses resulted in increased density of F4/80+ macrophages in dermis just next to the wound two days post wound induction when *Lactobacillus reuteri* R2LC_pLAB112_LrCK1 at OD 0.2 and OD 0.5 were applied to the wound compared to the dermis next to wounds receiving no treatment (FIG. 27A). F4/80+ macrophages were increased in the epidermis next to the wound two days post wound induction when *Lactobacillus reuteri* R2LC_pLAB112_LrCK1 were given to the wound surface at OD 1.25 as compared to the epidermis next to wounds receiving no treatment (FIG. 27B).

Example 15: Verification of Effect on Acceleration of Wound Healing Using *Lactococcus Lactis*

To show that the local and continuous delivery of the specific chemokine produced by the bacteria is important for the mechanism irrespectively of bacterial strain, another strain was used to produce and deliver the chemokine directly to the wound surface, *Lactococcus Lactis* was transformed with pLAB112 (mLrCK1). Bacteria were applied once daily to full thickness wounds in healthy mice following the same protocol as described for treatment with using *Lactobacuillus reuteri*.

Figure 28A:
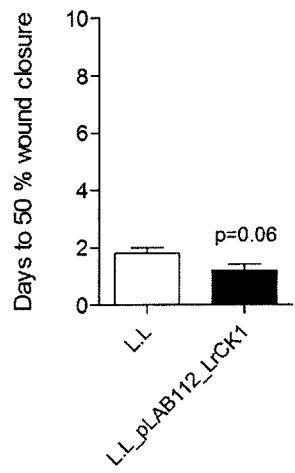
FIGS. 28A, 28B & 28C. Time to wound healing in healthy mice. Wounds were treated with *Lactococcus Lactis* transformed with pLAB112 (L.L_pLAB112_LrCK1) or control *Lactococcus Lactis*. Time to 50% (FIG. 28A), 75% (FIG. 28B) or complete (100%) (FIG. 28C) healed wound surface, n=5 both groups. Student's two-tailed unpaired t-test.
Figure 28B:
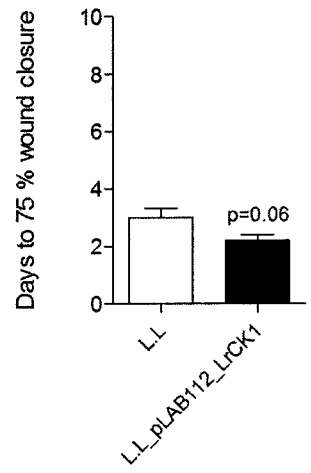
Figure 28C:
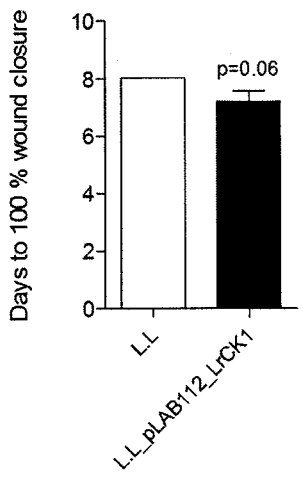
Figure 29A:
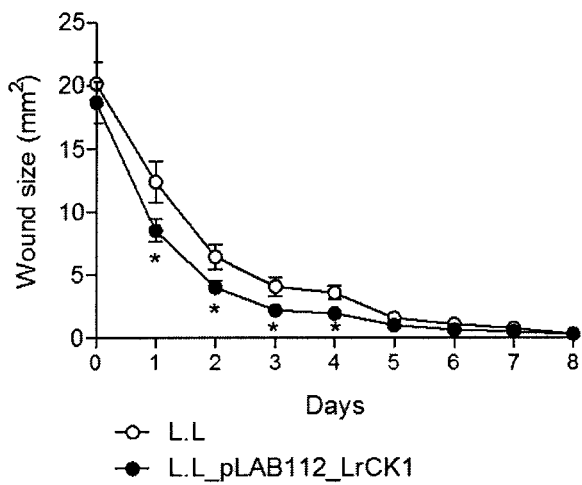
FIGS. 29A & 29B. Wound size (FIG. 29A) and wound exposure (FIG. 29B) over time in healthy mice. Wound size measured daily from images with a scale included, n=5 both groups. The change is due to time and treatment and wound size is decreased by L.L_pLAB112_LrCK1 at d1 to d4 compared to control *Lactococcus Lactis*. Student's two-tailed unpaired t-test.
Figure 29B:
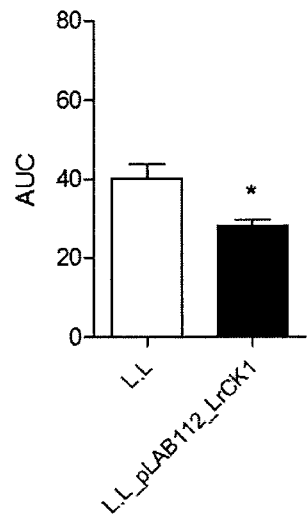
Figure 30A:
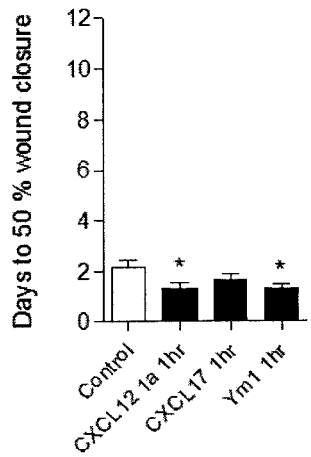
FIGS. 30A, 30B & 30C. Time to wound healing in healthy mice treated with recombinant chemokines for one hour. Time to 50% (FIG. 30A), 75% (FIG. 30B) or complete (100%) (FIG. 30C) healed wound surface (Control; n=11, mCXCL12 1α; n=6, mCXCL17; n=8, mYm1; n=9). One-way ANOVA, Bonferroni compare all columns.
Figure 30B:
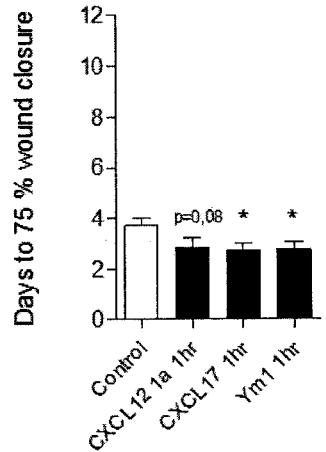
Figure 30C:
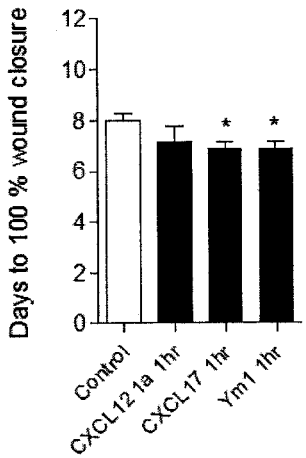
Figure 31A:
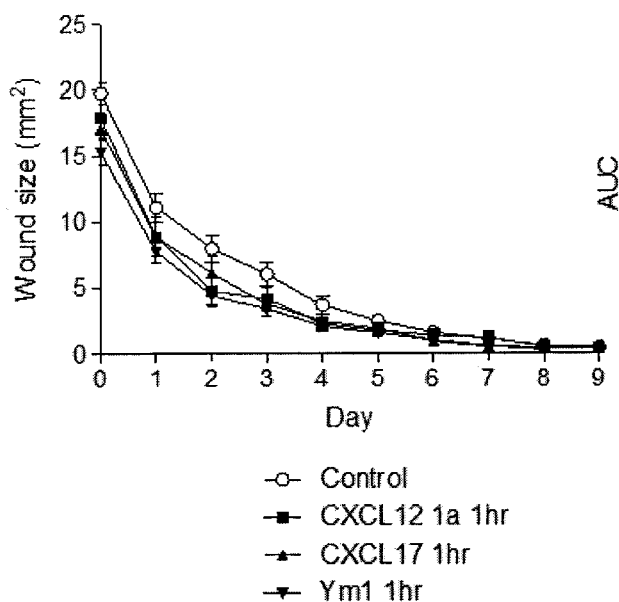
FIGS. 31A & 31B. Wound size (FIG. 31A) and wound exposure (FIG. 31B) over time in healthy mice treated with recombinant chemokines for one hour. Wound size measured daily from images with a scale included (Control; n=11, mCXCL12 1α; n=6, mCXCL17; n=8, mYm1; n=9). The change is due to time and treatment and wound size is decreased by CXCL12 1α, CXCL17 and Ym1 compared to Control. One-way ANOVA, Bonferroni compare all columns.
Figure 31B:
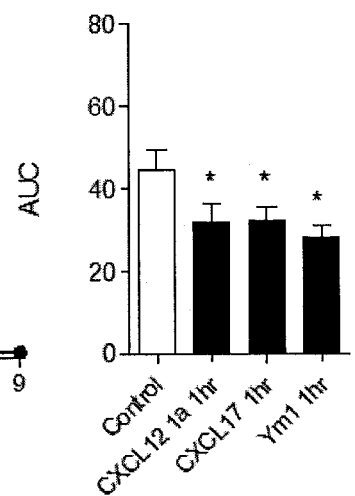

There is a clear trend that mCXCL12 1α delivery accelerates wound closure (FIGS. 28A, 28B & 28C) and reduces wound size and exposure in this model (FIGS. 29A & 29B).

Example 16: Moderate Effects on Time to Wound Closure by Treatment with mCXCL12 1α, mCXCL17 and mYm1 Delivered as Recombinant Proteins To show that the mode of delivery and continuous protein production enabled by the lactic acid bacteria is important for the mechanism, murine recombinant mCXCL12 1α, mCXCL17, mYm1 (total of 200 ng in 60 μl, all RnD Systems) or saline (10 μl) as control was delivered to the wound once daily every 10th minute for one hour.

For mCXCL12 1α, delivery of 30 ng into the peritoneal cavity induces significantly increased recruitment of immune cells in 3 hours, why 200 ng to an area of 25 μm² is to be considered a high dose.

It is likely that the high protease activity in the wound degrades the chemokines when given as recombinant protein at one single time point, and thus the de novo production by the bacteria is required for the protein to enhance wound closure. In addition, the lactic acid bacteria might also provide a beneficial local environment for wound healing (FIGS. 1B, 4A, 4B, 4C, 5A, 5B, 24A, 24B, 30A, 30B, 30C, 31A and 31B).

Figure 32:
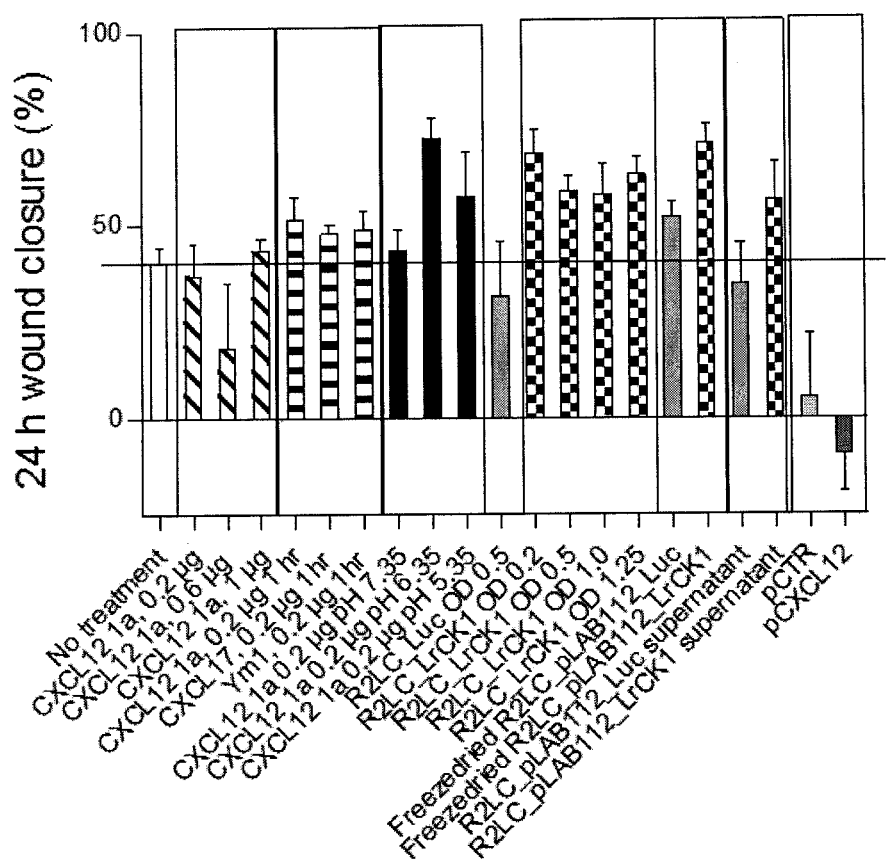
FIG. 32. Wound closure during the 24 first hours in healthy mice with no or different treatments. (No treatment, n=15; 0.2 µg CXCL12 1α, n=4; 0.6 µg CXCL12 1α, n=5; 1.0 µg CXCL12 1α, n=4; 0.2 µg CXCL12 1α 1 hr, n=6; 0.2 µg CXCL17 1 hr, n=9, 0.2 µg Ym1 1 hr, n=9; R2LC_pLAB112_Luc OD 0.5, n=4; R2LC_pLAB112_LrCK1.4 OD 0.2, n=4; R2LC_pLAB112_LrCK1.4 OD 0.5, n=10, R2LC_pLAB112_LrCK1.4 OD 1.0, n=4; R2LC_pLAB112_LrCK1.4 OD 1.25; n=5, Freeze-dried R2LC_pLAB112_Luc, n=4, Freeze-dried R2LC_pLAB112_LrCK1.4, n=5, R2LC_pLAB112_Luc supernatant; n=4, R2LC_pLAB112_LrCK1.4 supernatant, n=5, pCTR n=8; pCXCL12, n=9). No statistical analyses have been performed on this dataset.

Example 17: Comparison of the Effects of Different Treatments on Wound Closure in Healthy Mice Wound closure during the 24 first hours in healthy mice was analyzed for all the different treatments performed (FIG. 32). It is clear that treatment with *Lactobacillus reuteri* R2LC_Luc or low single doses of CXCL12 1α administered to the wound at one time point affects the healing during the 24 first hours. Though there is a trend that CXCL12 1α, CXCL17 and Ym1 delivered to the wound surface every 10$^{th}$ minute for one hour accelerates the wound closure during the first 24 hours and this effect is even more clear when the CXCL12 1α is delivered continuously for one hour to the wound surface by *Lactobacillus reuteri* R2LC_LrCK1. Delivering the CXCL12 via dermal overexpression rather have a detrimental effect on 24 hour wound closure.

Example 18: Acceleration of Wound Healing Also on Mucosal Surfaces by *Lactobacillus reuteri* with pLAB112_mLrCK1.4

To test if the local continuous delivery of CXCL12 to a wounded surface works through a global mechanism on both skin epithelium and intestinal epithelium, two experimental protocols of DSS-induced colitis was used. DSS (dextran sulfate sodium) is known to induce wounds in the mucosal surface of the colon (Ref. 16).

For the first protocol, mice were treated with *Lactobacillus reuteri* by gavage (1 ml OD 0.5 spun and resuspended in 0.1 ml) once daily for 14 days while DSS was given in the drinking water day 7-14. Since this strain of *Lactobacillus reuteri* colonizes in the colon using this protocol the aim is to assess if presence of *Lactobacillus reuteri* pLAB112_mLrCK1 in the colon is beneficial as compared to *Lactobacillus reuteri* pLAB112_Luc when colitis is induced.

The second protocol aimed at treating manifest colitis, and mice were given DSS in the drinking water day 1-8 while receiving *Lactobacillus reuteri* by gavage three times daily at day 5-8.

The severity of colitis was assessed daily on the basis of clinical parameters including weight loss, stool consistency and blood content, and presented as Disease Activity Index (DAI), a scoring method described in detail by Cooper and coworkers (Ref. 16).

Figure 33A:
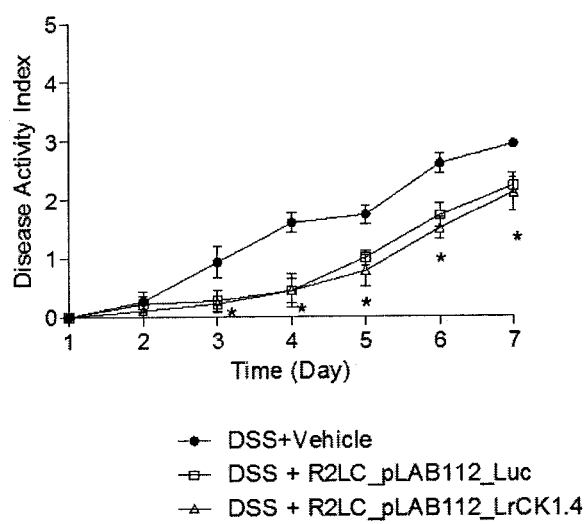
FIGS. 33A & 33B. Assessment of DSS-induced disease activity daily (FIG. 33A) and total disease burden, day 1-7 (FIG. 33B). Similar amelioration of DSS-induced colitis disease activity by treatment with *Lactobacillus reuteri* pLAB112_Luc and pLAB112_LrCK1.4 (DSS+Vehicle; n=5, DSS+R2LC_pLAB112_Luc; n=6, DSS+R2LC_pLAB112_LrCK1.4; n=7) as compared to the control group treated with vehicle, One-way ANOVA, Bonferroni compare all columns.
Figure 33B:
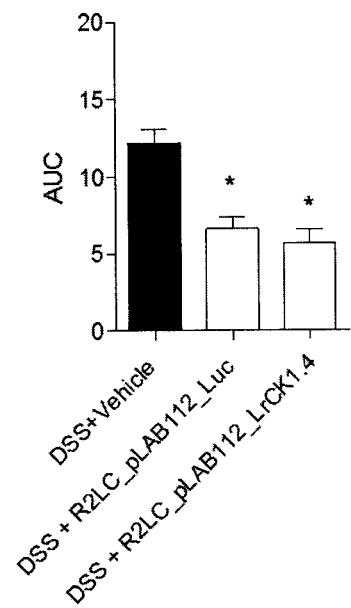

There was similar amelioration of DSS-induced colitis disease activity by pretreatment with *Lactobacillus reuteri* pLAB112_Luc and pLAB112_LrCK1.4 (FIGS. 33A & 33B) indicating the effect is only due to the *Lactobacillus reuteri*.

Figure 34A:
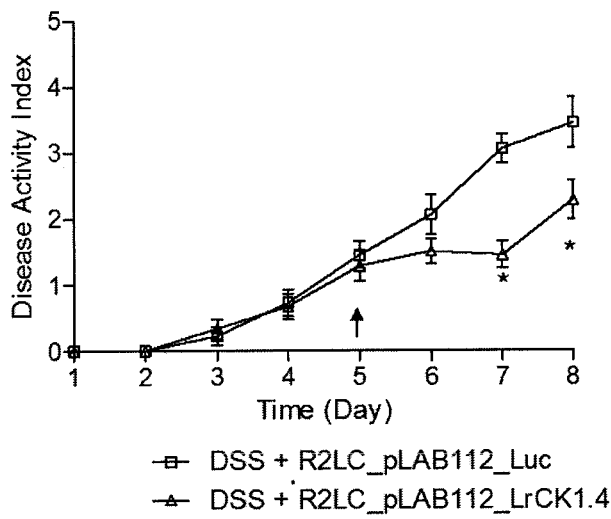
FIGS. 34A & 34B. Assessment of DSS-induced disease activity daily (FIG. 34A) and total disease burden, day 1-8 (FIG. 34B). Disease activity was assessed measuring relevant clinical symptoms as described earlier (Ref. 16). Arrow indicates start of treatment. Amelioration of DSS-induced colitis disease activity by treatment with *Lactobacillus reuteri* pLAB112_LrCK1.4 compared to treatment with pLAB112_Luc (DSS+R2LC_pLAB112_Luc; n=6, DSS+R2LC_pLAB112_LrCK1.4; n=6), Student's two-tailed unpaired t-test.
Figure 34B:
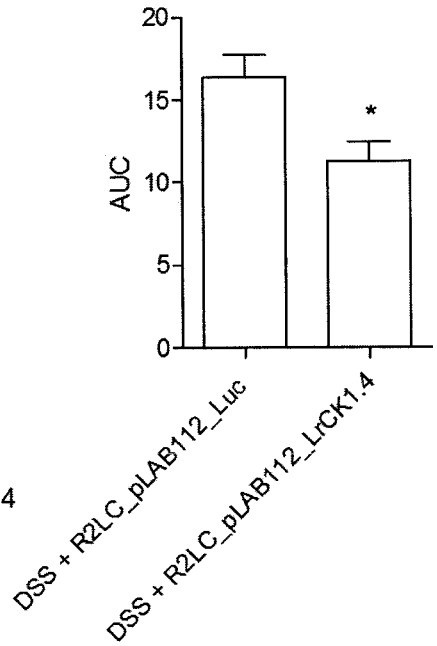

In contrast, disease development was ameliorated when *Lactobacillus reuteri* pLAB112_LrCK1.4 was administered to colitic mice which was not observed for treatment with pLAB112_Luc (FIGS. 34A & 34B) indicating effect of the delivered chemokine.

REFERENCES

1. Demidova-Rice T N, Hamblin M R and Herman I M. Acute and impaired wound healing: pathophysiology and current methods for drug delivery, part 1: normal and chronic wounds: biology, causes, and approaches to care. *Advances in skin & wound care*. 2012; 25:304-14.
2. Demidova-Rice T N, Hamblin M R and Herman I M. Acute and impaired wound healing: pathophysiology and current methods for drug delivery, part 2: role of growth factors in normal and pathological wound healing: therapeutic potential and methods of delivery. *Advances in skin & wound care*. 2012; 25:349-70.
3. Salcedo R, Wasserman K, Young H A, Grimm M C, Howard O M Z, Anver M R, Kleinman H K, Murphy W J and Oppenheim J J. Vascular Endothelial Growth Factor and Basic Fibroblast Growth Factor Induce Expression of CXCR4 on Human Endothelial Cells: In Vivo Neovascularization Induced by Stromal-Derived Factor-1α. *The American Journal of Pathology*. 1999; 154:1125-1135.
4. Hattermann K, Sebens S, Helm O, Schmitt A D, Mentlein R, Mehdorn H M and Held-Feindt J. Chemokine expression profile of freshly isolated human glioblastoma-associated macrophages/microglia. *Oncology reports*. 2014; 32:270-6.

5. Badillo A T, Chung S, Zhang L, Zoltick P and Liechty K W. Lentiviral gene transfer of SDF-1alpha to wounds improves diabetic wound healing. *The Journal of surgical research.* 2007; 143:35-42.
6. Lee W Y, Wang C J, Lin T Y, Hsiao C L and Luo C W. CXCL17, an orphan chemokine, acts as a novel angiogenic and anti-inflammatory factor. *American journal of physiology Endocrinology and metabolism.* 2013; 304: E32-40.
7. Burkhardt A M, Tai K P, Flores-Guiterrez J P, Vilches-Cisneros N, Kamdar K, Barbosa-Quintana O, Valle-Rios R, Hevezi P A, Zuñiga J, Selman M, Ouellette A J and Zlotnik A. CXCL17 Is a Mucosal Chemokine Elevated in Idiopathic Pulmonary Fibrosis That Exhibits Broad Antimicrobial Activity. *The Journal of Immunology.* 2012; 188:6399-6406.
8. Goren I, Pfeilschifter J and Frank S. Uptake of Neutrophil-Derived Ym1 Protein Distinguishes Wound Macrophages in the Absence of Interleukin-4 Signaling in Murine Wound Healing. *Am J Pathol.* 2014.
9. Poutahidis T, Kearney S M, Levkovich T, Qi P, Varian B J, Lakritz J R, Ibrahim Y M, Chatzigiagkos A, Alm E J and Erdman S E. Microbial symbionts accelerate wound healing via the neuropeptide hormone oxytocin. *PLoS One.* 2013; 8:e78898.
10. Ramos A N, Cabral M E, Noseda D, Bosch A, Yantorno O M and Valdez J C. Antipathogenic properties of *Lactobacillus plantarum* on *Pseudomonas aeruginosa*: the potential use of its supernatants in the treatment of infected chronic wounds. *Wound repair and regeneration: official publication of the Wound Healing Society [and] the European Tissue Repair Society.* 2012; 20:552-62.
11. Sørvig E, Mathiesen G, Naterstad K, Eijsink V G H and Axelsson L. High-level, inducible gene expression in *Lactobacillus sakei* and *Lactobacillus plantarum* using versatile expression vectors. *Microbiology.* 2005; 151: 2439-2449.
12. Eijsink V G, Axelsson L, Diep D B, Havarstein L S, Holo H and Nes I F. Production of class II bacteriocins by lactic acid bacteria; an example of biological warfare and communication. *Antonie van Leeuwenhoek.* 2002; 81:639-54.
13. Gao Z, Tseng C-h, Pei Z and Blaser M J. Molecular analysis of human forearm superficial skin bacterial biota. *Proceedings of the National Academy of Sciences.* 2007; 104:2927-2932.
14. Gethin G. The significance of surface pH in chronic wounds. *Wounds UK.* 2007; 3:52-56.
15. Sørvig E, Grönqvist S, Naterstad K, Mathiesen G, Eijsink V G, and Axelsson L. Construction of vectors for inducible gene expression in *Lactobacillus sakei* and *L plantarum*. *FEMS Microbiol Lett.* 2003; 229(1):119-126.
16. Cooper H. S., Murthy S. N., Shah R. S., Sedergran D. J. Clinicopathologic study of dextran sulfate sodium experimental murine colitis. Lab. Invest. 1993; 69(2):238-249.
17. Nyman E, Huss F, Nyman T, Junker J, Kratz G. Hyaluronic acid, an important factor in the wound healing properties of amniotic fluid: in vitro studies of re-epithelialisation in human skin wounds. J Plast Surg Hand Surg. 2013 April; 47(2):89-92.
18. Vågesjö E, Christoffersson G, Waldén T, Carlsson P, Essand M, Korsgren O, and Phillipson M. Immunological shielding by induced recruitment of regulatory T lymphocytes delays rejection of islets transplanted to muscle. Cell transplantation. 2015; 24(2):263-76.
19. Böhmer N, König S and Fischer L. A novel manganese starvation-inducible expression system for *Lactobacillus plantarum*. FEMS Microbiol Lett 342 (2013) 37-44.
20. Duong, T, Miller, M., Barrangou, R., Azcarate-Peril A. and Klaenhammer T., Construction of vectors for inducible and constitutive gene expression in *Lactobacillus* mbt_200 357. Microbial Biotechnology (2010) 4(3), 357-367.
21. Sørvig E, Mathiesen G, Naterstad K, Eijsink V G, and Axelsson L. High-level, inducible gene expression in *Lactobacillus sakei* and *Lactobacillus plantarum* using versatile expression vectors. Microbiology. 2005 July; 151(Pt 7):2439-49.
22. Nesmelova I, Sham Y, Gao J, and Mayo K. CXC and C C chemokines form mixed heterodimers association free energies from molecular dynamics simulations and experimental correlations. JBC Papers in Press, Jun. 12, 2008, DOI 10.1074/jbc.M803308200
23. Bellocq A, Suberville S, Philippe C, Bertrand F, Perez J, Fouqueray B, Cherqui G, Baud L. Low environmental pH is responsible for the induction of nitric-oxide synthase in macrophages. Evidence for involvement of nuclear factor-kappaB activation. J Biol Chem. 1998 Feb. 27; 273 (9):5086-92.
24. Thompson J, Higgins D G, Gibson T J. CLUSTAL W: improving the sensitivity of progressive multiple sequence alignment through sequence weighting, position-specific gap penalties and weight matrix choice (1994) Nucleic Acids Res., 22: 4673-4680.
25. Myers E and Miller W, Optimal alignments in linear space. (1988) CABIOS, 4: 11-17.
26. W. R. Pearson and D. J. Lipman. Improved Tools for Biological Sequence Analysis (1988) PNAS, 85:2444-2448.
27. W, R. Pearson (1990), Rapid and sensitive sequence comparison with FASTP and FASTA. Methods Enzymol., 183: 63-98,
28. Altschul S F, Madden T L, Schäffer A A, Zhang J, Zhang Z, Miller W, Lipman D J. (1997) Gapped BLAST and PSI-BLAST: a new generation of protein database search programs. Nucleic Acids Res., 25: 3389-3402.
29. Holm L and Sander C. Protein structure comparison by alignment of distance matrices (1993) J. Mol. Biol., 233: 123-38; 9.
30. Holm L and Sander C. Dali: a network tool for protein structure comparison. (1995) Trends Biochem. Sci., 20: 478-480.
31. Holm L and Sander C. Touring protein fold space with Dali/FSSP. (1998) Nucleic Acid Res., 26: 316-9).
32. Massena S, Christoffersson G, Vågesjö E, Seignez C, Gustafsson K, Binet F, Herrera Hidalgo C, Giraud A, Lomei J, Weström S, Shibuya M, Claesson-Welsh L, Gerwins P, Welsh M, Kreuger J, Phillipson M. Identification and characterization of VEGF-A-responsive neutrophils expressing CD49d, VEGFR1, and CXCR4 in mice and humans. Blood. 2015 Oct. 22; 126(17):2016-26. doi: 10.1182/blood-2015-03-631572. Epub 2015 Aug. 18.
33. Hatse S, Princen K, Liekens S, Vermeire K, De Clercq E, Schols D. Fluorescent CXCL12AF647 as a novel probe for nonradioactive CXCL12/CXCR4 cellular interaction studies. Cytometry A. 2004 October; 61(2):178-88.
34. Drury L, Ziarekb J, Gravelc, S, Veldkampb C, Takekoshif T, Hwangf S, Hevekerc N, Volkmanb B and Dwinella M. Monomeric and dimeric CXCL12 inhibit metastasis through distinct CXCR4 interactions and signaling pathways. PNAS Oct. 25, 2011, vol. 108, no. 43, pages 17655-17660

SEQUENCES

TABLE IV

Summary of Sequence Listing

| SEQ ID NO: | Description |
|---|---|
| 1. | mLrCK1_opt DNA |
| 2. | mLrCK1_opt protein |
| 3. | mCXCL12 native protein |
| 4. | hLrCK1_opt DNA |
| 5. | hLrCK1_opt protein |
| 6. | hCXCL12 native protein |
| 7. | mLrCK2_opt DNA |
| 8. | mLrCK2_opt protein |
| 9. | mCXCL17 native protein |
| 10. | hLrCK2_opt DNA |
| 11. | hLrCK2_opt protein |
| 12. | hCXCL17 native protein |

TABLE IV-continued

Summary of Sequence Listing

| SEQ ID NO: | Description |
|---|---|
| 13. | mYm1_opt DNA |
| 14. | mYm1 protein |
| 15. | mYm1 native protein |
| 16. | hYm1_opt DNA |
| 17. | hYm1 protein |
| 18. | hYm1 native protein |
| 19. | SppIP; activation peptide |
| 20. | pSIP411 DNA |
| 21. | pSIP411 protein |
| 22. | PCR primer |
| 23. | PCR primer |
| 24. | pVAX1 DNA |
| 25. | pCTR DNA insert |
| 26. | pCXCL12 DNA insert |

The invention claimed is:

1. A plasmid which is capable of expressing a protein in lactic acid bacteria, wherein said protein is CXCL12, and the plasmid comprises one or more nucleotide sequences having at least 80% sequence identity to SEQ ID NO: 1 or SEQ ID NO: 4.

2. The plasmid of claim 1, wherein said one or more nucleotide sequences encodes a protein selected from:
   (i) murine CXCL12-1α having an amino acid sequence with at least 80% sequence identity to SEQ ID NO: 3 or 2; or
   (ii) human CXCL12-1α having an amino acid sequence with at least 80% sequence identity to SEQ ID NO: 6 or 5.

3. The plasmid according to claim 1, wherein the plasmid comprises one or more regulatory sequences which permit expression in lactic acid bacteria, the regulatory sequences being obtained or derived from lactic acid bacteria.

4. The plasmid according to claim 1, wherein expression of said protein is regulatable.

5. The plasmid according to claim 1, wherein the plasmid comprises one or more nucleotide sequences encoding one or more of said proteins under the control of an inducible promoter.

6. The plasmid according to claim 1, wherein the plasmid comprises an inducible promoter and regulatory elements from the nisin regulon, the sakacin A regulon or the sakacin P regulon.

7. The plasmid according to claim 5, wherein the inducible promoter is the PorfX promoter from the sakacin P regulon.

8. The plasmid according to claim 1, which is derived from the plasmid designated pSIP411 having a sequence of SEQ ID NO: 20.

9. The recombinant plasmid according to claim 1, wherein the one or more nucleotide sequences encoding the protein is codon-optimised for expression in lactic acid bacteria.

10. A lactic acid bacterial strain transformed with the plasmid according to claim 1.

11. The bacterial strain according to claim 10, which is a *Lactobacillus* strain.

12. The bacterial strain according to claim 11, wherein the *Lactobacillus* strain is *Lactobacillus reuteri*.

13. A wound dressing comprising the bacterial strain according to claim 10.

14. A pharmaceutical composition comprising the bacterial strain according to claim 10.

15. A method of treating a human or animal subject to heal a wound, said method comprising administering to said subject, or to the wound in said subject, an amount of the bacterial strain of claim 10 effective to promote healing of the wound.

16. The method of claim 15, wherein the wound is a cutaneous or mucosal wound.

17. A kit for healing wounds, said kit comprising:
   (i) lactic acid bacteria comprising the plasmid of claim 1, wherein said plasmid comprises a nucleotide sequence encoding said protein under the control of an inducible promoter capable of expressing the protein in lactic acid bacteria; and
   (ii) an inducer for the promoter.

18. The kit of claim 17, the kit comprising a pharmaceutical product comprising:
   (i) the lactic acid bacteria comprising the plasmid of claim 1, wherein said plasmid comprises the nucleotide sequence encoding said protein under the control of the inducible promoter capable of expressing the protein in lactic acid bacteria; and
   (ii) the inducer for the promoter
   the pharmaceutical product being a combined preparation for separate, sequential or simultaneous use in wound healing.

19. A medical device comprising the bacterial strain according to claim 10.

20. The bacterial strain of claim 10 wherein the bacteria are freeze-dried.

21. A kit for healing wounds, said kit comprising:
   the bacterial strain of claim 20, wherein the plasmid comprises a nucleotide sequence encoding the protein under the control of an inducible promoter capable of expressing the protein in lactic acid bacteria;
   an inducer for the promoter; and
   a liquid for resuspending the freeze-dried bacteria.

22. The kit of claim 21, wherein the liquid comprises the inducer.

23. The kit of claim 17, wherein the kit further comprises a wound dressing, and the wound dressing comprises the bacteria.

24. The kit of claim 17, wherein the kit further comprises a wound dressing.

25. The plasmid of claim 1, wherein the one or more nucleotide sequences comprise a nucleotide sequence comprising the sequence of SEQ ID NO: 1 or SEQ ID NO: 4.

26. The plasmid of claim 2, wherein said one or more nucleotide sequences encodes a protein selected from:
   (i) murine CXCL12-1α having the amino acid sequence as shown in SEQ ID NO: 3 or 2;
   (ii) human CXCL12-1α having the amino acid sequence as shown in SEQ ID NO: 6 or 5.

27. The recombinant plasmid according to claim 9, wherein the mature or cleaved form of the protein encoded by the codon-optimised sequence is identical to the native protein.

* * * * *